US012592305B2

(12) United States Patent
Xavier et al.

(10) Patent No.: US 12,592,305 B2
(45) Date of Patent: Mar. 31, 2026

(54) DRUG LIBRARY MANAGER WITH CUSTOMIZED WORKSHEETS

(71) Applicant: ICU Medical, Inc., San Clemente, CA (US)

(72) Inventors: Ben Xavier, San Diego, CA (US); Dennis Krabbe, San Diego, CA (US); Timothy Kil, San Diego, CA (US); Jody Polk, San Diego, CA (US); Aaron Fields-Cypress, San Marcos, CA (US); Julius Tobias, San Diego, CA (US)

(73) Assignee: ICU Medical, Inc., San Clemente, CA (US)

( * ) Notice: Subject to any disclaimer, the term of this patent is extended or adjusted under 35 U.S.C. 154(b) by 0 days.

(21) Appl. No.: 17/659,454

(22) Filed: Apr. 15, 2022

(65) Prior Publication Data

US 2022/0384059 A1 Dec. 1, 2022

Related U.S. Application Data

(63) Continuation of application No. 16/512,243, filed on Jul. 15, 2019, now Pat. No. 11,309,070, which is a
(Continued)

(51) Int. Cl.
*G16H 20/17* (2018.01)
*A61M 5/142* (2006.01)
(Continued)

(52) U.S. Cl.
CPC ............ *G16H 20/17* (2018.01); *A61M 5/142* (2013.01); *A61M 5/172* (2013.01); *G16C 20/62* (2019.02);
(Continued)

(58) Field of Classification Search
None
See application file for complete search history.

(56) References Cited

U.S. PATENT DOCUMENTS 4,024,864 A 5/1977 Davies et al.
4,055,175 A 10/1977 Clemens et al.
(Continued)

FOREIGN PATENT DOCUMENTS

AU 2004226440 10/2004
AU 2004305087 7/2005
(Continued)

OTHER PUBLICATIONS

Frank Doesburg et al., Improved Usability of a Multi-Infusion Setup Using a Centralized Control Interface: A Task-Based Usability Test, 2017, PLoS One 12(8): e0183104. https://doi.org/10.1371/journal.pone.0183104 (Year: 2017).*
(Continued)

*Primary Examiner* — Jonathon A. Szumny
*Assistant Examiner* — Nicholas Akogyeram, II
(74) *Attorney, Agent, or Firm* — Knobbe, Martens, Olson & Bear, LLP

(57) ABSTRACT

A drug library management system facilitates centralized management of the drug libraries that are used by various infusion pumps, including in clinical environments that have different types and/or versions of infusion pumps. Medications, administration rules, critical care area rules, and the like can be maintained using the drug library management system. The drug library management system can generate and distribute drug library data in pump-specific formats or other customized formats as needed.

20 Claims, 10 Drawing Sheets

Related U.S. Application Data continuation of application No. PCT/US2019/041715, filed on Jul. 12, 2019.

(60) Provisional application No. 62/703,772, filed on Jul. 26, 2018.

(51) Int. Cl.

| | |
|---|---|
| *A61M 5/172* | (2006.01) |
| *G16C 20/62* | (2019.01) |
| *G16H 40/40* | (2018.01) |
| *G16H 70/40* | (2018.01) |

(52) U.S. Cl.
CPC ............. *G16H 40/40* (2018.01); *G16H 70/40* (2018.01); *A61M 2205/3553* (2013.01); *A61M 2205/3584* (2013.01); *A61M 2205/50* (2013.01); *A61M 2205/52* (2013.01); *A61M 2205/6009* (2013.01)

(56) References Cited

U.S. PATENT DOCUMENTS

| | | | |
|---|---|---|---|
| 4,151,845 | A | 5/1979 | Clemens |
| 4,213,454 | A | 7/1980 | Shim |
| 4,240,438 | A | 12/1980 | Updike et al. |
| 4,280,494 | A | 7/1981 | Cosgrove et al. |
| 4,308,866 | A | 1/1982 | Jeliffe |
| 4,370,983 | A | 2/1983 | Lichtenstein et al. |
| 4,373,527 | A | 2/1983 | Fischell |
| 4,392,849 | A | 7/1983 | Petre et al. |
| 4,395,259 | A | 7/1983 | Prestele et al. |
| 4,457,751 | A | 7/1984 | Rodler |
| 4,464,170 | A | 8/1984 | Clemens |
| 4,469,481 | A | 9/1984 | Kobayashi |
| 4,475,901 | A | 10/1984 | Kraegen et al. |
| 4,494,950 | A | 1/1985 | Fischell |
| 4,498,843 | A | 2/1985 | Schneider et al. |
| 4,515,584 | A | 5/1985 | Abe et al. |
| 4,526,568 | A | 7/1985 | Clemens et al. |
| 4,529,401 | A | 7/1985 | Leslie et al. |
| 4,543,955 | A | 10/1985 | Schroeppel |
| 4,551,133 | A | 11/1985 | Zegers de Beyl et al. |
| 4,553,958 | A | 11/1985 | LeCocq |
| 4,559,037 | A | 12/1985 | Franetzki et al. |
| 4,613,937 | A | 9/1986 | Batty |
| 4,624,661 | A | 11/1986 | Arimond |
| 4,633,878 | A | 1/1987 | Bombardieri |
| 4,634,426 | A | 1/1987 | Kamen |
| 4,634,427 | A | 1/1987 | Hannula et al. |
| 4,674,652 | A | 6/1987 | Aten et al. |
| 4,676,776 | A | 6/1987 | Howson et al. |
| 4,679,562 | A | 7/1987 | Luksha |
| 4,685,903 | A | 8/1987 | Cable et al. |
| 4,695,954 | A | 9/1987 | Rose |
| 4,696,671 | A | 9/1987 | Epstein et al. |
| 4,714,462 | A | 12/1987 | DiDomenico |
| 4,722,734 | A | 2/1988 | Kolin |
| 4,730,849 | A | 3/1988 | Siegel |
| 4,731,051 | A | 3/1988 | Fischell |
| 4,741,732 | A | 5/1988 | Crankshaw et al. |
| 4,756,706 | A | 7/1988 | Kerns et al. |
| 4,776,842 | A | 10/1988 | Franetzki et al. |
| 4,785,969 | A | 11/1988 | McLaughlin |
| 4,803,625 | A | 2/1989 | Fu et al. |
| 4,835,372 | A | 5/1989 | Gombrich et al. |
| 4,838,275 | A | 6/1989 | Lee |
| 4,838,856 | A | 6/1989 | Mulreany et al. |
| 4,838,857 | A | 6/1989 | Strowe et al. |
| 4,854,324 | A | 8/1989 | Hirschman et al. |
| 4,857,716 | A | 8/1989 | Gombrich et al. |
| 4,858,154 | A | 8/1989 | Anderson et al. |
| 4,898,578 | A | 2/1990 | Rubalcaba, Jr. |
| 4,908,017 | A | 3/1990 | Howson et al. |
| 4,933,873 | A | 6/1990 | Kaufman et al. |
| 4,943,279 | A | 7/1990 | Samiotes et al. |
| 4,946,439 | A | 8/1990 | Eggers |
| 4,953,745 | A | 9/1990 | Rowlett |
| 4,978,335 | A | 12/1990 | Arthur, III |
| 5,000,739 | A | 3/1991 | Kulisz et al. |
| 5,010,473 | A | 4/1991 | Jacobs |
| 5,014,698 | A | 5/1991 | Cohen |
| 5,016,172 | A | 5/1991 | Dessertine |
| 5,026,084 | A | 6/1991 | Paisfield |
| 5,034,004 | A | 7/1991 | Crankshaw |
| 5,041,086 | A | 8/1991 | Koenig et al. |
| 5,058,161 | A | 10/1991 | Weiss |
| 5,078,683 | A | 1/1992 | Sancoff et al. |
| 5,084,828 | A | 1/1992 | Kaufman et al. |
| 5,088,981 | A | 2/1992 | Howson et al. |
| 5,097,505 | A | 3/1992 | Weiss |
| 5,100,380 | A | 3/1992 | Epstein et al. |
| 5,102,392 | A | 4/1992 | Sakai et al. |
| 5,104,374 | A | 4/1992 | Bishko et al. |
| 5,109,850 | A | 5/1992 | Blanco et al. |
| 5,131,816 | A | 7/1992 | Brown |
| 5,142,484 | A | 8/1992 | Kaufman et al. |
| 5,153,827 | A | 10/1992 | Coutre et al. |
| 5,157,640 | A | 10/1992 | Backner |
| 5,161,222 | A | 11/1992 | Montejo et al. |
| 5,177,993 | A | 1/1993 | Beckman et al. |
| 5,181,910 | A | 1/1993 | Scanlon |
| 5,190,522 | A | 3/1993 | Wocicki et al. |
| 5,199,439 | A | 4/1993 | Zimmerman et al. |
| 5,200,891 | A | 4/1993 | Kehr et al. |
| 5,216,597 | A | 6/1993 | Beckers |
| 5,221,268 | A | 6/1993 | Barton et al. |
| 5,230,061 | A | 7/1993 | Welch |
| 5,243,982 | A | 9/1993 | Möstl et al. |
| 5,244,463 | A | 9/1993 | Cordner, Jr. et al. |
| 5,249,260 | A | 9/1993 | Nigawara et al. |
| 5,254,096 | A | 10/1993 | Rondelet et al. |
| 5,256,156 | A | 10/1993 | Kern et al. |
| 5,256,157 | A | 10/1993 | Samiotes et al. |
| 5,261,702 | A | 11/1993 | Mayfield |
| 5,317,506 | A | 5/1994 | Coutre et al. |
| 5,319,355 | A | 6/1994 | Russek |
| 5,319,363 | A | 6/1994 | Welch et al. |
| 5,330,634 | A | 7/1994 | Wong et al. |
| 5,338,157 | A | 8/1994 | Blomquist |
| 5,341,476 | A | 8/1994 | Lowell |
| 5,364,346 | A | 11/1994 | Schrezenmeir |
| 5,366,346 | A | 11/1994 | Danby |
| 5,368,562 | A | 11/1994 | Blomquist et al. |
| 5,373,454 | A | 12/1994 | Kanda et al. |
| 5,376,070 | A | 12/1994 | Purvis et al. |
| 5,378,231 | A | 1/1995 | Johnson et al. |
| 5,389,071 | A | 2/1995 | Kawahara et al. |
| 5,389,078 | A | 2/1995 | Zalesky et al. |
| 5,417,222 | A | 5/1995 | Dempsey et al. |
| 5,423,748 | A | 6/1995 | Uhala |
| 5,429,602 | A | 7/1995 | Hauser |
| 5,431,627 | A | 7/1995 | Pastrone et al. |
| 5,432,777 | A | 7/1995 | Le Boudec et al. |
| 5,445,621 | A | 8/1995 | Poli et al. |
| 5,447,164 | A | 9/1995 | Shaya et al. |
| 5,455,851 | A | 10/1995 | Chaco et al. |
| 5,461,365 | A | 10/1995 | Schlager et al. |
| 5,464,392 | A | 11/1995 | Epstein et al. |
| 5,465,082 | A | 11/1995 | Chaco |
| 5,485,408 | A | 1/1996 | Blomquist |
| 5,486,286 | A | 1/1996 | Peterson et al. |
| 5,493,430 | A | 2/1996 | Lu et al. |
| 5,496,273 | A | 3/1996 | Pastrone et al. |
| 5,505,828 | A | 4/1996 | Wong et al. |
| 5,507,288 | A | 4/1996 | Bocker et al. |
| 5,507,786 | A | 4/1996 | Morgan et al. |
| 5,508,499 | A | 4/1996 | Ferrario |
| 5,515,713 | A | 5/1996 | Saugues et al. |
| 5,520,637 | A | 5/1996 | Pager et al. |
| 5,522,798 | A | 6/1996 | Johnson et al. |
| 5,547,470 | A | 8/1996 | Johnson et al. |
| 5,554,013 | A | 9/1996 | Owens et al. |
| 5,562,615 | A | 10/1996 | Nassif |

(56)                References Cited

U.S. PATENT DOCUMENTS

| 5,577,169 | A | 11/1996 | Prezioso |
| 5,582,323 | A | 12/1996 | Kurtenbach |
| 5,582,593 | A | 12/1996 | Hultman |
| 5,594,786 | A | 1/1997 | Chaco et al. |
| 5,598,519 | A | 1/1997 | Narayanan |
| 5,620,608 | A | 4/1997 | Rosa et al. |
| 5,630,710 | A | 5/1997 | Tune et al. |
| 5,636,044 | A | 6/1997 | Yuan et al. |
| 5,643,212 | A | 7/1997 | Coutre et al. |
| 5,651,775 | A | 7/1997 | Walker et al. |
| 5,658,131 | A | 8/1997 | Aoki et al. |
| 5,658,250 | A | 8/1997 | Blomquist et al. |
| 5,665,065 | A | 9/1997 | Colman et al. |
| 5,669,877 | A | 9/1997 | Blomquist |
| 5,672,154 | A | 9/1997 | Sillén et al. |
| 5,681,285 | A | 10/1997 | Ford et al. |
| 5,685,844 | A | 11/1997 | Marttila |
| 5,687,717 | A | 11/1997 | Halpern et al. |
| 5,689,229 | A | 11/1997 | Chaco et al. |
| 5,697,899 | A | 12/1997 | Hillman et al. |
| 5,699,509 | A | 12/1997 | Gary et al. |
| 5,708,714 | A | 1/1998 | Lopez et al. |
| 5,713,350 | A | 2/1998 | Yokota et al. |
| 5,713,856 | A | 2/1998 | Eggers et al. |
| 5,718,562 | A | 2/1998 | Lawless et al. |
| 5,719,761 | A | 2/1998 | Gatti et al. |
| 5,733,259 | A | 3/1998 | Valcke et al. |
| 5,738,102 | A | 4/1998 | Lemelson |
| 5,744,027 | A | 4/1998 | Connell et al. |
| 5,752,621 | A | 5/1998 | Passamante |
| 5,754,111 | A | 5/1998 | Garcia |
| 5,764,034 | A | 6/1998 | Bowman et al. |
| 5,764,159 | A | 6/1998 | Neftel et al. |
| 5,772,635 | A | 6/1998 | Dastur et al. |
| 5,774,865 | A | 6/1998 | Glynn |
| 5,778,256 | A | 7/1998 | Darbee |
| 5,778,345 | A | 7/1998 | McCartney |
| 5,781,442 | A | 7/1998 | Engleson et al. |
| 5,782,805 | A | 7/1998 | Meinzer et al. |
| 5,788,669 | A | 8/1998 | Peterson |
| 5,797,515 | A | 8/1998 | Liff et al. |
| 5,800,387 | A | 9/1998 | Duffy et al. |
| 5,814,015 | A | 9/1998 | Gargano et al. |
| 5,822,544 | A | 10/1998 | Chaco et al. |
| 5,822,715 | A | 10/1998 | Worthington et al. |
| 5,827,179 | A | 10/1998 | Lichter et al. |
| 5,832,448 | A | 11/1998 | Brown |
| 5,836,910 | A | 11/1998 | Duffy et al. |
| 5,850,344 | A | 12/1998 | Conkright |
| 5,867,821 | A | 2/1999 | Ballantyne et al. |
| 5,870,733 | A | 2/1999 | Bass et al. |
| 5,871,465 | A | 2/1999 | Vasko |
| 5,873,731 | A | 2/1999 | Predergast |
| 5,885,245 | A | 3/1999 | Lynch et al. |
| 5,897,493 | A | 4/1999 | Brown |
| 5,897,498 | A | 4/1999 | Canfield, II et al. |
| 5,910,252 | A | 6/1999 | Truitt et al. |
| 5,912,818 | A | 6/1999 | McGrady et al. |
| 5,915,240 | A | 6/1999 | Karpf |
| 5,920,054 | A | 7/1999 | Uber, III |
| 5,920,263 | A | 7/1999 | Huttenhoff et al. |
| 5,924,074 | A | 7/1999 | Evans |
| 5,931,764 | A | 8/1999 | Freeman et al. |
| 5,935,099 | A | 8/1999 | Peterson et al. |
| 5,935,106 | A | 8/1999 | Olsen |
| 5,941,846 | A | 8/1999 | Duffy et al. |
| 5,956,501 | A | 9/1999 | Brown |
| 5,957,885 | A | 9/1999 | Bollish et al. |
| 5,960,085 | A | 9/1999 | de la Huerga |
| 5,961,448 | A | 10/1999 | Swenson et al. |
| 5,967,559 | A | 10/1999 | Abramowitz |
| 5,971,594 | A | 10/1999 | Sahai et al. |
| 5,975,081 | A | 11/1999 | Hood et al. |
| 5,990,838 | A | 11/1999 | Burns et al. |
| 5,997,476 | A | 12/1999 | Brown |
| 6,000,828 | A | 12/1999 | Leet |
| 6,003,006 | A | 12/1999 | Colella et al. |
| 6,012,034 | A | 1/2000 | Hamparian et al. |
| 6,017,318 | A | 1/2000 | Gauthier et al. |
| 6,021,392 | A | 2/2000 | Lester et al. |
| 6,024,539 | A | 2/2000 | Blomquist |
| 6,024,699 | A | 2/2000 | Surwit et al. |
| 6,032,155 | A | 2/2000 | de la Huerga |
| 6,032,676 | A | 3/2000 | Moore |
| 6,039,251 | A | 3/2000 | Holowko et al. |
| 6,070,761 | A | 6/2000 | Bloom et al. |
| 6,073,106 | A | 6/2000 | Rozen et al. |
| 6,104,295 | A | 8/2000 | Gaisser et al. |
| 6,112,182 | A | 8/2000 | Akers et al. |
| 6,112,323 | A | 8/2000 | Meizlik et al. |
| RE36,871 | E | 9/2000 | Epstein et al. |
| 6,115,365 | A | 9/2000 | Newberg |
| 6,115,390 | A | 9/2000 | Chuah |
| 6,122,536 | A | 9/2000 | Sun et al. |
| 6,126,637 | A | 10/2000 | Kriesel et al. |
| 6,135,949 | A | 10/2000 | Russo et al. |
| 6,150,942 | A | 11/2000 | O'Brien |
| 6,151,643 | A | 11/2000 | Cheng et al. |
| 6,157,914 | A | 12/2000 | Seto et al. |
| 6,159,147 | A | 12/2000 | Lichter et al. |
| 6,167,567 | A | 12/2000 | Chiles et al. |
| 6,182,667 | B1 | 2/2001 | Hanks et al. |
| 6,189,105 | B1 | 2/2001 | Lopes |
| 6,195,589 | B1 | 2/2001 | Ketcham |
| 6,208,974 | B1 | 3/2001 | Campbell et al. |
| 6,222,323 | B1 | 4/2001 | Yamashita et al. |
| 6,223,440 | B1 | 5/2001 | Rashman |
| 6,226,277 | B1 | 5/2001 | Chuah |
| 6,227,371 | B1 | 5/2001 | Song |
| 6,234,176 | B1 | 5/2001 | Domae et al. |
| 6,241,704 | B1 | 6/2001 | Peterson et al. |
| 6,248,067 | B1 | 6/2001 | Causey, III et al. |
| 6,249,705 | B1 | 6/2001 | Snell |
| 6,257,265 | B1 | 7/2001 | Brunner et al. |
| 6,259,355 | B1 | 7/2001 | Chaco et al. |
| 6,269,340 | B1 | 7/2001 | Ford et al. |
| 6,270,455 | B1 | 8/2001 | Brown |
| 6,271,813 | B1 | 8/2001 | Palalau |
| 6,277,072 | B1 | 8/2001 | Bardy |
| 6,280,380 | B1 | 8/2001 | Bardy |
| 6,283,761 | B1 | 9/2001 | Joao |
| 6,285,665 | B1 | 9/2001 | Chuah |
| 6,292,860 | B1 | 9/2001 | Cochcroft, Jr. |
| 6,312,378 | B1 | 11/2001 | Bardy |
| 6,327,254 | B1 | 12/2001 | Chuah |
| 6,330,008 | B1 | 12/2001 | Razdow et al. |
| 6,339,718 | B1 | 1/2002 | Zatezalo et al. |
| 6,346,886 | B1 | 2/2002 | de la Huerga |
| 6,363,282 | B1 | 3/2002 | Nichols et al. |
| 6,371,719 | B1 | 4/2002 | Hildebrandt |
| 6,377,548 | B1 | 4/2002 | Chuah |
| 6,388,951 | B1 | 5/2002 | Matsumoto et al. |
| 6,406,426 | B1 | 6/2002 | Reuss et al. |
| 6,408,330 | B1 | 6/2002 | de la Huerga |
| 6,418,334 | B1 | 7/2002 | Unger et al. |
| 6,427,088 | B1 | 7/2002 | Bowman et al. |
| 6,428,483 | B1 | 8/2002 | Carlebach |
| 6,442,432 | B2 | 8/2002 | Lee |
| 6,469,991 | B1 | 10/2002 | Chuah |
| 6,475,180 | B2 | 11/2002 | Peterson et al. |
| 6,482,158 | B2 | 11/2002 | Mault |
| 6,485,418 | B2 | 11/2002 | Yasushi et al. |
| 6,494,694 | B2 | 12/2002 | Lawless et al. |
| 6,494,831 | B1 | 12/2002 | Koritzinsky |
| 6,497,680 | B1 | 12/2002 | Holst et al. |
| 6,514,460 | B1 | 2/2003 | Fendrock |
| 6,517,482 | B1 | 2/2003 | Elden et al. |
| 6,519,569 | B1 | 2/2003 | White et al. |
| 6,520,930 | B2 | 2/2003 | Critchlow et al. |
| 6,540,672 | B1 | 4/2003 | Simonsen et al. |
| 6,542,902 | B2 | 4/2003 | Dulong et al. |
| 6,544,212 | B2 | 4/2003 | Galley et al. |
| 6,544,228 | B1 | 4/2003 | Heitmeier |
| 6,546,350 | B1 | 4/2003 | Hartmann et al. |

(56) References Cited

U.S. PATENT DOCUMENTS

| | | |
|---|---|---|
| 6,551,276 B1 | 4/2003 | Mann et al. |
| 6,554,798 B1 | 4/2003 | Mann et al. |
| 6,558,320 B1 | 5/2003 | Causey et al. |
| 6,558,351 B1 | 5/2003 | Steil et al. |
| 6,565,509 B1 | 5/2003 | Say et al. |
| 6,567,416 B1 | 5/2003 | Chuah |
| 6,571,294 B2 | 5/2003 | Simmon et al. |
| 6,572,542 B1 | 6/2003 | Houben et al. |
| 6,572,545 B2 | 6/2003 | Knobbe et al. |
| 6,578,002 B1 | 6/2003 | Derzay et al. |
| 6,581,117 B1 | 6/2003 | Klein et al. |
| 6,587,034 B1 | 7/2003 | Heiman et al. |
| 6,589,229 B1 | 7/2003 | Connelly et al. |
| 6,599,281 B1 | 7/2003 | Struys et al. |
| 6,602,191 B2 | 8/2003 | Quy |
| 6,605,072 B2 | 8/2003 | Struys et al. |
| 6,628,809 B1 | 9/2003 | Rowe et al. |
| 6,631,353 B1 | 10/2003 | Davis et al. |
| 6,640,246 B1 | 10/2003 | Gardy, Jr. et al. |
| 6,641,533 B2 | 11/2003 | Causey, III et al. |
| 6,647,299 B2 | 11/2003 | Bourget |
| 6,652,455 B1 | 11/2003 | Kocher |
| 6,653,937 B2 | 11/2003 | Nelson et al. |
| 6,659,947 B1 | 12/2003 | Carter et al. |
| 6,669,630 B1 | 12/2003 | Joliat et al. |
| 6,671,563 B1 | 12/2003 | Engleson et al. |
| 6,673,033 B1 | 1/2004 | Sciulli et al. |
| 6,674,403 B2 | 1/2004 | Gray et al. |
| 6,681,003 B2 | 1/2004 | Linder et al. |
| 6,689,091 B2 | 2/2004 | Bui et al. |
| 6,692,241 B2 | 2/2004 | Watanabe et al. |
| 6,694,191 B2 | 2/2004 | Starkweather et al. |
| 6,694,334 B2 | 2/2004 | DuLong et al. |
| 6,721,286 B1 | 4/2004 | Williams et al. |
| 6,721,582 B2 | 4/2004 | Trepagnier et al. |
| 6,725,200 B1 | 4/2004 | Rost |
| 6,731,989 B2 | 5/2004 | Engleson et al. |
| 6,740,072 B2 | 5/2004 | Starkweather et al. |
| 6,751,651 B2 | 6/2004 | Crockett |
| 6,752,787 B1 | 6/2004 | Causey, III et al. |
| 6,753,830 B2 | 6/2004 | Gelbman |
| 6,758,810 B2 | 7/2004 | Lebel et al. |
| 6,773,396 B2 | 8/2004 | Flach et al. |
| 6,774,786 B1 | 8/2004 | Havekost et al. |
| 6,775,577 B2 | 8/2004 | Cmkovich et al. |
| 6,780,156 B2 | 8/2004 | Haueter et al. |
| 6,790,198 B1 | 9/2004 | White et al. |
| 6,792,470 B2 | 9/2004 | Hakenberg et al. |
| 6,796,956 B2 | 9/2004 | Hartlaub et al. |
| 6,799,149 B2 | 9/2004 | Hartlaub |
| 6,809,653 B1 | 10/2004 | Mann et al. |
| 6,811,534 B2 | 11/2004 | Bowman, IV et al. |
| 6,816,605 B2 | 11/2004 | Rowe et al. |
| 6,839,753 B2 | 1/2005 | Biondi et al. |
| 6,852,104 B2 | 2/2005 | Blomquist |
| 6,859,134 B1 | 2/2005 | Heiman et al. |
| 6,871,211 B2 | 3/2005 | Labounty et al. |
| 6,873,268 B2 | 3/2005 | Lebel et al. |
| 6,876,303 B2 | 4/2005 | Reeder et al. |
| 6,885,881 B2 | 4/2005 | Leonhardt |
| 6,891,525 B2 | 5/2005 | Ogoro |
| 6,892,278 B2 | 5/2005 | Ebergen |
| 6,899,695 B2 | 5/2005 | Herrera |
| 6,915,170 B2 | 7/2005 | Engleson et al. |
| 6,923,763 B1 | 8/2005 | Kovatchev et al. |
| 6,924,781 B1 | 8/2005 | Gelbman |
| 6,928,338 B1 | 8/2005 | Buchser et al. |
| 6,928,490 B1 | 8/2005 | Bucholz et al. |
| 6,936,029 B2 | 8/2005 | Mann et al. |
| 6,945,954 B2 | 9/2005 | Hochman et al. |
| 6,948,492 B2 | 9/2005 | Wemeling et al. |
| 6,958,677 B1 | 10/2005 | Carter |
| 6,958,691 B1 | 10/2005 | Anderson et al. |
| 6,958,705 B2 | 10/2005 | Lebel et al. |
| 6,961,448 B2 | 11/2005 | Nichols et al. |
| 6,969,352 B2 | 11/2005 | Chiang et al. |
| 6,969,865 B2 | 11/2005 | Duchon et al. |
| 6,974,437 B2 | 12/2005 | Lebel et al. |
| 6,979,326 B2 | 12/2005 | Mann et al. |
| 6,980,958 B1 | 12/2005 | Surwit et al. |
| 6,985,870 B2 | 1/2006 | Martucci et al. |
| 6,986,347 B2 | 1/2006 | Hickle |
| 6,997,880 B2 | 2/2006 | Carlebach et al. |
| 6,997,920 B2 | 2/2006 | Mann et al. |
| 6,998,984 B1 | 2/2006 | Zittrain |
| 7,016,752 B1 | 3/2006 | Ruben et al. |
| 7,017,293 B2 | 3/2006 | Riley |
| 7,025,743 B2 | 4/2006 | Mann et al. |
| 7,029,455 B2 | 4/2006 | Flaherty |
| 7,038,584 B2 | 5/2006 | Carter |
| 7,060,031 B2 | 6/2006 | Webb et al. |
| 7,060,059 B2 | 6/2006 | Keith et al. |
| 7,069,552 B2 | 6/2006 | Lindberg et al. |
| 7,072,725 B2 | 7/2006 | Bristol et al. |
| 7,079,035 B2 | 7/2006 | Bock et al. |
| 7,092,943 B2 | 8/2006 | Roese et al. |
| 7,096,072 B2 | 8/2006 | Engleson et al. |
| 7,099,809 B2 | 8/2006 | Dori |
| 7,103,419 B2 | 9/2006 | Engleson et al. |
| 7,103,578 B2 | 9/2006 | Beck et al. |
| 7,107,106 B2 | 9/2006 | Engleson et al. |
| 7,108,680 B2 | 9/2006 | Rohr et al. |
| 7,109,878 B2 | 9/2006 | Mann et al. |
| 7,114,002 B1 | 9/2006 | Okumura et al. |
| 7,117,041 B2 | 10/2006 | Engleson et al. |
| 7,136,645 B2 | 11/2006 | Hanson et al. |
| 7,137,964 B2 | 11/2006 | Flaherty |
| 7,142,190 B2 | 11/2006 | Martinez |
| 7,150,741 B2 | 12/2006 | Erickson et al. |
| 7,153,289 B2 | 12/2006 | Vasko |
| 7,154,397 B2 | 12/2006 | Zerhusen et al. |
| 7,156,807 B2 | 1/2007 | Carter et al. |
| 7,158,030 B2 | 1/2007 | Chung |
| 7,161,484 B2 | 1/2007 | Tsoukalis et al. |
| 7,167,755 B2 | 1/2007 | Seeberger et al. |
| 7,167,920 B2 | 1/2007 | Traversat |
| 7,171,277 B2 | 1/2007 | Engleson et al. |
| 7,171,492 B1 | 1/2007 | Borella et al. |
| 7,181,493 B2 | 2/2007 | English et al. |
| 7,185,288 B2 | 2/2007 | McKeever |
| 7,193,514 B2 | 3/2007 | Ritson |
| 7,197,025 B2 | 3/2007 | Chuah |
| 7,201,734 B2 | 4/2007 | Hickle |
| 7,204,823 B2 | 4/2007 | Estes et al. |
| 7,213,009 B2 | 5/2007 | Pestotnik |
| 7,216,802 B1 | 5/2007 | de la Huerga |
| 7,220,240 B2 | 5/2007 | Struys et al. |
| 7,224,979 B2 | 5/2007 | Singhal et al. |
| 7,229,430 B2 | 6/2007 | Hickle et al. |
| 7,230,529 B2 | 6/2007 | Ketcherside |
| 7,236,936 B2 | 6/2007 | White et al. |
| 7,238,164 B2 | 7/2007 | Childers et al. |
| 7,247,154 B2 | 7/2007 | Hickle |
| 7,248,239 B2 | 7/2007 | Dowling |
| 7,250,856 B2 | 7/2007 | Havekost et al. |
| 7,255,683 B2 | 8/2007 | Vanderveen et al. |
| 7,256,888 B2 | 8/2007 | Staehr et al. |
| 7,258,534 B2 | 8/2007 | Fathallah et al. |
| 7,263,213 B2 | 8/2007 | Rowe |
| 7,267,664 B2 | 9/2007 | Rizzo |
| 7,267,665 B2 | 9/2007 | Steil et al. |
| 7,275,156 B2 | 9/2007 | Balfanz et al. |
| 7,278,983 B2 | 10/2007 | Ireland et al. |
| 7,289,815 B2 | 10/2007 | Gfeller et al. |
| 7,289,948 B1 | 10/2007 | Mohri |
| 7,293,107 B1 | 11/2007 | Hanson et al. |
| 7,295,119 B2 | 11/2007 | Rappaport et al. |
| 7,295,556 B2 | 11/2007 | Roese et al. |
| 7,301,451 B2 | 11/2007 | Hastings |
| 7,308,300 B2 | 12/2007 | Toews et al. |
| 7,315,825 B2 | 1/2008 | Rosenfeld et al. |
| 7,319,386 B2 | 1/2008 | Collins, Jr. et al. |
| 7,324,000 B2 | 1/2008 | Zittrain et al. |
| 7,327,705 B2 | 2/2008 | Fletcher et al. |

(56)  References Cited

U.S. PATENT DOCUMENTS

| | | | |
|---|---|---|---|
| 7,343,224 | B2 | 3/2008 | DiGianfilippo et al. |
| 7,346,025 | B2 | 3/2008 | Bryson |
| 7,347,836 | B2 | 3/2008 | Peterson et al. |
| 7,354,420 | B2 | 4/2008 | Steil et al. |
| 7,369,897 | B2 | 5/2008 | Boveja et al. |
| 7,369,948 | B1 | 5/2008 | Ferenczi et al. |
| 7,383,088 | B2 | 6/2008 | Spinelli et al. |
| 7,384,410 | B2 | 6/2008 | Eggers et al. |
| 7,398,183 | B2 | 7/2008 | Holland et al. |
| 7,398,279 | B2 | 7/2008 | Muno, Jr. et al. |
| 7,399,277 | B2 | 7/2008 | Saidara et al. |
| 7,402,153 | B2 | 7/2008 | Steil et al. |
| 7,420,472 | B2 | 9/2008 | Tran |
| 7,432,807 | B2 | 10/2008 | Schmitt |
| 7,436,454 | B2 | 10/2008 | Yamaguchi et al. |
| 7,447,643 | B1 | 11/2008 | Olson |
| 7,454,314 | B2 | 11/2008 | Holland et al. |
| 7,457,804 | B2 | 11/2008 | Uber, III et al. |
| 7,464,040 | B2 | 12/2008 | Joao |
| 7,469,213 | B1 | 12/2008 | Rao |
| 7,471,994 | B2 | 12/2008 | Ford et al. |
| 7,483,756 | B2 | 1/2009 | Engleson et al. |
| 7,489,808 | B2 | 2/2009 | Gerder |
| 7,490,021 | B2 | 2/2009 | Holland et al. |
| 7,490,048 | B2 | 2/2009 | Joao |
| 7,491,187 | B2 | 2/2009 | Van Den Berghe et al. |
| 7,519,905 | B2 | 4/2009 | Kougiouris et al. |
| 7,523,401 | B1 | 4/2009 | Aldridge |
| 7,524,304 | B2 | 4/2009 | Genosar |
| 7,551,078 | B2 | 6/2009 | Carlson |
| 7,559,321 | B2 | 7/2009 | Wermeling et al. |
| 7,565,197 | B2 | 7/2009 | Haulbrich et al. |
| 7,572,230 | B2 | 8/2009 | Neumann et al. |
| 7,578,802 | B2 | 8/2009 | Hickle |
| 7,621,009 | B2 | 11/2009 | Elhabashy |
| D606,533 | S | 12/2009 | De Jong et al. |
| 7,636,718 | B1 | 12/2009 | Steen et al. |
| 7,640,172 | B2 | 12/2009 | Kuth |
| 7,645,258 | B2 | 1/2010 | White et al. |
| 7,647,237 | B2 | 1/2010 | Malave et al. |
| 7,662,124 | B2 | 2/2010 | Duchon et al. |
| 7,668,731 | B2 | 2/2010 | Martucci et al. |
| 7,671,733 | B2 | 3/2010 | McNeal et al. |
| 7,678,071 | B2 | 3/2010 | Lebel et al. |
| 7,687,678 | B2 | 3/2010 | Jacobs |
| 7,697,994 | B2 | 4/2010 | VanDanacker et al. |
| 7,698,239 | B2 | 4/2010 | Lieuallen |
| 7,705,727 | B2 | 4/2010 | Pestotnik |
| 7,724,147 | B2 | 5/2010 | Brown et al. |
| 7,739,126 | B1 | 6/2010 | Cave |
| 7,746,218 | B2 | 6/2010 | Collins, Jr. |
| 7,766,873 | B2 | 8/2010 | Moberg et al. |
| 7,776,029 | B2 | 8/2010 | Whitehurst et al. |
| 7,776,031 | B2 | 8/2010 | Hartlaub et al. |
| 7,785,313 | B2 | 8/2010 | Mastrototaro |
| 7,788,369 | B2 | 8/2010 | McAllen et al. |
| 7,806,852 | B1 | 10/2010 | Jurson |
| 7,806,886 | B2 | 10/2010 | Kanderian, Jr. et al. |
| 7,826,981 | B2 | 11/2010 | Goode, Jr. et al. |
| 7,835,927 | B2 | 11/2010 | Schlotterbeck et al. |
| 7,836,314 | B2 | 11/2010 | Chieu |
| 7,856,276 | B2 | 12/2010 | Ripart et al. |
| 7,860,583 | B2 | 12/2010 | Condurso et al. |
| 7,864,771 | B2 | 1/2011 | Tavares et al. |
| 7,868,754 | B2 | 1/2011 | Salvat, Jr. |
| 7,871,394 | B2 | 1/2011 | Halbert et al. |
| 7,886,231 | B2 | 2/2011 | Hopermann et al. |
| 7,895,053 | B2 | 2/2011 | Holland et al. |
| 7,896,842 | B2 | 3/2011 | Palmroos et al. |
| 7,899,546 | B2 | 3/2011 | Sieracki et al. |
| 7,905,710 | B2 | 3/2011 | Wang et al. |
| 7,920,061 | B2 | 4/2011 | Klein et al. |
| 7,933,780 | B2 | 4/2011 | de la Huerga |
| 7,938,796 | B2 | 5/2011 | Moubayed |
| 7,945,452 | B2 | 5/2011 | Fathallah et al. |
| 7,974,714 | B2 | 7/2011 | Hoffberg |
| 7,976,508 | B2 | 7/2011 | Hoag |
| 7,996,241 | B2 | 8/2011 | Zak |
| 8,034,026 | B2 | 10/2011 | Grant |
| 8,038,593 | B2 | 10/2011 | Friedman et al. |
| 8,048,040 | B2 | 11/2011 | Kiani |
| 8,060,576 | B2 | 11/2011 | Chan et al. |
| 8,065,161 | B2 | 11/2011 | Howard et al. |
| 8,066,672 | B2 | 11/2011 | Mandro |
| 8,075,514 | B2 | 12/2011 | Butterfield et al. |
| 8,078,983 | B2 | 12/2011 | Davis et al. |
| 8,082,018 | B2 | 12/2011 | Duchon et al. |
| 8,082,312 | B2 | 12/2011 | Chan et al. |
| 8,095,692 | B2 | 1/2012 | Mehta et al. |
| 8,126,730 | B2 | 2/2012 | Dicks et al. |
| 8,147,448 | B2 | 4/2012 | Sundar et al. |
| 8,149,131 | B2 | 4/2012 | Blomquist |
| 8,169,914 | B2 | 5/2012 | Bajpai |
| 8,171,094 | B2 | 5/2012 | Chan et al. |
| 8,172,798 | B2 | 5/2012 | Hungerford et al. |
| 8,185,322 | B2 | 5/2012 | Schroeder et al. |
| 8,195,478 | B2 | 6/2012 | Petersen et al. |
| 8,206,350 | B2 | 6/2012 | Mann et al. |
| 8,219,413 | B2 | 7/2012 | Martinez et al. |
| 8,231,578 | B2 | 7/2012 | Fathallah et al. |
| 8,234,128 | B2 | 7/2012 | Martucci et al. |
| 8,267,892 | B2 | 9/2012 | Spencer et al. |
| 8,271,106 | B2 | 9/2012 | Wehba et al. |
| 8,287,495 | B2 | 10/2012 | Michaud et al. |
| 8,291,337 | B2 | 10/2012 | Gannin et al. |
| 8,298,184 | B2 | 10/2012 | DiPerna et al. |
| 8,312,272 | B1 | 11/2012 | Serenyl et al. |
| 8,352,290 | B2 | 1/2013 | Bartz et al. |
| 8,359,338 | B2 | 1/2013 | Butterfield et al. |
| 8,380,536 | B2 | 2/2013 | Howard et al. |
| 8,387,112 | B1 | 2/2013 | Ranjan et al. |
| 8,394,077 | B2 | 3/2013 | Jacobson et al. |
| 8,398,592 | B2 | 3/2013 | Leibner-Druska |
| 8,403,908 | B2 | 3/2013 | Jacobson et al. |
| 8,435,206 | B2 | 5/2013 | Evans et al. |
| 8,449,523 | B2 | 5/2013 | Brukalo et al. |
| 8,452,953 | B2 | 5/2013 | Buck et al. |
| 8,453,645 | B2 | 6/2013 | Figueiredo et al. |
| 8,472,630 | B2 | 6/2013 | Konrad et al. |
| 8,480,648 | B2 | 7/2013 | Burnett et al. |
| 8,486,019 | B2 | 7/2013 | White et al. |
| 8,489,427 | B2 | 7/2013 | Simpson et al. |
| 8,494,879 | B2 | 7/2013 | Davis et al. |
| 8,504,179 | B2 | 8/2013 | Blomquist |
| 8,517,990 | B2 | 8/2013 | Teel et al. |
| 8,518,021 | B2 | 8/2013 | Stewart et al. |
| 8,543,416 | B2 | 9/2013 | Palmroos et al. |
| 8,551,038 | B2 | 10/2013 | Tsoukalis et al. |
| 8,560,345 | B2 | 10/2013 | Wehba et al. |
| 8,567,681 | B2 | 10/2013 | Borges et al. |
| 8,577,692 | B2 | 11/2013 | Silkaitis et al. |
| 8,579,884 | B2 | 11/2013 | Lanier et al. |
| 8,626,530 | B1 | 1/2014 | Tran et al. |
| 8,655,676 | B2 | 2/2014 | Wehba et al. |
| 8,660,860 | B2 | 2/2014 | Wehba et al. |
| 8,662,388 | B2 | 3/2014 | Belkin |
| 8,666,769 | B2 | 3/2014 | Butler et al. |
| 8,667,293 | B2 | 3/2014 | Birtwhistle et al. |
| 8,687,811 | B2 | 4/2014 | Nierzwick et al. |
| 8,700,421 | B2 | 4/2014 | Feng et al. |
| 8,731,960 | B2 | 5/2014 | Butler et al. |
| 8,768,719 | B2 | 7/2014 | Wehba et al. |
| 8,771,251 | B2 | 7/2014 | Ruchti et al. |
| 8,777,894 | B2 | 7/2014 | Butterfield et al. |
| 8,777,895 | B2 | 7/2014 | Hsu et al. |
| 8,799,012 | B2 | 8/2014 | Butler et al. |
| 8,876,793 | B2 | 11/2014 | Ledford et al. |
| 8,886,316 | B1 | 11/2014 | Juels |
| 8,922,330 | B2 | 12/2014 | Moberg et al. |
| 8,936,565 | B2 | 1/2015 | Chawla |
| 8,945,043 | B2 | 2/2015 | Lee et al. |
| 8,952,794 | B2 | 2/2015 | Blomquist et al. |
| 8,959,617 | B2 | 2/2015 | Newlin et al. |
| 8,998,100 | B2 | 4/2015 | Halbert et al. |

(56) References Cited

U.S. PATENT DOCUMENTS

| | | | |
|---|---|---|---|
| 9,026,370 B2 | 5/2015 | Rubalcaba et al. |
| 9,069,887 B2 | 6/2015 | Gupta et al. |
| 9,077,544 B2 | 7/2015 | Baker et al. |
| 9,089,642 B2 | 7/2015 | Murphy et al. |
| 9,114,217 B2 | 8/2015 | Sur et al. |
| 9,123,077 B2 | 9/2015 | Silkaitis et al. |
| 9,192,712 B2 | 11/2015 | DeBelser et al. |
| 9,240,002 B2 | 1/2016 | Hume et al. |
| 9,292,692 B2 | 3/2016 | Wallrabenstein |
| 9,302,035 B2 | 4/2016 | Marseille et al. |
| 9,313,154 B1 | 4/2016 | Son |
| 9,381,296 B2 | 7/2016 | Arrizza et al. |
| 9,393,362 B2 | 7/2016 | Cozmi et al. |
| 9,430,655 B1 | 8/2016 | Stockton et al. |
| 9,438,580 B2 | 9/2016 | Kupper |
| 9,483,615 B2 | 11/2016 | Roberts |
| 9,498,583 B2 | 11/2016 | Sur et al. |
| 9,539,383 B2 | 1/2017 | Kohlbrecher |
| 9,572,923 B2 | 2/2017 | Howard et al. |
| 9,594,875 B2 | 3/2017 | Arrizza et al. |
| 9,604,000 B2 | 3/2017 | Wehba et al. |
| 9,641,432 B2 | 5/2017 | Jha et al. |
| 9,649,431 B2 | 5/2017 | Gray et al. |
| 9,662,436 B2 | 5/2017 | Belkin et al. |
| 9,690,909 B2 | 6/2017 | Stewart et al. |
| 9,707,341 B2 | 7/2017 | Dumas, III et al. |
| 9,717,845 B2 | 8/2017 | Istoc |
| 9,724,470 B2 | 8/2017 | Day et al. |
| 9,764,082 B2 | 9/2017 | Day et al. |
| 9,886,550 B2 | 2/2018 | Lee et al. |
| 9,943,269 B2 | 4/2018 | Muhsin et al. |
| 9,967,739 B2 | 5/2018 | Proennecke et al. |
| 9,971,871 B2 | 5/2018 | Arrizza et al. |
| 9,995,611 B2 | 6/2018 | Ruchti et al. |
| 10,022,498 B2 | 7/2018 | Ruchti et al. |
| 10,042,986 B2 | 8/2018 | Ruchti et al. |
| 10,046,112 B2 | 8/2018 | Oruklu et al. |
| 10,166,328 B2 | 1/2019 | Oruklu et al. |
| 10,173,008 B2 | 1/2019 | Simpson et al. |
| 10,188,849 B2 | 1/2019 | Fangrow |
| 10,233,179 B2 | 3/2019 | Ng et al. |
| 10,238,799 B2 | 3/2019 | Kohlbrecher |
| 10,238,801 B2 | 3/2019 | Wehba et al. |
| 10,242,060 B2 | 3/2019 | Butler et al. |
| 10,300,194 B2 | 5/2019 | Day et al. |
| 10,311,972 B2 | 6/2019 | Kohlbrecher et al. |
| 10,314,974 B2 | 6/2019 | Day et al. |
| 10,333,843 B2 | 6/2019 | Jha et al. |
| 10,341,866 B1 | 7/2019 | Spencer et al. |
| 10,409,995 B1 | 9/2019 | Wasiq |
| 10,430,761 B2 | 10/2019 | Hume et al. |
| 10,434,246 B2 | 10/2019 | Silkaitis et al. |
| 10,438,001 B1 | 10/2019 | Hariprasad |
| 10,452,842 B2 | 10/2019 | Dhondse |
| 10,453,157 B2 | 10/2019 | Kamen et al. |
| 10,463,788 B2 | 11/2019 | Day |
| 10,516,536 B2 | 12/2019 | Rommel |
| 10,617,815 B2 | 4/2020 | Day et al. |
| 10,646,651 B2 | 5/2020 | Day et al. |
| 10,681,207 B1 | 6/2020 | Johnson et al. |
| 10,692,595 B2 | 6/2020 | Xavier et al. |
| 10,728,262 B1 | 7/2020 | Vaswani |
| 10,740,436 B2 * | 8/2020 | Moskal ................. A61M 5/172 |
| 10,741,280 B2 | 8/2020 | Xavier et al. |
| 10,757,219 B2 | 8/2020 | Moskal |
| 10,765,799 B2 | 9/2020 | Belkin et al. |
| 10,799,632 B2 | 10/2020 | Kohlbrecher |
| 10,812,380 B2 | 10/2020 | Jha et al. |
| 10,861,592 B2 | 12/2020 | Xavier et al. |
| 10,898,641 B2 | 1/2021 | Day et al. |
| 10,950,339 B2 | 3/2021 | Xavier et al. |
| 10,964,428 B2 | 3/2021 | Xavier et al. |
| 11,013,861 B2 | 5/2021 | Wehba et al. |
| 11,037,668 B2 | 6/2021 | Ruchti et al. |
| 11,052,193 B2 | 7/2021 | Day et al. |
| 11,139,058 B2 | 10/2021 | Xavier et al. |
| 11,151,290 B2 | 10/2021 | Karakoyunlu et al. |
| 11,152,108 B2 | 10/2021 | Xavier et al. |
| 11,152,109 B2 | 10/2021 | Xavier et al. |
| 11,152,110 B2 | 10/2021 | Xavier et al. |
| 11,194,810 B2 | 12/2021 | Butler et al. |
| 11,235,100 B2 | 2/2022 | Howard et al. |
| 11,289,183 B2 | 3/2022 | Kohlbrecher |
| 11,309,070 B2 | 4/2022 | Xavier et al. |
| 11,328,804 B2 | 5/2022 | Xavier et al. |
| 11,328,805 B2 | 5/2022 | Xavier et al. |
| 11,373,753 B2 | 6/2022 | Xavier et al. |
| 11,437,132 B2 | 9/2022 | Xavier et al. |
| 11,470,000 B2 | 10/2022 | Jha et al. |
| 11,483,402 B2 | 10/2022 | Xavier et al. |
| 11,483,403 B2 | 10/2022 | Xavier et al. |
| 11,501,877 B2 | 11/2022 | Kohlbrecher et al. |
| 11,571,508 B2 | 2/2023 | Jacobson et al. |
| 11,574,721 B2 | 2/2023 | Kohlbrecher |
| 11,574,737 B2 | 2/2023 | Dharwad et al. |
| 11,587,669 B2 | 2/2023 | Xavier et al. |
| 11,590,057 B2 | 2/2023 | Tagliamento et al. |
| 11,594,326 B2 | 2/2023 | Xavier et al. |
| 11,605,468 B2 | 3/2023 | Jacobson et al. |
| 11,626,205 B2 | 4/2023 | Arrizza et al. |
| 11,628,246 B2 | 4/2023 | Day et al. |
| 11,628,254 B2 | 4/2023 | Day et al. |
| 11,654,237 B2 | 5/2023 | Wehba et al. |
| 11,670,416 B2 | 6/2023 | Xavier et al. |
| 11,763,927 B2 | 9/2023 | Ruchti et al. |
| 11,783,935 B2 | 10/2023 | Xavier et al. |
| 11,881,297 B2 | 1/2024 | Xavier et al. |
| 11,923,076 B2 | 3/2024 | Xavier et al. |
| 11,986,623 B2 | 5/2024 | Jacobson et al. |
| 11,996,188 B2 | 5/2024 | Arrizza et al. |
| 12,002,562 B2 | 6/2024 | Kohlbrecher |
| 12,036,390 B2 | 7/2024 | Wehba et al. |
| 12,040,068 B2 | 7/2024 | Xavier et al. |
| 12,042,623 B2 | 7/2024 | Day et al. |
| 12,042,631 B2 | 7/2024 | Day et al. |
| 12,046,361 B2 | 7/2024 | Xavier et al. |
| 12,047,292 B2 | 7/2024 | Jha et al. |
| 12,097,351 B2 | 9/2024 | Belkin et al. |
| 12,130,910 B2 | 10/2024 | Vivek et al. |
| 12,142,370 B2 | 11/2024 | Xavier et al. |
| 12,205,702 B2 | 1/2025 | Xavier et al. |
| 2001/0016056 A1 | 8/2001 | Westphal et al. |
| 2001/0029178 A1 | 10/2001 | Criss et al. |
| 2001/0031944 A1 | 10/2001 | Peterson et al. |
| 2001/0032099 A1 | 10/2001 | Joao |
| 2001/0037060 A1 | 11/2001 | Thompson et al. |
| 2001/0044731 A1 | 11/2001 | Coffman et al. |
| 2001/0048027 A1 | 12/2001 | Walsh |
| 2001/0051787 A1 | 12/2001 | Haller et al. |
| 2001/0056358 A1 | 12/2001 | Dulong et al. |
| 2002/0010595 A1 | 1/2002 | Kapp |
| 2002/0013551 A1 | 1/2002 | Zaitsu et al. |
| 2002/0013723 A1 | 1/2002 | Mise |
| 2002/0015018 A1 | 2/2002 | Shimazu et al. |
| 2002/0019584 A1 | 2/2002 | Schulze et al. |
| 2002/0021700 A1 | 2/2002 | Hata et al. |
| 2002/0026103 A1 | 2/2002 | Norris et al. |
| 2002/0029776 A1 | 3/2002 | Blomquist |
| 2002/0032583 A1 | 3/2002 | Joao |
| 2002/0040208 A1 | 4/2002 | Flaherty et al. |
| 2002/0040282 A1 | 4/2002 | Bailey et al. |
| 2002/0044043 A1 | 4/2002 | Chaco et al. |
| 2002/0044059 A1 | 4/2002 | Reeder et al. |
| 2002/0082728 A1 | 6/2002 | Mueller et al. |
| 2002/0087115 A1 | 7/2002 | Hartlaub |
| 2002/0087116 A1 | 7/2002 | Hartlaub |
| 2002/0095486 A1 | 7/2002 | Bahl |
| 2002/0103675 A1 | 8/2002 | Vanelli |
| 2002/0123905 A1 | 9/2002 | Goodroe et al. |
| 2002/0143580 A1 | 10/2002 | Bristol et al. |
| 2002/0152239 A1 | 10/2002 | Bautista-Lloyd et al. |
| 2002/0154600 A1 | 10/2002 | Ido et al. |
| 2002/0173702 A1 | 11/2002 | Lebel et al. |
| 2002/0173875 A1 | 11/2002 | Wallace et al. |

(56) References Cited

U.S. PATENT DOCUMENTS

| | | |
|---|---|---|
| 2002/0193679 A1 | 12/2002 | Malave et al. |
| 2002/0194329 A1 | 12/2002 | Alling |
| 2003/0009244 A1 | 1/2003 | Engleson |
| 2003/0013959 A1 | 1/2003 | Grunwald et al. |
| 2003/0014222 A1 | 1/2003 | Klass et al. |
| 2003/0014817 A1 | 1/2003 | Gallant et al. |
| 2003/0025602 A1 | 2/2003 | Medema et al. |
| 2003/0028082 A1 | 2/2003 | Thompson |
| 2003/0036683 A1 | 2/2003 | Kehr et al. |
| 2003/0036744 A1 | 2/2003 | Struys et al. |
| 2003/0047126 A1 | 3/2003 | Tomaschko |
| 2003/0047600 A1 | 3/2003 | Nakanishi et al. |
| 2003/0050621 A1 | 3/2003 | Lebel et al. |
| 2003/0059750 A1 | 3/2003 | Bindler et al. |
| 2003/0060688 A1 | 3/2003 | Ciarniello et al. |
| 2003/0069963 A1 | 4/2003 | Jayant et al. |
| 2003/0079746 A1 | 5/2003 | Hickle |
| 2003/0097529 A1 | 5/2003 | Arimilli et al. |
| 2003/0104982 A1 | 6/2003 | Wittmann et al. |
| 2003/0105389 A1 | 6/2003 | Noonan et al. |
| 2003/0106553 A1 | 6/2003 | Vanderveen |
| 2003/0115358 A1 | 6/2003 | Yun |
| 2003/0120384 A1 | 6/2003 | Haitin et al. |
| 2003/0125662 A1 | 7/2003 | Bui |
| 2003/0130616 A1 | 7/2003 | Steil |
| 2003/0135087 A1 | 7/2003 | Hickle et al. |
| 2003/0139701 A1 | 7/2003 | White et al. |
| 2003/0140928 A1 | 7/2003 | Bui et al. |
| 2003/0140929 A1 | 7/2003 | Wilkes et al. |
| 2003/0141981 A1 | 7/2003 | Bui et al. |
| 2003/0143746 A1 | 7/2003 | Sage, Jr. |
| 2003/0144878 A1 | 7/2003 | Wilkes et al. |
| 2003/0158749 A1 | 8/2003 | Olchanski et al. |
| 2003/0187338 A1 | 10/2003 | Say et al. |
| 2003/0200116 A1 | 10/2003 | Forrester |
| 2003/0204416 A1 | 10/2003 | Acharya |
| 2003/0204781 A1 | 10/2003 | Peebles et al. |
| 2003/0212364 A1 | 11/2003 | Mann et al. |
| 2003/0212379 A1 | 11/2003 | Bylund et al. |
| 2003/0212821 A1 | 11/2003 | Gillies et al. |
| 2003/0216831 A1 | 11/2003 | Hart et al. |
| 2003/0217962 A1 | 11/2003 | Childers et al. |
| 2004/0008123 A1 | 1/2004 | Carrender et al. |
| 2004/0010786 A1 | 1/2004 | Cool et al. |
| 2004/0015132 A1 | 1/2004 | Brown |
| 2004/0019464 A1 | 1/2004 | Martucci et al. |
| 2004/0019607 A1 | 1/2004 | Moubayed et al. |
| 2004/0030323 A1 | 2/2004 | Ullestad et al. |
| 2004/0039257 A1 | 2/2004 | Hickle |
| 2004/0057226 A1 | 3/2004 | Berthou et al. |
| 2004/0064341 A1 | 4/2004 | Langan et al. |
| 2004/0064342 A1 | 4/2004 | Browne et al. |
| 2004/0064435 A1 | 4/2004 | Moubayed et al. |
| 2004/0073161 A1 | 4/2004 | Tachibana |
| 2004/0073811 A1 | 4/2004 | Sanin |
| 2004/0077934 A1 | 4/2004 | Massad |
| 2004/0078231 A1 | 4/2004 | Wilkes et al. |
| 2004/0078236 A1 | 4/2004 | Stoodley et al. |
| 2004/0085186 A1 | 5/2004 | Eveland et al. |
| 2004/0104271 A1 | 6/2004 | Martucci et al. |
| 2004/0122530 A1 | 6/2004 | Hansen |
| 2004/0128162 A1 | 7/2004 | Schlotterbeck et al. |
| 2004/0128163 A1 | 7/2004 | Goodman et al. |
| 2004/0133441 A1 | 7/2004 | Brady et al. |
| 2004/0139004 A1 | 7/2004 | Cohen et al. |
| 2004/0145480 A1 | 7/2004 | Despotis |
| 2004/0147034 A1 | 7/2004 | Gore et al. |
| 2004/0167464 A1 | 8/2004 | Ireland et al. |
| 2004/0167465 A1 | 8/2004 | Kohler |
| 2004/0167804 A1 | 8/2004 | Simpson |
| 2004/0172222 A1 | 9/2004 | Simpson et al. |
| 2004/0172283 A1 | 9/2004 | Vanderveen |
| 2004/0172301 A1 | 9/2004 | Mihai et al. |
| 2004/0172302 A1 | 9/2004 | Martucci et al. |
| 2004/0176667 A1 | 9/2004 | Mihai et al. |
| 2004/0176980 A1 | 9/2004 | Bulitta et al. |
| 2004/0176984 A1 | 9/2004 | White et al. |
| 2004/0181314 A1 | 9/2004 | Zaleski |
| 2004/0189708 A1 | 9/2004 | Larcheveque et al. |
| 2004/0193325 A1 | 9/2004 | Bonderud |
| 2004/0193328 A1 | 9/2004 | Butterfield et al. |
| 2004/0193453 A1 | 9/2004 | Butterfield et al. |
| 2004/0204673 A1 | 10/2004 | Flaherty et al. |
| 2004/0215278 A1 | 10/2004 | Stegink et al. |
| 2004/0220517 A1 | 11/2004 | Starkweather et al. |
| 2004/0225252 A1 | 11/2004 | Gillespie et al. |
| 2004/0236240 A1 | 11/2004 | Kraus et al. |
| 2004/0243438 A1 | 12/2004 | Mintz |
| 2004/0254434 A1 | 12/2004 | Goodnow et al. |
| 2005/0010269 A1 | 1/2005 | Lebel et al. |
| 2005/0020886 A1 | 1/2005 | Hutchinson et al. |
| 2005/0021006 A1 | 1/2005 | Tonnies |
| 2005/0027560 A1 | 2/2005 | Cook |
| 2005/0027567 A1 | 2/2005 | Taha |
| 2005/0038311 A1 | 2/2005 | Kuth |
| 2005/0038669 A1 | 2/2005 | Sachdeva et al. |
| 2005/0038680 A1 | 2/2005 | McMahon |
| 2005/0040226 A1 | 2/2005 | Al-Sheikh |
| 2005/0043620 A1 | 2/2005 | Fallows et al. |
| 2005/0049910 A1 | 3/2005 | Lancaster et al. |
| 2005/0055242 A1 | 3/2005 | Bello et al. |
| 2005/0055244 A1 | 3/2005 | Mullan et al. |
| 2005/0065465 A1 | 3/2005 | Lebel et al. |
| 2005/0065817 A1 | 3/2005 | Mihai et al. |
| 2005/0075544 A1 | 4/2005 | Shapiro et al. |
| 2005/0080801 A1 | 4/2005 | Kothandaraman et al. |
| 2005/0086071 A1 | 4/2005 | Fox et al. |
| 2005/0086072 A1 | 4/2005 | Fox |
| 2005/0088704 A1 | 4/2005 | Vaschillo et al. |
| 2005/0090808 A1 | 4/2005 | Malave et al. |
| 2005/0099624 A1 | 5/2005 | Staehr |
| 2005/0102162 A1 | 5/2005 | Blumenfeld |
| 2005/0102165 A1 | 5/2005 | Oshita et al. |
| 2005/0102167 A1 | 5/2005 | Kapoor |
| 2005/0102669 A1 | 5/2005 | Marney et al. |
| 2005/0107923 A1 | 5/2005 | Vanderveen |
| 2005/0108057 A1 | 5/2005 | Cohen et al. |
| 2005/0117529 A1 | 6/2005 | Ramos-Escano |
| 2005/0119788 A1 | 6/2005 | Engleson et al. |
| 2005/0119914 A1 | 6/2005 | Batch |
| 2005/0131739 A1 | 6/2005 | Rabinowitz et al. |
| 2005/0135306 A1 | 6/2005 | McAllen et al. |
| 2005/0137522 A1 | 6/2005 | Aoki |
| 2005/0137573 A1 | 6/2005 | McLaughlin |
| 2005/0138428 A1 | 6/2005 | McAllen et al. |
| 2005/0144043 A1 | 6/2005 | Holland et al. |
| 2005/0154769 A1 | 7/2005 | Eckart et al. |
| 2005/0160057 A1 | 7/2005 | Wefers et al. |
| 2005/0171503 A1 | 8/2005 | Van Den Berghe et al. |
| 2005/0171815 A1 | 8/2005 | Vanderveen |
| 2005/0177096 A1 | 8/2005 | Bollish et al. |
| 2005/0177395 A1 | 8/2005 | Blomquist |
| 2005/0182306 A1 | 8/2005 | Sloan |
| 2005/0182355 A1 | 8/2005 | Bui |
| 2005/0187950 A1 | 8/2005 | Parker |
| 2005/0192557 A1 | 9/2005 | Brauker et al. |
| 2005/0197554 A1 | 9/2005 | Polcha |
| 2005/0197621 A1 | 9/2005 | Poulsen et al. |
| 2005/0210037 A1 | 9/2005 | Wefers et al. |
| 2005/0216479 A1 | 9/2005 | Wefers et al. |
| 2005/0216480 A1 | 9/2005 | Wefers et al. |
| 2005/0223045 A1 | 10/2005 | Funahashi et al. |
| 2005/0224083 A1 | 10/2005 | Crass |
| 2005/0234746 A1 | 10/2005 | Funahashi |
| 2005/0240305 A1 | 10/2005 | Bogash et al. |
| 2005/0246416 A1 | 11/2005 | Blomquist |
| 2005/0251418 A1 | 11/2005 | Fox et al. |
| 2005/0261660 A1 | 11/2005 | Choi |
| 2005/0273059 A1 | 12/2005 | Mernoe et al. |
| 2005/0273367 A1 | 12/2005 | Nourie et al. |
| 2005/0277873 A1 | 12/2005 | Stewart et al. |
| 2005/0277890 A1 | 12/2005 | Stewart et al. |
| 2005/0277911 A1 | 12/2005 | Stewart et al. |
| 2005/0278194 A1 | 12/2005 | Holland et al. |

(56) References Cited

U.S. PATENT DOCUMENTS

| | | |
|---|---|---|
| 2006/0004772 A1 | 1/2006 | Hagan et al. |
| 2006/0009727 A1 | 1/2006 | O'Mahony et al. |
| 2006/0009734 A1 | 1/2006 | Martin |
| 2006/0010098 A1 | 1/2006 | Goodnow et al. |
| 2006/0042139 A1 | 3/2006 | Mendes |
| 2006/0047270 A1 | 3/2006 | Shelton |
| 2006/0053036 A1 | 3/2006 | Coffman et al. |
| 2006/0064020 A1 | 3/2006 | Burnes et al. |
| 2006/0074633 A1 | 4/2006 | Mahesh et al. |
| 2006/0074920 A1 | 4/2006 | Wefers et al. |
| 2006/0079831 A1 | 4/2006 | Gilbert |
| 2006/0089539 A1 | 4/2006 | Miodownik et al. |
| 2006/0089854 A1 | 4/2006 | Holland et al. |
| 2006/0089855 A1 | 4/2006 | Holland et al. |
| 2006/0100746 A1 | 5/2006 | Leibner-Druska |
| 2006/0100907 A1 | 5/2006 | Holland et al. |
| 2006/0106649 A1 | 5/2006 | Eggers et al. |
| 2006/0111943 A1 | 5/2006 | Wu |
| 2006/0116904 A1 | 6/2006 | Brem |
| 2006/0116907 A1 | 6/2006 | Rhodes et al. |
| 2006/0122481 A1 | 6/2006 | Sievenpiper et al. |
| 2006/0122867 A1 | 6/2006 | Eggers et al. |
| 2006/0129140 A1 | 6/2006 | Todd et al. |
| 2006/0129429 A1 | 6/2006 | Moubayed et al. |
| 2006/0129434 A1 | 6/2006 | Smitherman et al. |
| 2006/0129435 A1 | 6/2006 | Smitherman et al. |
| 2006/0136266 A1 | 6/2006 | Tarassenko et al. |
| 2006/0136271 A1 | 6/2006 | Eggers et al. |
| 2006/0143051 A1 | 6/2006 | Eggers et al. |
| 2006/0173260 A1 | 8/2006 | Gaoni et al. |
| 2006/0173406 A1 | 8/2006 | Hayes et al. |
| 2006/0173715 A1 | 8/2006 | Wang et al. |
| 2006/0173927 A1 | 8/2006 | Beyer et al. |
| 2006/0190302 A1 | 8/2006 | Eggers et al. |
| 2006/0195022 A1 | 8/2006 | Trepagnier et al. |
| 2006/0200007 A1 | 9/2006 | Brockway et al. |
| 2006/0200369 A1 | 9/2006 | Batch et al. |
| 2006/0211404 A1 | 9/2006 | Cromp et al. |
| 2006/0224141 A1 | 10/2006 | Rush et al. |
| 2006/0229918 A1 | 10/2006 | Fotsch et al. |
| 2006/0236373 A1 | 10/2006 | Graves et al. |
| 2006/0247606 A1 | 11/2006 | Batch |
| 2006/0253554 A1 | 11/2006 | Uwais |
| 2006/0258985 A1 | 11/2006 | Russell |
| 2006/0259327 A1 | 11/2006 | Hoag |
| 2006/0264895 A1 | 11/2006 | Flanders |
| 2006/0265246 A1 | 11/2006 | Hoag |
| 2006/0267753 A1 | 11/2006 | Hussey et al. |
| 2006/0268710 A1 | 11/2006 | Appanna et al. |
| 2006/0270971 A1 | 11/2006 | Gelfand et al. |
| 2006/0277206 A1 | 12/2006 | Bailey et al. |
| 2006/0287885 A1 | 12/2006 | Frick |
| 2007/0015972 A1 | 1/2007 | Wang et al. |
| 2007/0016443 A1 | 1/2007 | Wachman et al. |
| 2007/0021715 A1 | 1/2007 | Kohlbrenner et al. |
| 2007/0027506 A1 | 2/2007 | Stender et al. |
| 2007/0060796 A1 | 3/2007 | Kim |
| 2007/0060870 A1 | 3/2007 | Tolle et al. |
| 2007/0060871 A1 | 3/2007 | Istoc |
| 2007/0061393 A1 | 3/2007 | Moore |
| 2007/0065363 A1 | 3/2007 | Dalal et al. |
| 2007/0073419 A1 | 3/2007 | Sesay |
| 2007/0073822 A1 | 3/2007 | Bennett et al. |
| 2007/0078314 A1 | 4/2007 | Grounsell |
| 2007/0083870 A1 | 4/2007 | Kanakogi |
| 2007/0088333 A1 | 4/2007 | Levin et al. |
| 2007/0093786 A1 | 4/2007 | Goldsmith et al. |
| 2007/0100665 A1 | 5/2007 | Brown |
| 2007/0100667 A1 | 5/2007 | Bardy |
| 2007/0106126 A1 | 5/2007 | Mannheimer et al. |
| 2007/0112298 A1 | 5/2007 | Mueller et al. |
| 2007/0116037 A1 | 5/2007 | Moore |
| 2007/0118405 A1 | 5/2007 | Campbell et al. |
| 2007/0135866 A1 | 6/2007 | Baker et al. |
| 2007/0136098 A1 | 6/2007 | Smythe et al. |
| 2007/0142822 A1 | 6/2007 | Remde |
| 2007/0156282 A1 | 7/2007 | Dunn |
| 2007/0156452 A1 | 7/2007 | Batch |
| 2007/0169008 A1 | 7/2007 | Varanasi et al. |
| 2007/0179448 A1 | 8/2007 | Lim et al. |
| 2007/0186923 A1 | 8/2007 | Poutiatine et al. |
| 2007/0191817 A1 | 8/2007 | Martin |
| 2007/0191973 A1 | 8/2007 | Holzbauer et al. |
| 2007/0213598 A1* | 9/2007 | Howard .............. G16H 40/67<br>600/300 |
| 2007/0213657 A1 | 9/2007 | Jennewine et al. |
| 2007/0213684 A1 | 9/2007 | Hickle et al. |
| 2007/0214003 A1 | 9/2007 | Holland et al. |
| 2007/0215545 A1 | 9/2007 | Bissler et al. |
| 2007/0232867 A1 | 10/2007 | Hansmann |
| 2007/0233035 A1 | 10/2007 | Wehba et al. |
| 2007/0233049 A1 | 10/2007 | Wehba et al. |
| 2007/0233206 A1 | 10/2007 | Frikart |
| 2007/0233520 A1 | 10/2007 | Wehba et al. |
| 2007/0240215 A1 | 10/2007 | Flores |
| 2007/0251835 A1 | 11/2007 | Mehta et al. |
| 2007/0253021 A1 | 11/2007 | Mehta et al. |
| 2007/0254593 A1 | 11/2007 | Jollota et al. |
| 2007/0255125 A1 | 11/2007 | Moberg et al. |
| 2007/0257788 A1 | 11/2007 | Carlson |
| 2007/0258395 A1 | 11/2007 | Jollota et al. |
| 2007/0299687 A1 | 12/2007 | Palmer et al. |
| 2007/0299695 A1 | 12/2007 | Jung et al. |
| 2008/0001771 A1 | 1/2008 | Faoro et al. |
| 2008/0004904 A1 | 1/2008 | Tran |
| 2008/0009684 A1 | 1/2008 | Corsetti et al. |
| 2008/0033361 A1 | 2/2008 | Evans et al. |
| 2008/0033966 A1 | 2/2008 | Wahl |
| 2008/0034323 A1 | 2/2008 | Blomquist |
| 2008/0041942 A1 | 2/2008 | Aissa |
| 2008/0052704 A1 | 2/2008 | Wysocki |
| 2008/0065007 A1 | 3/2008 | Peterson et al. |
| 2008/0065417 A1 | 3/2008 | Jung et al. |
| 2008/0071217 A1 | 3/2008 | Moubayed et al. |
| 2008/0071251 A1 | 3/2008 | Moubayed et al. |
| 2008/0086088 A1 | 4/2008 | Malcolm |
| 2008/0091466 A1 | 4/2008 | Butler et al. |
| 2008/0095339 A1 | 4/2008 | Elliott |
| 2008/0097289 A1 | 4/2008 | Steil et al. |
| 2008/0097552 A1 | 4/2008 | Dicks et al. |
| 2008/0126969 A1 | 5/2008 | Blomquist |
| 2008/0133265 A1* | 6/2008 | Silkaitis .............. G16H 40/67<br>705/2 |
| 2008/0139907 A1 | 6/2008 | Rao et al. |
| 2008/0148047 A1 | 6/2008 | Appenzeller et al. |
| 2008/0149117 A1 | 6/2008 | Raghuram |
| 2008/0154177 A1 | 6/2008 | Moubayed et al. |
| 2008/0172337 A1 | 7/2008 | Banfield et al. |
| 2008/0184219 A1 | 7/2008 | Matsumoto |
| 2008/0188796 A1 | 8/2008 | Steil et al. |
| 2008/0214919 A1 | 9/2008 | Harmon et al. |
| 2008/0246748 A1 | 10/2008 | Cassidy et al. |
| 2008/0256305 A1 | 10/2008 | Kwon |
| 2008/0259926 A1 | 10/2008 | Tavares et al. |
| 2008/0262469 A1 | 10/2008 | Bristol et al. |
| 2008/0269714 A1 | 10/2008 | Mastrototaro et al. |
| 2008/0269723 A1 | 10/2008 | Mastrototaro et al. |
| 2008/0275384 A1 | 11/2008 | Mastrototaro et al. |
| 2008/0300572 A1 | 12/2008 | Rankers et al. |
| 2008/0301298 A1 | 12/2008 | Bernardi et al. |
| 2008/0320387 A1 | 12/2008 | Sasaki et al. |
| 2008/0320466 A1 | 12/2008 | Dias |
| 2009/0003554 A1 | 1/2009 | Katis et al. |
| 2009/0005703 A1 | 1/2009 | Fasciano |
| 2009/0005728 A1 | 1/2009 | Weinert et al. |
| 2009/0006061 A1 | 1/2009 | Thukral et al. |
| 2009/0006129 A1 | 1/2009 | Thukral |
| 2009/0006133 A1 | 1/2009 | Weinert |
| 2009/0018495 A1 | 1/2009 | Panduro |
| 2009/0036750 A1 | 2/2009 | Weinstein et al. |
| 2009/0051560 A1 | 2/2009 | Manning et al. |
| 2009/0054743 A1 | 2/2009 | Stewart |
| 2009/0054754 A1 | 2/2009 | McMahon et al. |
| 2009/0057399 A1 | 3/2009 | Sajkowsky |

(56)  References Cited

U.S. PATENT DOCUMENTS

| | | |
|---|---|---|
| 2009/0063187 A1 | 3/2009 | Johnson et al. |
| 2009/0069785 A1 | 3/2009 | Miller et al. |
| 2009/0099866 A1 | 4/2009 | Newman |
| 2009/0099867 A1 | 4/2009 | Newman |
| 2009/0135196 A1 | 5/2009 | Holland et al. |
| 2009/0143662 A1 | 6/2009 | Estes et al. |
| 2009/0149743 A1 | 6/2009 | Barron et al. |
| 2009/0150174 A1 | 6/2009 | Buck et al. |
| 2009/0150439 A1 | 6/2009 | Gejdos et al. |
| 2009/0150878 A1 | 6/2009 | Pathak et al. |
| 2009/0156991 A1 | 6/2009 | Roberts |
| 2009/0157695 A1 | 6/2009 | Roberts |
| 2009/0158274 A1 | 6/2009 | Roberts |
| 2009/0177146 A1 | 7/2009 | Nesbitt et al. |
| 2009/0177769 A1 | 7/2009 | Roberts |
| 2009/0177992 A1 | 7/2009 | Rubalcaba et al. |
| 2009/0183147 A1 | 7/2009 | Davis et al. |
| 2009/0209938 A1 | 8/2009 | Aalto-Setala |
| 2009/0210250 A1 | 8/2009 | Prax et al. |
| 2009/0221890 A1 | 9/2009 | Saffer et al. |
| 2009/0231249 A1 | 9/2009 | Wang et al. |
| 2009/0270833 A1 | 10/2009 | DeBelser |
| 2009/0275886 A1 | 11/2009 | Blomquist et al. |
| 2009/0275896 A1 | 11/2009 | Kamen et al. |
| 2009/0284691 A1 | 11/2009 | Marhefka et al. |
| 2009/0292340 A1 | 11/2009 | Mass et al. |
| 2009/0306573 A1 | 12/2009 | Gagner et al. |
| 2009/0326340 A1 | 12/2009 | Wang |
| 2009/0326516 A1 | 12/2009 | Bangera et al. |
| 2010/0008377 A1 | 1/2010 | Hasti et al. |
| 2010/0022988 A1 | 1/2010 | Wochner |
| 2010/0036310 A1 | 2/2010 | Hillman |
| 2010/0056992 A1 | 3/2010 | Hayter |
| 2010/0083060 A1 | 4/2010 | Rahman |
| 2010/0095229 A1 | 4/2010 | Dixon et al. |
| 2010/0121170 A1 | 5/2010 | Rule |
| 2010/0121246 A1 | 5/2010 | Peters et al. |
| 2010/0121415 A1 | 5/2010 | Skelton et al. |
| 2010/0121654 A1 | 5/2010 | Portnoy et al. |
| 2010/0121752 A1 | 5/2010 | Banigan et al. |
| 2010/0130933 A1 | 5/2010 | Holland et al. |
| 2010/0131434 A1 | 5/2010 | Magent et al. |
| 2010/0138523 A1 | 6/2010 | Umess et al. |
| 2010/0146137 A1 | 6/2010 | Wu et al. |
| 2010/0156633 A1 | 6/2010 | Buck et al. |
| 2010/0160854 A1 | 6/2010 | Gauthier |
| 2010/0160860 A1 | 6/2010 | Celentano et al. |
| 2010/0174266 A1 | 7/2010 | Estes |
| 2010/0191525 A1 | 7/2010 | Rabenko et al. |
| 2010/0198034 A1 | 8/2010 | Thomas et al. |
| 2010/0198196 A1 | 8/2010 | Wei |
| 2010/0200506 A1 | 8/2010 | Ware et al. |
| 2010/0209268 A1 | 8/2010 | Davis |
| 2010/0212675 A1 | 8/2010 | Walling et al. |
| 2010/0217621 A1 | 8/2010 | Schoenberg |
| 2010/0234708 A1 | 9/2010 | Buck et al. |
| 2010/0250732 A1 | 9/2010 | Bucknell |
| 2010/0271479 A1 | 10/2010 | Heydlauf |
| 2010/0273738 A1 | 10/2010 | Valcke et al. |
| 2010/0274218 A1 | 10/2010 | Yodfat et al. |
| 2010/0280486 A1 | 11/2010 | Khair et al. |
| 2010/0292634 A1 | 11/2010 | Kircher |
| 2010/0298765 A1 | 11/2010 | Budiman et al. |
| 2010/0318025 A1 | 12/2010 | John |
| 2011/0001605 A1 | 1/2011 | Kiani et al. |
| 2011/0021898 A1 | 1/2011 | Wei et al. |
| 2011/0028885 A1 | 2/2011 | Eggers et al. |
| 2011/0040158 A1 | 2/2011 | Katz et al. |
| 2011/0060758 A1 | 3/2011 | Schlotterbeck et al. |
| 2011/0071844 A1 | 3/2011 | Cannon et al. |
| 2011/0072379 A1 | 3/2011 | Gannon |
| 2011/0078253 A1 | 3/2011 | Chan et al. |
| 2011/0078608 A1 | 3/2011 | Gannon et al. |
| 2011/0093284 A1 | 4/2011 | Dicks et al. |
| 2011/0099313 A1 | 4/2011 | Bolanowski |
| 2011/0106318 A1* | 5/2011 | Ledford ............. A61M 5/1452 |
| | | 700/282 |
| 2011/0125095 A1 | 5/2011 | Lebel et al. |
| 2011/0138185 A1 | 6/2011 | Ju et al. |
| 2011/0166628 A1 | 7/2011 | Jain |
| 2011/0175728 A1 | 7/2011 | Baker, Jr. |
| 2011/0178462 A1 | 7/2011 | Moberg et al. |
| 2011/0185010 A1 | 7/2011 | Shatsky et al. |
| 2011/0196748 A1 | 8/2011 | Caron et al. |
| 2011/0231216 A1 | 9/2011 | Fyke et al. |
| 2011/0252230 A1 | 10/2011 | Segre et al. |
| 2011/0257496 A1 | 10/2011 | Terashima et al. |
| 2011/0257798 A1 | 10/2011 | Ali et al. |
| 2011/0259954 A1 | 10/2011 | Bartz et al. |
| 2011/0264043 A1 | 10/2011 | Kotnick et al. |
| 2011/0264044 A1 | 10/2011 | Bartz et al. |
| 2011/0266221 A1 | 11/2011 | Ware et al. |
| 2011/0270045 A1 | 11/2011 | Lebel et al. |
| 2011/0275904 A1 | 11/2011 | Lebel et al. |
| 2011/0286457 A1 | 11/2011 | Ee |
| 2011/0289162 A1 | 11/2011 | Furlong |
| 2011/0289314 A1 | 11/2011 | Whitcomb |
| 2011/0289497 A1 | 11/2011 | Kiaie et al. |
| 2011/0295196 A1 | 12/2011 | Chazot et al. |
| 2011/0295341 A1 | 12/2011 | Estes et al. |
| 2011/0296051 A1 | 12/2011 | Vange |
| 2011/0296411 A1 | 12/2011 | Tang et al. |
| 2011/0313789 A1 | 12/2011 | Karmen et al. |
| 2011/0319813 A1 | 12/2011 | Kamen et al. |
| 2011/0320049 A1 | 12/2011 | Chossat et al. |
| 2012/0005680 A1 | 1/2012 | Dolby et al. |
| 2012/0011253 A1 | 1/2012 | Friedman et al. |
| 2012/0016305 A1 | 1/2012 | Jollota |
| 2012/0029941 A1 | 2/2012 | Malave et al. |
| 2012/0036102 A1 | 2/2012 | Fletcher et al. |
| 2012/0036550 A1 | 2/2012 | Rodriguez |
| 2012/0065990 A1 | 3/2012 | Howard et al. |
| 2012/0066501 A1 | 3/2012 | Xiong |
| 2012/0070045 A1 | 3/2012 | Vesper et al. |
| 2012/0079084 A1 | 3/2012 | Forssell et al. |
| 2012/0095437 A1 | 4/2012 | Hemmerling |
| 2012/0112903 A1 | 5/2012 | Kaib et al. |
| 2012/0130198 A1 | 5/2012 | Beaule |
| 2012/0143116 A1 | 6/2012 | Ware et al. |
| 2012/0150556 A1 | 6/2012 | Galasso et al. |
| 2012/0157920 A1 | 6/2012 | Flachbart et al. |
| 2012/0179135 A1 | 7/2012 | Rinehart et al. |
| 2012/0179136 A1 | 7/2012 | Rinehart et al. |
| 2012/0185267 A1 | 7/2012 | Kamen et al. |
| 2012/0203177 A1 | 8/2012 | Lanier |
| 2012/0245554 A1 | 9/2012 | Kawamura |
| 2012/0259978 A1 | 10/2012 | Petersen et al. |
| 2012/0260012 A1 | 10/2012 | Gao-Saari et al. |
| 2012/0277716 A1 | 11/2012 | Ali et al. |
| 2012/0283630 A1 | 11/2012 | Lee et al. |
| 2012/0284734 A1 | 11/2012 | McQuaid et al. |
| 2012/0323212 A1 | 12/2012 | Murphy |
| 2012/0330380 A1 | 12/2012 | Corndorf |
| 2013/0006666 A1 | 1/2013 | Schneider |
| 2013/0006702 A1 | 1/2013 | Wu |
| 2013/0012877 A1 | 1/2013 | Debelser et al. |
| 2013/0012879 A1 | 1/2013 | Debelser et al. |
| 2013/0012880 A1 | 1/2013 | Blomquist |
| 2013/0015980 A1 | 1/2013 | Evans et al. |
| 2013/0036403 A1 | 2/2013 | Geist |
| 2013/0036412 A1 | 2/2013 | Birtwhistle et al. |
| 2013/0047113 A1 | 2/2013 | Hume et al. |
| 2013/0066265 A1 | 3/2013 | Grant |
| 2013/0072872 A1 | 3/2013 | Yodfat et al. |
| 2013/0091350 A1 | 4/2013 | Gluck |
| 2013/0096444 A1 | 4/2013 | Condurso et al. |
| 2013/0096648 A1 | 4/2013 | Benson |
| 2013/0102963 A1 | 4/2013 | Marsh et al. |
| 2013/0104120 A1 | 4/2013 | Arrizza et al. |
| 2013/0114594 A1 | 5/2013 | Van Zijst |
| 2013/0116578 A1 | 5/2013 | An |
| 2013/0133083 A1 | 5/2013 | Kurumai |
| 2013/0138452 A1 | 5/2013 | Cork et al. |
| 2013/0144206 A1 | 6/2013 | Lee et al. |

(56) References Cited

U.S. PATENT DOCUMENTS

| | | |
|---|---|---|
| 2013/0150824 A1 | 6/2013 | Estes et al. |
| 2013/0167245 A1 | 6/2013 | Birtwhistle et al. |
| 2013/0173473 A1 | 7/2013 | Birtwhistle et al. |
| 2013/0191770 A1 | 7/2013 | Bartz et al. |
| 2013/0204188 A1 | 8/2013 | Kamen et al. |
| 2013/0218080 A1 | 8/2013 | Peterfreund et al. |
| 2013/0274669 A1 | 10/2013 | Stempfle et al. |
| 2013/0275539 A1 | 10/2013 | Gross et al. |
| 2013/0291116 A1 | 10/2013 | Homer |
| 2013/0296823 A1 | 11/2013 | Melker et al. |
| 2013/0296984 A1 | 11/2013 | Burnett et al. |
| 2013/0317753 A1 | 11/2013 | Kamen et al. |
| 2013/0346108 A1 | 12/2013 | Kamen et al. |
| 2014/0025392 A1 | 1/2014 | Chandrasenan |
| 2014/0108783 A1 | 4/2014 | Suzuki |
| 2014/0142540 A1 | 5/2014 | Imhof |
| 2014/0142963 A1 | 5/2014 | Hill et al. |
| 2014/0163517 A1 | 6/2014 | Finan et al. |
| 2014/0172994 A1 | 6/2014 | Raumann et al. |
| 2014/0180711 A1* | 6/2014 | Kamen .................. G06Q 10/10<br>705/2 |
| 2014/0197950 A1 | 7/2014 | Shupp et al. |
| 2014/0215490 A1 | 7/2014 | Mathur et al. |
| 2014/0257251 A1 | 9/2014 | Bush et al. |
| 2014/0266790 A1 | 9/2014 | Al-Ali et al. |
| 2014/0266794 A1 | 9/2014 | Brown et al. |
| 2014/0269643 A1 | 9/2014 | Sun |
| 2014/0276571 A1 | 9/2014 | Ludolph |
| 2014/0280522 A1 | 9/2014 | Watte |
| 2014/0288947 A1* | 9/2014 | Simpson ................ G16H 10/60<br>705/2 |
| 2014/0294177 A1 | 10/2014 | Shastry et al. |
| 2014/0297329 A1 | 10/2014 | Rock |
| 2014/0316819 A1 | 10/2014 | Dunsirn et al. |
| 2014/0318639 A1 | 10/2014 | Peret et al. |
| 2014/0366878 A1 | 12/2014 | Baron |
| 2014/0371543 A1* | 12/2014 | Steinhauer ............ A61M 5/142<br>600/300 |
| 2015/0005935 A1 | 1/2015 | Bae et al. |
| 2015/0006907 A1 | 1/2015 | Brouwer et al. |
| 2015/0045729 A1 | 2/2015 | Denzer et al. |
| 2015/0058044 A1 | 2/2015 | Butler et al. |
| 2015/0058960 A1 | 2/2015 | Schmoyer et al. |
| 2015/0066531 A1 | 3/2015 | Jacobson et al. |
| 2015/0081894 A1 | 3/2015 | Blomquist |
| 2015/0100038 A1 | 4/2015 | McCann et al. |
| 2015/0100787 A1 | 4/2015 | Westin et al. |
| 2015/0117234 A1 | 4/2015 | Raman et al. |
| 2015/0151051 A1 | 6/2015 | Tsoukalis |
| 2015/0161354 A1 | 6/2015 | Blomquist |
| 2015/0199192 A1 | 7/2015 | Borges et al. |
| 2015/0199485 A1 | 7/2015 | Borges et al. |
| 2015/0207626 A1 | 7/2015 | Neftel et al. |
| 2015/0220890 A1 | 8/2015 | Seshadri et al. |
| 2015/0230760 A1 | 8/2015 | Schneider |
| 2015/0281128 A1 | 10/2015 | Sindhu |
| 2015/0325064 A1 | 11/2015 | Downey |
| 2015/0328396 A1 | 11/2015 | Adams et al. |
| 2015/0352301 A1 | 12/2015 | Stedman et al. |
| 2015/0371004 A1* | 12/2015 | Jones .................... G16H 70/40<br>705/2 |
| 2015/0379237 A1 | 12/2015 | Mills et al. |
| 2016/0001003 A1 | 1/2016 | Perazzo et al. |
| 2016/0006695 A1 | 1/2016 | Prodoehl et al. |
| 2016/0015885 A1 | 1/2016 | Pananen et al. |
| 2016/0034655 A1* | 2/2016 | Gray .................... G16H 20/17<br>713/1 |
| 2016/0045661 A1 | 2/2016 | Gray et al. |
| 2016/0051749 A1 | 2/2016 | Istoc |
| 2016/0063471 A1 | 3/2016 | Kobres et al. |
| 2016/0074573 A1* | 3/2016 | Kohlbrecher ......... A61M 5/172<br>604/151 |
| 2016/0158437 A1 | 6/2016 | Biasi et al. |
| 2016/0228633 A1 | 8/2016 | Welsch et al. |
| 2016/0241391 A1 | 8/2016 | Fenster |
| 2016/0277152 A1 | 9/2016 | Xiang et al. |
| 2016/0285876 A1 | 9/2016 | Perez et al. |
| 2016/0317742 A1 | 11/2016 | Gannon et al. |
| 2016/0350513 A1 | 12/2016 | Jacobson et al. |
| 2016/0378618 A1 | 12/2016 | Cmielowski |
| 2017/0034277 A1 | 2/2017 | Jackson et al. |
| 2017/0063559 A1 | 3/2017 | Wallrabenstein |
| 2017/0099148 A1 | 4/2017 | Ochmanski et al. |
| 2017/0104645 A1 | 4/2017 | Wooton et al. |
| 2017/0111301 A1 | 4/2017 | Robinson |
| 2017/0140134 A1 | 5/2017 | Brough et al. |
| 2017/0146381 A1 | 5/2017 | Eckel et al. |
| 2017/0147761 A1 | 5/2017 | Moskal et al. |
| 2017/0149567 A1 | 5/2017 | Moskal |
| 2017/0149929 A1 | 5/2017 | Moskal |
| 2017/0214762 A1 | 7/2017 | Swain et al. |
| 2017/0258401 A1 | 9/2017 | Volpe |
| 2017/0258986 A1 | 9/2017 | Tsoiukalis |
| 2017/0262590 A1 | 9/2017 | Karakosta et al. |
| 2017/0274140 A1 | 9/2017 | Howard et al. |
| 2017/0286637 A1 | 10/2017 | Arrizza et al. |
| 2017/0319780 A1 | 11/2017 | Belkin et al. |
| 2017/0325091 A1 | 11/2017 | Freeman et al. |
| 2017/0331804 A1 | 11/2017 | Jellison et al. |
| 2017/0351841 A1 | 12/2017 | Moskal |
| 2018/0063724 A1 | 3/2018 | Zhang et al. |
| 2018/0121613 A1 | 5/2018 | Connely, IV et al. |
| 2018/0122502 A1* | 5/2018 | Jones .................... G16H 50/20 |
| 2018/0126067 A1 | 5/2018 | Ledford et al. |
| 2018/0157821 A1 | 6/2018 | Fan |
| 2018/0181712 A1 | 6/2018 | Ensey et al. |
| 2018/0247712 A1 | 8/2018 | Muhsin et al. |
| 2018/0272117 A1 | 9/2018 | Fangrow |
| 2018/0278594 A1 | 9/2018 | Schiffman et al. |
| 2018/0317826 A1 | 11/2018 | Muhsin et al. |
| 2018/0322948 A1 | 11/2018 | Drost et al. |
| 2018/0359085 A1 | 12/2018 | Dervyn |
| 2019/0006044 A1 | 1/2019 | Brask |
| 2019/0030329 A1 | 1/2019 | Hannaman et al. |
| 2019/0036688 A1 | 1/2019 | Wasily et al. |
| 2019/0096518 A1 | 3/2019 | Pace |
| 2019/0132196 A1 | 5/2019 | Trivedi et al. |
| 2019/0147998 A1 | 5/2019 | Ruchti et al. |
| 2019/0166501 A1 | 5/2019 | Debates et al. |
| 2019/0172590 A1 | 6/2019 | Vesto et al. |
| 2019/0207965 A1 | 7/2019 | Espinosa |
| 2019/0228863 A1 | 7/2019 | Dharwad et al. |
| 2019/0229982 A1 | 7/2019 | Ikuta et al. |
| 2019/0240405 A1 | 8/2019 | Wehba et al. |
| 2019/0243829 A1 | 8/2019 | Butler et al. |
| 2019/0244689 A1 | 8/2019 | Atkin |
| 2019/0245942 A1 | 8/2019 | Moskal |
| 2019/0269852 A1 | 9/2019 | Kohlbrecher |
| 2019/0311803 A1 | 10/2019 | Kohlbrecher et al. |
| 2019/0348160 A1 | 11/2019 | Heavelyn et al. |
| 2019/0392929 A1 | 12/2019 | Gassman |
| 2020/0023127 A1 | 1/2020 | Simpson et al. |
| 2020/0027541 A1 | 1/2020 | Xavier et al. |
| 2020/0027542 A1 | 1/2020 | Xavier et al. |
| 2020/0027543 A1 | 1/2020 | Xavier et al. |
| 2020/0027548 A1 | 1/2020 | Xavier et al. |
| 2020/0027549 A1 | 1/2020 | Xavier et al. |
| 2020/0027550 A1 | 1/2020 | Xavier et al. |
| 2020/0027551 A1 | 1/2020 | Xavier et al. |
| 2020/0028837 A1 | 1/2020 | Xavier et al. |
| 2020/0028914 A1 | 1/2020 | Xavier et al. |
| 2020/0028929 A1 | 1/2020 | Xavier et al. |
| 2020/0035355 A1 | 1/2020 | Xavier et al. |
| 2020/0054825 A1 | 2/2020 | Kamen et al. |
| 2020/0061291 A1 | 2/2020 | Day et al. |
| 2020/0118692 A1 | 4/2020 | Booker et al. |
| 2020/0153627 A1 | 5/2020 | Wentz |
| 2020/0206413 A1 | 7/2020 | Silkaitis et al. |
| 2020/0220865 A1 | 7/2020 | Finger et al. |
| 2020/0282139 A1 | 9/2020 | Susi |
| 2020/0306443 A1 | 10/2020 | Day |
| 2020/0330685 A1 | 10/2020 | Day |
| 2020/0334497 A1 | 10/2020 | Barrett et al. |

(56) References Cited

U.S. PATENT DOCUMENTS

| | | |
|---|---|---|
| 2020/0335194 A1 | 10/2020 | Jacobson et al. |
| 2020/0351376 A1 | 11/2020 | Moskal |
| 2020/0353167 A1 | 11/2020 | Vivek et al. |
| 2020/0353168 A1 | 11/2020 | Keenan et al. |
| 2021/0014259 A1 | 1/2021 | Harris et al. |
| 2021/0045640 A1 | 2/2021 | Poltorak |
| 2021/0085855 A1 | 3/2021 | Belkin et al. |
| 2021/0252210 A1 | 8/2021 | Day et al. |
| 2021/0316072 A1 | 10/2021 | Wehba et al. |
| 2021/0358603 A1 | 11/2021 | Xavier et al. |
| 2021/0375421 A1 | 12/2021 | Ruchti et al. |
| 2021/0375438 A1 | 12/2021 | Xavier et al. |
| 2021/0409362 A1 | 12/2021 | Katis et al. |
| 2022/0023535 A1 | 1/2022 | Day |
| 2022/0037011 A1 | 2/2022 | Fryman |
| 2022/0037012 A1 | 2/2022 | Fryman |
| 2022/0051777 A1 | 2/2022 | Xavier et al. |
| 2022/0062541 A1 | 3/2022 | Kamen et al. |
| 2022/0129452 A1 | 4/2022 | Butler et al. |
| 2022/0139536 A1 | 5/2022 | Xavier et al. |
| 2022/0139537 A1 | 5/2022 | Xavier et al. |
| 2022/0139538 A1 | 5/2022 | Xavier et al. |
| 2022/0150307 A1 | 5/2022 | Walsh et al. |
| 2022/0165404 A1 | 5/2022 | Vivek et al. |
| 2022/0189605 A1 | 6/2022 | Kelly et al. |
| 2022/0223283 A1 | 7/2022 | Biasi et al. |
| 2022/0270736 A1 | 8/2022 | Kohlbrecher |
| 2022/0328175 A1 | 10/2022 | Arrizza et al. |
| 2022/0331513 A1 | 10/2022 | Howard et al. |
| 2022/0344023 A1 | 10/2022 | Xavier et al. |
| 2022/0375565 A1 | 11/2022 | Xavier et al. |
| 2023/0009405 A1 | 1/2023 | Xavier et al. |
| 2023/0009417 A1 | 1/2023 | Xavier et al. |
| 2023/0139360 A1 | 5/2023 | Kohlbrecher et al. |
| 2023/0145267 A1 | 5/2023 | Xavier et al. |
| 2023/0147762 A1 | 5/2023 | Xavier et al. |
| 2023/0166026 A1 | 6/2023 | Jacobson et al. |
| 2023/0188465 A1 | 6/2023 | Jha et al. |
| 2023/0253108 A1 | 8/2023 | Dharwad et al. |
| 2023/0285660 A1 | 9/2023 | Day et al. |
| 2023/0298768 A1 | 9/2023 | Jacobson et al. |
| 2023/0320935 A1 | 10/2023 | Tagliamento |
| 2023/0321350 A1 | 10/2023 | Day |
| 2023/0321351 A1 | 10/2023 | Wehba et al. |
| 2023/0326570 A1 | 10/2023 | Kohlbrecher |
| 2023/0410989 A1 | 12/2023 | Xavier et al. |
| 2024/0038358 A1 | 2/2024 | Xavier et al. |
| 2024/0047035 A1 | 2/2024 | Ruchti et al. |
| 2024/0071609 A1 | 2/2024 | Rohlwing |
| 2024/0293610 A1 | 9/2024 | Jacobson |
| 2024/0347161 A1 | 10/2024 | Kohlbrecher |
| 2024/0363236 A1 | 10/2024 | Arrizza et al. |
| 2024/0390583 A1 | 11/2024 | Wehba et al. |

FOREIGN PATENT DOCUMENTS

| | | |
|---|---|---|
| CA | 2 060 151 | 8/1997 |
| CA | 2 125 300 | 10/1999 |
| CA | 2 630 102 | 10/2008 |
| CA | 2 687 587 | 12/2008 |
| CA | 2 897 897 | 7/2014 |
| CA | 2 898 825 | 7/2014 |
| CA | 2 900 564 | 10/2014 |
| CA | 2 606 968 | 1/2020 |
| CN | 1759398 | 4/2006 |
| CN | 102521474 | 6/2012 |
| CN | 103816582 | 5/2014 |
| CN | 103920206 | 7/2014 |
| CN | 102300501 | 4/2015 |
| CN | 104487976 | 4/2015 |
| CN | 107810536 | 1/2023 |
| CO | 01110843 | 8/2003 |
| DE | 31 12 762 | 1/1983 |
| DE | 34 35 647 | 7/1985 |
| DE | 198 44 252 | 3/2000 |
| DE | 199 32 147 | 1/2001 |
| DE | 103 52 456 | 7/2005 |
| EP | 0 319 267 | 6/1989 |
| EP | 0 380 061 | 8/1990 |
| EP | 0 384 155 | 8/1990 |
| EP | 0 460 533 | 12/1991 |
| EP | 0 564 127 | 6/1993 |
| EP | 0 633 035 | 1/1995 |
| EP | 0 652 528 | 5/1995 |
| EP | 0 672 427 | 9/1995 |
| EP | 0 683 465 | 11/1995 |
| EP | 0 880 936 | 12/1998 |
| EP | 1 050 993 | 11/2000 |
| EP | 1 157 711 | 11/2001 |
| EP | 1 174 817 | 1/2002 |
| EP | 0 664 102 | 4/2002 |
| EP | 1 197 178 | 4/2002 |
| EP | 0 830 775 | 8/2002 |
| EP | 1 500 025 | 4/2003 |
| EP | 1 487 171 | 7/2007 |
| EP | 1 933 497 | 6/2008 |
| EP | 2 026 223 | 2/2009 |
| EP | 2 113 842 | 11/2009 |
| EP | 2 228 004 | 9/2010 |
| EP | 2 243 506 | 10/2010 |
| EP | 2 410 448 | 1/2012 |
| EP | 2 742 961 | 6/2014 |
| EP | 2 874 087 | 5/2015 |
| ES | 2 371 995 | 1/2012 |
| FR | 2 717 919 | 9/1995 |
| GB | 2 285 135 | 6/1995 |
| JP | 04-161139 | 6/1992 |
| JP | 07-502678 | 3/1995 |
| JP | 11-500643 | 1/1999 |
| JP | 2000-316820 | 11/2000 |
| JP | 2002-531154 | 9/2002 |
| JP | 2003-016183 | 1/2003 |
| JP | 2003-296173 | 10/2003 |
| JP | 2003-308586 | 10/2003 |
| JP | 2005-021463 | 1/2005 |
| JP | 2005-527284 | 9/2005 |
| JP | 2005-284846 | 10/2005 |
| JP | 2006-047319 | 2/2006 |
| JP | 2006-520949 | 9/2006 |
| JP | 2007-518479 | 7/2007 |
| JP | 2007-525256 | 9/2007 |
| JP | 2008-080036 | 4/2008 |
| JP | 2008-516303 | 5/2008 |
| JP | 2008-158622 | 7/2008 |
| JP | 2008-529675 | 8/2008 |
| JP | 2009-163534 | 7/2009 |
| JP | 2010-502361 | 1/2010 |
| JP | 2011-506048 | 3/2011 |
| JP | 2012-011204 | 1/2012 |
| JP | 2012-070991 | 4/2012 |
| JP | 2012-523895 | 10/2012 |
| JP | 2014-068283 | 4/2014 |
| JP | 5647644 | 1/2015 |
| TW | 200426656 | 12/2004 |
| TW | I631966 | 8/2018 |
| WO | WO 84/001719 | 5/1984 |
| WO | WO 91/016416 | 10/1991 |
| WO | WO 92/010985 | 7/1992 |
| WO | WO 92/013322 | 8/1992 |
| WO | WO 94/005355 | 3/1994 |
| WO | WO 96/008755 | 3/1996 |
| WO | WO 96/025186 | 8/1996 |
| WO | WO 96/025963 | 8/1996 |
| WO | WO 98/012670 | 3/1998 |
| WO | WO 98/019263 | 5/1998 |
| WO | WO 99/051003 | 10/1999 |
| WO | WO 00/013580 | 3/2000 |
| WO | WO 00/053243 | 9/2000 |
| WO | WO 01/014974 | 3/2001 |
| WO | WO 01/033484 | 5/2001 |
| WO | WO 01/045014 | 6/2001 |
| WO | WO 01/083007 | 11/2001 |
| WO | WO 02/005702 | 1/2002 |
| WO | WO 02/036044 | 5/2002 |

(56) References Cited

FOREIGN PATENT DOCUMENTS

| | | |
|---|---|---|
| WO | WO 02/049153 | 6/2002 |
| WO | WO 02/049279 | 6/2002 |
| WO | WO 02/069099 | 9/2002 |
| WO | WO 02/081015 | 10/2002 |
| WO | WO 02/088875 | 11/2002 |
| WO | WO 03/006091 | 1/2003 |
| WO | WO 03/023551 | 3/2003 |
| WO | WO 03/050917 | 6/2003 |
| WO | WO 03/091836 | 11/2003 |
| WO | WO 03/094092 | 11/2003 |
| WO | WO 2004/060455 | 7/2004 |
| WO | WO 2004/070557 | 8/2004 |
| WO | WO 2004/070562 | 8/2004 |
| WO | WO 2004/072828 | 8/2004 |
| WO | WO 2005/036447 | 4/2005 |
| WO | WO 2005/050526 | 6/2005 |
| WO | WO 2005/057175 | 6/2005 |
| WO | WO 2005/066872 | 7/2005 |
| WO | WO 2007/087443 | 8/2007 |
| WO | WO 2007/117705 | 10/2007 |
| WO | WO 2007/127879 | 11/2007 |
| WO | WO 2007/127880 | 11/2007 |
| WO | WO 2008/059495 | 5/2008 |
| WO | WO 2008/064254 | 5/2008 |
| WO | WO 2008/067245 | 6/2008 |
| WO | WO 2008/082854 | 7/2008 |
| WO | WO 2008/088490 | 7/2008 |
| WO | WO 2008/097316 | 8/2008 |
| WO | WO 2008/103915 | 8/2008 |
| WO | WO 2008/124478 | 10/2008 |
| WO | WO 2008/134146 | 11/2008 |
| WO | WO 2009/016504 | 2/2009 |
| WO | WO 2009/023406 | 2/2009 |
| WO | WO 2009/023407 | 2/2009 |
| WO | WO 2009/023634 | 2/2009 |
| WO | WO 2009/036327 | 3/2009 |
| WO | WO 2009/049252 | 4/2009 |
| WO | WO 2010/017279 | 2/2010 |
| WO | WO 2010/033919 | 3/2010 |
| WO | WO 2010/053703 | 5/2010 |
| WO | WO 2010/075371 | 7/2010 |
| WO | WO 2010/099313 | 9/2010 |
| WO | WO 2010/114929 | 10/2010 |
| WO | WO 2010/119409 | 10/2010 |
| WO | WO 2010/124127 | 10/2010 |
| WO | WO 2010/130992 | 11/2010 |
| WO | WO 2010/135646 | 11/2010 |
| WO | WO 2010/135654 | 11/2010 |
| WO | WO 2010/135686 | 11/2010 |
| WO | WO 2011/005633 | 1/2011 |
| WO | WO 2011/022549 | 2/2011 |
| WO | WO 2012/048833 | 4/2012 |
| WO | WO 2012/049214 | 4/2012 |
| WO | WO 2012/049218 | 4/2012 |
| WO | WO 2012/120078 | 9/2012 |
| WO | WO 2012/140547 | 10/2012 |
| WO | WO 2012/164556 | 12/2012 |
| WO | WO 2012/170942 | 12/2012 |
| WO | WO 2013/045506 | 4/2013 |
| WO | WO 2014/100736 | 6/2014 |
| WO | WO 2014/131729 | 9/2014 |
| WO | WO 2014/131730 | 9/2014 |
| WO | WO 2015/047595 | 4/2015 |
| WO | WO 2015/124569 | 8/2015 |
| WO | WO 2016/179389 | 11/2016 |
| WO | WO 2017/176928 | 10/2017 |
| WO | WO 2017/200989 | 11/2017 |
| WO | WO 2019/219290 | 11/2019 |
| WO | WO-2019219290 A1 * 11/2019 ............ G16H 40/67 |
| WO | WO 00/003344 | 1/2020 |
| WO | WO 2020/018388 | 1/2020 |
| WO | WO 2020/018389 | 1/2020 |
| WO | WO 2020/227403 | 11/2020 |
| WO | WO 2021/201884 | 10/2021 |
| WO | WO 2022/006014 | 1/2022 |
| WO | WO 2022/051230 | 3/2022 |
| WO | WO 2023/159134 | 8/2023 |

OTHER PUBLICATIONS

Bellare et al., "Security Proofs for Identity-Based Identification and Signature Schemes", Lecture Notes in Computer Science, Jan. 2009, vol. 22, No. 1, pp. 18.

Gutwin et al., "Gone But Not Forgotten: Designing for Disconnection in Synchronous Groupware", CSCW 2010, Feb. 6-10, 2010, Savannah, Georgia, USA., pp. 179-188.

Huang et al., "Secure Identity-Based Data Sharing and Profile Matching for Mobile Healthcare Social Networks in Cloud Computing", vol. 6, Jul. 2018, pp. 36584-36594.

Li et al., "Hijacking an Insulin Pump: Security Attacks and Defenses for a Diabetes Therapy System", 2011 IEEE 13th International Conference on e-Health Networking, Applications and Services, 2011, pp. 150-156.

Michienzi, Kelly, "Managing Drug Library Updates", Pharmacy Purchasing Products, https://www.pppmag.com/article/1061, Feb. 2012, vol. 9, pp. 22-23.

Nojoumian et al., "Social Secret Sharing in Cloud Computing Using a New Trust Function", 2012 Tenth Annual International Conference on Privacy, Security and Trust, pp. 161-167.

"Sigma Spectrum: Operator's Manual", May 15, 2008, pp. 63. https://usme.com/content/manuals/sigma-spectrum-operator-manual.pdf.

"TCG TPM v2.0 Provisioning Guidance", Reference, Version 1, Revision 1, Mar. 15, 2017, pp. 1-43.

Yoo et al., "Code-Based Authentication Scheme for Lightweight Integrity Checking of Smart Vehicles", IEEE Access, 2018, vol. 6, pp. 46731-46741.

Block, Alexander, "Secret Sharing and 1-11 Threshold Signatures with BLS", Jul. 2, 2018, https://blog.dash.org/secret-sharing-and-threshold-signatures-with-bls-954d1587b5f, in 8 pages.

Solapurkar et al., "Building Secure Healthcare Services Using OAuth 2.0 and JSON Web Token in IOT Cloud Scenario", Dec. 2016, 2nd International Conference on Contemporary Computing and Informatics, pp. 99-10.

Ahn et al., "Towards Scalable Authentication in Health Services", Eleventh IEEE International Workshops on Enabling Technologies: Infrastructure for Collaborative Enterprises, Jun. 2002, pp. 83-88.

Akridge, Jeannie, "New Pumps Outsmart User Error", Healthcare Purchasing News, Apr. 2011, pp. 10, http://web.archive.org/web/20110426122450/http://www.hpnonline.com/inside/2011-04/1104-OR-Pumps.html.

Alur et al., "Formal Specifications and Analysis of the Computer-Assisted Resuscitation Algorithm (CARA) Infusion Pump Control System", International Journal on Software Tools for Technology Transfer, Feb. 2004, vol. 5, No. 4, pp. 308-319.

Aragon, Daleen RN, Ph.D., CCRN, "Evaluation of Nursing Work Effort and Perceptions About Blood Glucose Testing in Tight Glycemic Control", American Journal of Critical Care, Jul. 2006, vol. 15, No. 4, pp. 370-377.

ASHP Advantage, "Improving Medication Safety in Health Systems Through Innovations in Automation Technology", Proceedings of Educational Symposium and Educational Sessions during the 39th ASHP Midyear Clinical Meeting, Dec. 5-9, 2004, Orlando, FL, pp. 28.

Beard et al., "Total Quality Pain Management: History, Background, Resources", Abbott Laboratories, TQPM Survey History, available Feb. 2015 or earlier, pp. 1-3.

Bektas et al., "Bluetooth Communication Employing Antenna Diversity", Proceedings of Eight IEEE International Symposium on Computers and Communication, Jul. 2003, pp. 6.

Bequette, Ph.D., "A Critical Assessment of Algorithms and Challenges in the Development of a Closed-Loop Artificial Pancreas", Diabetes Technology & Therapeutics, Feb. 28, 2005, vol. 7, No. 1, pp. 28-47.

(56)        References Cited

OTHER PUBLICATIONS

Bequette, B. Wayne, Ph.D., "Analysis of Algorithms for Intensive Care Unit Blood Glucose Control", Journal of Diabetes Science and Technology, Nov. 2007, vol. 1, No. 6, pp. 813-824.
Braun, "Infusomat® Space and Accessories", Instructions for Use, Nov. 2010, pp. 68. http://corp.bbraun.ee/Extranet/Infusionipumbad/Kasutusjuhendid/Vanad/Kasutusjuhend-Infusomat_Space(vers688J,inglise_k).pdf.
Brownlee, Seth, "Product Spotlight: The Plum A+ with Hospira MedNet Infusion System", PP&P Magazine, Dec. 2005, vol. 2, No. 7, pp. 2.
Cannon, MD et al., "Automated Heparin-Delivery System to Control Activated Partial Thromboplastin Time", Circulation, Feb. 16, 1999, vol. 99, pp. 751-756.
Cardinal Health, "Alaris® Syringe Pumps" Technical Service Manual, Copyright 2002-2006, Issue 9, pp. 1-88, http://www.frankshospitalworkshop.com/equipment/documents/infusion_pumps/service_manuals/Cardinal_Alaris_-_Service_Manual.pdf.
"CareAware® Infusion Management", Cerner Store, as printed May 12, 2011, pp. 3, https://store.cerner.com/items/7.
Chen et al., "Enabling Location-Based Services on Wireless LANs", The 11th IEEE International Conference on Networks, ICON 2003, Sep. 28-Oct. 1, 2003, pp. 567-572.
"Computer Dictionary", Microsoft Press, Third Edition, Microsoft Press, 1997, pp. 430 & 506.
"Context-Free Grammar", Wikipedia.org, as last modified Mar. 5, 2010 in 11 pages, https://en.wikipedia.org/w/index.php/?title=Context-free_grammar&oldid=347915989.
Crawford, Anne J., MSN, RNC, "Building a Successful Quality Pain Service: Using Patient Satisfaction Data and the Clinical Practice Guideline", USA, 1995, pp. 1-6.
Crocker et al., "Augmented BNF for Syntax Specifications: ABNF", Network Working Group, Standards Track, Jan. 2008, pp. 16.
Davidson et al., "A Computer-Directed Intravenous Insulin System Shown to be Safe, Simple, and Effective in 120,618 h of Operation", Diabetes Care, Oct. 2005, vol. 28, No. 10, pp. 2418-2423.
Davies, T., "Cordless Data Acquisition in a Hospital Environment", IEE Colloquium on Cordless Computing—Systems and User Experience, 1993, pp. 4.
Dayhoff et al., "Medical Data Capture and Display: The Importance of Clinicians' Workstation Design", AMIA, Inc., 1994, pp. 541-545.
Diabetes Close Up, Close Concerns AACE Inpatient Management Conference Report, Consensus Development Conference on Inpatient Diabetes and Metabolic Control, Washington, D.C., Dec. 14-16, 2003, pp. 1-32.
Doesburg et al., "Improved Usability of a Multi-Infusion Setup Using a Centralized Control Interface: A Task-Based Usability Test", Aug. 11, 2017, PLoS One, vol. 12, No. 8, pp. 10.
"Download", Free On-Line Dictionary of Computing, as archived Jun. 16, 2010 in 1 page, http://web.archive.org/web/20100616010314/https://foldoc.org/download.
East PhD et al., "Digital Electronic Communication Between ICU Ventilators and Computers and Printers", Respiratory Care, Sep. 1992, vol. 37, No. 9, pp. 1113-1122.
Edworthy, Judy, "Medical Audible Alarms: A Review", Journal of the American Medical Informatics Association, vol. 20, No. 3, 2013, pp. 584-589.
Einhorn, George W., "Total Quality Pain Management: A Computerized Quality Assessment Tool for Postoperative Pain Management", Abbott Laboratories, Chicago, IL, Mar. 2, 2000, pp. 1-4.
Eskew et al., "Using Innovative Technologies to Set New Safety Standards for the Infusion of Intravenous Medications", Hospital Pharmacy, 2002, vol. 37, No. 11, pp. 1179-1189.
Felleiter et al., "Data Processing in Prehospital Emergency Medicine", International journal of Clinical Monitoring and Computing, Feb. 1995, vol. 12, No. 1, pp. 37-41.
"File Verification", Wikipedia.org, as last modified Oct. 11, 2011 in 2 pages, https://en.wikipedia.org/w/index.php?title=File_verification&oldid=455048290.

Fogt et al., Development and Evaluation of a Glucose Analyzer for a Glucose-Controlled Insulin Infusion System (Biostator®), Clinical Chemistry, 1978, vol. 24, No. 8, pp. 1366-1372.
Gabel et al., "Camp: A Common API for Measuring Performance", 21st Large Installations System Administration Conference (LISA '07), 2007, pp. 49-61.
Gage et al., "Automated Anesthesia Surgery Medical Record System", International Journal of Clinical Monitoring and Computing, Dec. 1990, vol. 7, No. 4, pp. 259-263.
Galt et al., "Personal Digital Assistant-Based Drug Information Sources: Potential to Improve Medication Safety", Journal of Medical Library Association, Apr. 2005, vol. 93, No. 2, pp. 229-236.
Gardner, Ph.D. et al., "Real Time Data Acquisition: Recommendations for the Medical Information Bus (MIB)", 1992, pp. 813-817.
"General-Purpose Infusion Pumps", Health Devices, EXRI Institute, Oct. 1, 2002, vol. 31, No. 10, pp. 353-387.
Givens et al., "Exploring the Internal State of User Interfaces by Combining Computer Vision Techniques with Grammatical Inference", Proceedings of the 2013 International Conference on Software Engineering, San Francisco, CA, May 18-26, 2013, pp. 1165-1168.
Glaeser, "A Hierarchical Minicomputer System for Continuous Post-Surgical Monitoring", Computers and Biomedical Research, Aug. 31, 1975, pp. 336-361.
Goldberg et al., "Clinical Results of an Updated Insulin Infusion Protocol in Critically Ill Patients", Diabetes Spectrum, 2005, vol. 18, No. 3, pp. 188-191.
Gomez et al., "CLAM: Connection-Less, Lightweight, and Multiway Communication Support for Distributed Computing", Computer Science, 1997, vol. 1199, pp. 227-240.
"GPS Tracker for Medical Equipment", http://www.trackingsystem.com/forbusinesses/corporate-trackingsystem/1098-gps-tracker-formedicalequipment.html, Mar. 15, 2015, pp. 2.
Graseby, "Model 3000/500 and Micro 3100/505: Volumetric Infusion Pump", Technical Service Manual, Graseby Medical Ltd., Apr. 2002, Issue A, pp. 160.
Graseby, "Model 3000/500 and Micro 3100/505: Volumetric Infusion Pump: Illustrated Parts List for Pump Serial Numbers from 3000 to 59,999", Technical Service Manual, Graseby Medical Ltd., Apr. 2002, Issue A, pp. 71.
Halpern et al., "Changes in Critical Care Beds and Occupancy in the United States 1985-2000: Differences Attributable to Hospital Size", Critical Care Medical, Aug. 2006, vol. 34, No. 8, pp. 2105-2112.
Hamann et al., "PUMPSIM: A Software Package for Simulating Computer-Controlled Drug Infusion Pumps", Annual International Conference of the IEEE Engineering in Medicine and Biology Society, 1990, vol. 12, No. 5, pp. 2019-2020.
Hasegawa et al., "On a Portable Memory Device for Physical Activities and Informations of Maternal Perception", Journal of Perinatal Medicine, 1988, vol. 16, No. 4, pp. 349-356.
Hawley et al., "Clinical Implementation of an Automated Medical Information Bus in an Intensive Care Unit", Proceedings of the Annual Symposium on Computer Application in Medical Care, Nov. 9, 1988, pp. 621-624.
Hayes-Roth et al., "Guardian: A Prototype Intelligent Agent for Intensive-Care Monitoring", Artificial Intelligence in Medicine, vol. 4, Dec. 31, 1992, pp. 165-185.
Hospira, GemStar® Pain Management Infusion System 9-084-PR1-2-2, www.hospira.com/products/gemstar_painmanagement.aspx, Jan. 28, 2010, pp. 1-2.
Introducing Abbott TQPM (Total Quality Pain Management), Abbott Laboratories, Abbott Park, IL, May 2000, pp. 1-4.
"Infusion Pump", Wikipedia.org, as last modified Mar. 27, 2014, in 3 pages, https://web.archive.org/web/20140703024932/https://en.wikipedia.org/wiki/Infusion_pump.
Isaka et al., "Control Strategies for Arterial Blood Pressure Regulation", IEEE Transactions on Biomedical Engineering, Apr. 1993, vol. 40, No. 4, pp. 353-363.
Johnson et al., "Using BCMA Software to Improve Patient Safety in Veterans Administration Medical Centers", Journal of Healthcare Information Management, Dec. 6, 2004, vol. 16, No. 1, pp. 46-51.
Kent Displays, "Reflex™ Electronic Skins", Product Brief 25127B, 2009, pp. 2.

(56) References Cited

OTHER PUBLICATIONS

Kent Displays, "Reflex Electronic Skins Engineering Evaluation Kit", 25136A, Mar. 10, 2009.

Lefkowitz et al., "A Trial of the Use of Bar Code Technology to Restructure a Drug Distribution and Administration System", Hospital Pharmacy, Mar. 31, 1991, vol. 26, No. 3, pp. 239-242.

Lenssen et al., "Bright Color Electronic Paper Technology and Applications", IDS '09 Publication EP1-2 (Phillips Research), 2009, pp. 529-532.

Leveson, Nancy, "Medical Devices: The Therac-25", Appendix A, University of Washington, 1995, pp. 49.

Linkens, D.A. "Computer Control for Patient Care", Computer Control of Real-Time Processes, IEE Control Engineering Series 41, 1990, Ch. 13, pp. 216-238.

Mako Hill et al., "The Official Ubuntu Book", Shoeisha Co., Ltd., 1st Edition, Jun. 11, 2007, pp. 115 to 125.

Marshall, et al., "New Microprocessor-Based Insulin Controller", IEEE Transactions on Biomedical Engineering, Nov. 1983, vol. BME-30, No. 11, pp. 689-695.

Martino et al., "Automation of a Medical Intensive Care Environment with a Flexible Configuration of Computer Systems", Proceedings of the Annual Symposium on Computer Application in Medical Care, Nov. 5, 1980, vol. 3, pp. 1562-1568.

Matsunaga et al., "On the Use of Machine Learning to Predict the Time and Resources Consumed by Applications", 2010 10th IEEE/ACM International Conference on Cluster, Cloud and Grid Computing (CCGrid), May 17-20, 2010, pp. 495-504.

Mauseth et al., "Proposed Clinical Application for Tuning Fuzzy Logic Controller of Artificial Pancreas Utilizing a Personalization Factor", Journal of Diabetes Science and Technology, Jul. 2010, vol. 4, No. 4, pp. 913-922.

"McKesson Automation and Alaris Medical Systems Developing Point-of-Care Bar Coding Solution to Improve IV Medication Safety", PR Newswire, NY, Dec. 9, 2002, pp. 4.

Medfusion™, "Medfusion Syringe Infusion Pump Model 4000", Operator's Manual, Software Version V1.1, Sep. 2011, pp. 154. http://www.medfusionpump.com/assets/literature/manuals/Operators_Manual_4000_40-5760-51A.pdf.

Metnitz et al., "Computer Assisted Data Analysis in Intensive Care: the ICDEV Project-Development of a Scientific Database System for Intensive Care", International Journal of Clinical Monitoring and Computing, Aug. 1995, vol. 12, No. 3, pp. 147-159.

Micrel Medical Devices, "MP Daily +" http://web.archive.org/web/20130803235715/http://www.micrelmed.com/index.aspx?productid=9 as archived Aug. 3, 2013 in 1 page.

Moghissi, Etie, MD, FACP, FACE, "Hyperglycemia in Hospitalized Patients", A Supplement to ACP Hospitalist, Jun. 15, 2008, pp. 32.

Murray, Jr. et al., "Automated Drug Identification System (during surgery)", IEEE Proceedings of Southeastcon '91, Apr. 7-10, 1991, pp. 265.

Nicholson et al., "'Smart' Infusion Apparatus for Computation and Automated Delivery of Loading, Tapering, and Maintenance Infusion Regimens of Lidocaine, Procainamide, and Theophylline", Proceedings of the Seventh Annual Symposium on Computer Applications in Medical Care, Oct. 1983, pp. 212-213.

Nolan et al., "The P1073 Medical Information Bus Standard: Overview and Benefits for Clinical Users", 1990, pp. 216-219.

Omnilink Systems, Inc., "Portable Medical Equipment Tracking", http://www.omnilink.com/portablemedicalequipmenttracking/, Mar. 15, 2015, pp. 2.

O'Shea, Kristen L., "Infusion Management: Working Smarter, Not Harder", Hospital Pharmacy, Apr. 2013, vol. 48, No. 3, pp. S1-S14.

Package Management in Debian GNU/Linux, Debian GNU/Linux Expert Desktop Use Special, Giutsu-Hyohron Co., Ltd., First Edition, Sep. 25, 2004, pp. 183-185.

Passos et al., "Distributed Software Platform for Automation and Control of General Anaesthesia", Eighth International Symposium on Parallel and Distributed Computing, ISPDC '09, Jun. 30-Jul. 4, 2009, pp. 8.

Philips, "IntelliSpace Event Management and IntelliVue Patient Monitoring", Release 10, 2011, http://incenter.medical.philips.com/doclib/enc/fetch/2000/4504/577242/577243/577247/582646/583147/8359175/Philips_Patient_Monitoring_and_IntelliSpace_Event_Management_Interoperability.pdf%3fnodeid%3d8508574%26vernum%3d-2, pp. 2.

Pretty et al., "Hypoglycemia Detection in Critical Care Using Continuous Glucose Monitors: An in Silico Proof of Concept Analysis", Journal of Diabetes Science and Technology, Jan. 2010, vol. 4, No. 1, pp. 15-24.

Rappoport, Arthur E., "A Hospital Patient and Laboratory machine-Readable Identification System (MRIS) Revisited", Journal of Medical Systems, Apr. 1984, vol. 8, Nos. 1/2, pp. 133-156.

Ritchie et al., "A Microcomputer Based Controller for Neuromuscular Block During Surgery", Annals of Biomedical Engineering, Jan. 1985, vol. 13, No. 1, pp. 3-15.

Saager et al., "Computer-Guided Versus Standard Protocol for Insulin Administration in Diabetic Patients Undergoing Cardiac Surgery", Annual Meeting of the American Society of Critical Care Anesthesiologists, Oct. 13, 2006.

Sanders et al., "The Computer in a Programmable Implantable Medication System (PIMS)", Proceedings of the Annual Symposium on Computer Application in Medical Care, Nov. 2, 1982, pp. 682-685.

Schilling et al., "Optimizing Outcomes! Error Prevention and Evidence-Based Practice with IV Medications", A Pro-Ce Publication, Hospira, Inc., Feb. 6, 2012, pp. 56.

Schulze et al., "Advanced Sensors Technology Survey", Final Report, Feb. 10, 1992, pp. 161.

Scott, et al., "Using Bar-Code Technology to Capture Clinical Intervention Data in a Hospital with a Stand-Alone Pharmacy Computer System", Mar. 15, 1996, American Journal of Health-System Pharmacy, vol. 53, No. 6, pp. 651-654.

Sebald et al., "Numerical Analysis of a Comprehensive in Silico Subcutaneous Insulin Absorption Compartmental Model", 31st Annual International Conference of the IEEE Engineering in Medicine and Biology Society, Sep. 2-6, 2009, pp. 3901-3904.

Shabot, M. Michael, "Standardized Acquisition of Bedside Data: The IEEE P1073 Medical Information Bus", International Journal of Clinical Monitoring and Computing, vol. 6, Sep. 27, 1989, pp. 197-204.

Sheppard, Louis, Ph.D., "Automation of the Infusion of Drugs Using Feedback Control", Journal of Cardiothoracic and Vascular Anesthesia, Feb. 28, 1989, vol. 3, No. 1, pp. 1-3.

Sheppard, Louis, Ph.D., "Computer Control of the Infusion of Vasoactive Drugs", Annals of Biomedical Engineering, Jul. 1980, vol. 8, No. 4-6, pp. 431-444.

Sheppard, Louis, Ph.D., "The Application of Computers to the Measurement, Analysis, and Treatment of Patients Following Cardiac Surgical Procedures", The University of Alabama in Birmingham, Oct. 31, 1977, pp. 297-300.

Sheppard, Louis, Ph.D., "The Computer in the Care of Critically Ill Patients", Proceedings of the IEEE, Sep. 1979, vol. 67, No. 9, pp. 1300-1306.

"Sigma Spectrum: Operator's Manual", Oct. 2009, pp. 72. http://static.medonecapital.com/manuals/userManuals/Sigma-Spectrum-Operator-Manual-October-2009.pdf.

Simonsen, Michael Ph.D., POC Testing, New Monitoring Strategies on Fast Growth Paths in European Healthcare Arenas, Biomedical Business & Technology, Jan. 2007, vol. 30, No. 1, pp. 1-36.

Siv-Lee et al., "Implementation of Wireless 'Intelligent' Pump IV Infusion Technology in a Not-for-Profit Academic Hospital Setting", Hospital Pharmacy, Sep. 2007, vol. 42, No. 9, pp. 832-840. http://www.thomasland.com/hpj4209-832.pdf.

Slack, W.V., "Information Technologies for Transforming Health Care", https://www.andrew.cmu.edu/course/90-853/medis.dir/otadocs.dir/03ch2.pdf, Ch. 2, 1995, pp. 29-78.

Smith, Joe, "Infusion Pump Informatics", CatalyzeCare: Transforming Healthcare, as printed May 12, 2011, pp. 2.

Sodders, Lisa, "VA Center Keeps Medicine in Right Hands", The Capital-Journal, Dec. 4, 1999, pp. 1-2.

(56)          References Cited

OTHER PUBLICATIONS

"Software Versioning", Wikipedia.org, dated Oct. 16, 2011 in 11 pages, https://en.wikipedia.org/w/index.php?title=Software_versioning &oldid=455859110.

Stitt, F.W., "The Problem-Oriented Medical Synopsis: a Patient-Centered Clinical Information System", Proceedings of the Annual Symposium on Computer Application in Medical Care, 1994, pp. 88-92.

Stokowski, Laura A. RN, MS, "Using Technology to Improve Medication Safety in the Newborn Intensive Care Unit", Advances in Neonatal Care, Dec. 2001, vol. 1, No. 2, pp. 70-83.

Sutton et al., "The Syntax and Semantics of the PROforma Guideline Modeling Language", Journal of the American Medical Informatics Association, Sep./Oct. 2003, vol. 10, No. 5, pp. 433-443.

Szeinbach et al., "Automated Dispensing Technologies: Effect on Managed Care", Journal of Managed Care Pharmacy (JMCP), Sep./Oct. 1995, vol. 1, No. 2, pp. 121-127.

Szolovits et al., "Guardian Angel: Patient-Centered Health Information Systems", Technical Report MIT/LCS/TR-604, Massachusetts Institute of Technology Laboratory for Computer Science, May 1994, pp. 39.

Van Den Berghe, M.D., Ph.D., et al., "Intensive Insulin Therapy in Critically Ill Patients", The New England Journal of Medicine, Nov. 8, 2001, vol. 345, No. 19, pp. 1359-1367.

Van Den Berghe, M.D., Ph.D., et al., "Intensive Insulin Therapy in the Medical ICU", The New England Journal of Medicine, Feb. 2, 2006, vol. 354, No. 5, pp. 449-461.

Van Der Maas et al., "Requirements for Medical Modeling Languages", Journal of the American Medical Informatics Association, Mar./Apr. 2001, vol. 8, No. 2, pp. 146-162.

Villalobos et al., "Computerized System in Intensive Care medicine", Medical Informatics, vol. 11, No. 3, 1986, pp. 269-275.

Wilkins et al., "A Regular Language: The Annotated Case Report Form", PPD Inc., PharmaSUG2011—Paper CD18, 2011, pp. 1-9.

Ying et al., "Regulating Mean Arterial Pressure in Postsurgical Cardiac Patients. A Fuzzy Logic System to Control Administration of Sodium Nitroprusside", IEEE Engineering in Medicine and Biology Magazine, vol. 13, No. 5, Nov.-Dec. 1994, pp. 671-677.

Yue, Ying Kwan, "A Healthcare Failure Mode and Effect Analysis on the Safety of Secondary Infusions", Thesis, Institute of Biomaterials and Biomedical Engineering, University of Toronto, 2012, pp. 168.

Yurkonis et al., "Computer Simulation of Adaptive Drug Infusion", IEEE Transactions on Biomedical Engineering, vol. BME-34, No. 8, Aug. 1987, pp. 633-635.

Zakariah et al., "Combination of Biphasic Transmittance Waveform with Blood Procalcitonin Levels for Diagnosis of Sepsis in Acutely Ill Patients", Critical Care Medicine, 2008, vol. 36, No. 5, pp. 1507-1512.

International Search Report and Written Opinion received in PCT Application No. PCT/US2019/041715, dated Aug. 23, 2019 in 40 pages.

International Search Report and Written Opinion received in PCT Application No. PCT/US2020/031664, dated Jul. 20, 2020 in 14 pages.

Murphy, Robert, "The Design of Safety-Critical Medical Infusion Devices", May 30, 2007, Doctor of Philosopy submission, pp. 317.

Rahmani et al., "Smart e-Health Gateway: Bringing Intelligence to Internet-of-Things Based Ubiquitous Healthcare Systems", 2015 12th Annual IEEE Consumer Communications and Networking Conference (CCNC), Jul. 2015, pp. 826-834.

Sethia et al., "Security Framework for Portable NFC Mobile Based Health Record System", Oct. 2016, IEEE 12th International Conference on Wireless and Mobile Computing, Networking and Communications, pp. 1-8.

Fan et al., "Smart Medication Delivery Systems: Infusion Pumps", Supplementary Report, Healthcare Human Factors, Feb. 26, 2010, pp. 94.

* cited by examiner

*700*

702 — START DRUG LIBRARY MANAGEMENT PROCESS

704 — MANAGE MEDICATIONS

708 — MANAGE CCAs

706 — MANAGE ADMINISTRATION RULES

710 — MANAGE MEDICATIONS IN CCAs

712 — GENERATE WORKSHEET

714 — ADD CCA(s) TO WORKSHEET

716 — FINALIZE WORKSHEET

718 — GENERATE CUSTOMIZED DRUG LIBRARY DATA

720 — GENERATE GENERALIZED DRUG LIBRARY DATA

722 — DISTRIBUTE DRUG LIBRARY DATA

724 — END PROCESS

1

DRUG LIBRARY MANAGER WITH CUSTOMIZED WORKSHEETS

CROSS-REFERENCE TO RELATED APPLICATIONS

The present application is a continuation to U.S. patent application Ser. No. 16/512,243, filed on Jul. 15, 2019 and titled "Drug Library Manager with Customized Worksheets," which claims priority to International Patent Application No. PCT/US2019/041715, filed on Jul. 12, 2019 and titled "Drug Library Management System," which claims priority to U.S. Provisional Patent Application No. 62/703,772, filed on Jul. 26, 2018 and titled "Drug Library Management System," the contents of each of which are incorporated by reference herein.

TECHNICAL FIELD

This disclosure relates to the field of clinical management, and particularly to systems and methods for efficient management of drug libraries in a networked clinical environment.

BACKGROUND

Modern medical care often involves the use of medical infusion pumps to deliver fluids and/or fluid medicine to patients. Infusion pumps permit the controlled delivery of fluids to a patient and provide flexible yet controlled delivery schedules. Drug libraries within the infusion pumps provide some limits pertaining to the delivery of fluids. Infusion pumps can communicate with a server configured to manage drug library updates and operational software updates of the individual infusion pumps.

SUMMARY

Various techniques for managing drug libraries across a clinical environment and a cloud environment are described herein. These techniques may include creating and maintaining medication and administration data in a drug library database, using the data to create and maintain drug libraries, and distributing the drug libraries to various systems and components. For example, customized drug library data may be provided to infusion pumps for use in administration of medication, while generalized drug library data is proved to middleware, archives, etc. for use in system management, reporting, backup, etc. These and other embodiments are described in greater detail below with reference to FIGS. 1-10. Although many of the examples are described in the context of a hospital environment including particular infusion pumps, data formats, and the like, the techniques described herein can be applied to other types of infusion pumps, data formats, etc.

Some aspects of the present disclosure relate to a drug library management system that facilitates centralized management of the drug libraries that are used by various infusion pumps, including in clinical environments that have different types and/or versions of infusion pumps. Medications, administration rules, critical care area rules, and the like are maintained using the drug library management system, also referred to herein as the "drug library manager."

The drug library manager generates and distributes drug library data in pump-specific formats or other customized formats as needed. Therefore, different types and versions of infusion pumps, even those that use drug library data in different formats or that use different drug library data altogether, may be used in a clinical environment and managed using a single drug library management system.

BRIEF DESCRIPTION OF DRAWINGS

Throughout the drawings, reference numbers may be re-used to indicate correspondence between referenced elements. The drawings are provided to illustrate example embodiments described herein and are not intended to limit the scope of the disclosure.

DETAILED DESCRIPTION OF ILLUSTRATIVE EMBODIMENTS

Figure 1:
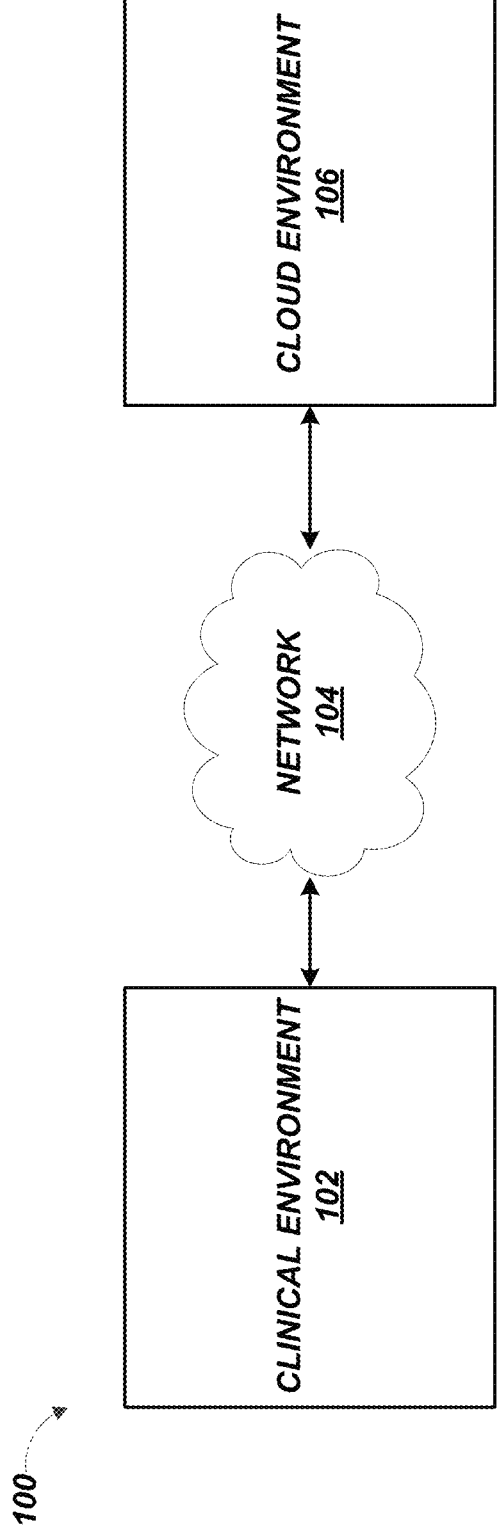
FIG. 1 is a block diagram of an example clinical environment and an example cloud environment according to some embodiments.

The present disclosure is directed to management and use of drug libraries in a networked clinical environment. The clinical environment may include various types and/or versions of infusion pumps. An infusion pump operates using a drug library that describes the medications available for administration, rules for administration of the medications, clinical care areas in which the pump may operate, and the like. Different types or versions of infusion pumps may be configured to use different formats of drug library data. In addition, it may be necessary or desirable to maintain a history of changes to the drug library data.

Some aspects of the present disclosure relate to a drug library management system that facilitates centralized management of the drug libraries that are used by various infusion pumps, including in clinical environments that have different types and/or versions of infusion pumps. Medications, administration rules, critical care area rules, and the like are maintained using the drug library management system, also referred to herein as the "drug library manager." The drug library manager generates and distributes drug library data in pump-specific formats or other customized formats as needed. Therefore, different types and versions of infusion pumps, even those that use drug library data in different formats or that use different drug library data altogether, may be used in a clinical environment and managed using a single drug library management system.

Additional aspects of the present disclosure relate to generating versions of drug library data that can be used by systems or components in the clinical environment other than infusion pumps. For example, drug library data may be used by middleware systems, reporting systems, archival systems, and the like. When a drug library is to be finalized, the drug library management system may generate a version of drug library data that is standardized or otherwise generalized, in addition to a version that is customized for the specific infusion pump(s) that use the drug library data. The generalized version of the drug library data can be used by middleware systems that process messages received from various infusion pumps, reporting systems that report data generated by or otherwise associated with various infusion pumps, etc. In addition, or alternatively, the generalized version can be archived so that historical versions of the drug library data may be available when needed (e.g., for historical reporting, for troubleshooting problems with infusion pumps when a prior version of the drug library was used, etc.). Advantageously, the generalized version may be archived separately from the drug library database used by the drug library manager, and therefore the drug library database does not need to store historical drug library data.

Although aspects of some embodiments described in the disclosure will focus, for the purpose of illustration, on particular examples of infusion pumps, medication administration rules, formats of drug library data, and the like, the examples are illustrative only and are not intended to be limiting. In some embodiments, the systems and methods described herein may be applied to additional or alternative infusion pumps, medication administration rules, drug library data formats, etc. Various aspects of the disclosure will now be described with regard to certain examples and embodiments, which are intended to illustrate but not limit the disclosure.

Overview of Example Network Environment

FIG. 1 illustrates network environment 100 in which clinical environment 102 communicates with cloud environment 106 via network 104. The clinical environment 102 may include one or more healthcare facilities (e.g., hospitals). The components of the clinical environment 102 are described in greater detail below with reference to FIG. 2. The network 104 may be any wired network, wireless network, or combination thereof. In addition, the network 104 may be a personal area network, local area network, wide area network, over-the-air broadcast network (e.g., for radio or television), cable network, satellite network, cellular telephone network, or combination thereof. For example, the network 104 may be a publicly accessible network of linked networks such as the Internet. In some embodiments, the clinical environment 102 and the cloud environment 106 may each be implemented on one or more wired and/or wireless private networks, and the network 104 may be a public network (e.g., the Internet) via which the clinical environment 102 and the cloud environment 106 communicate with each other. The cloud environment 106 may be a cloud-based platform configured to communicate with multiple clinical environments. The cloud environment 106 may include a collection of services, which are delivered via the network 104 as web services. The components of the cloud environment 106 are described in greater detail below with reference to FIG. 4.

Components of Clinical Environment

Figure 2:
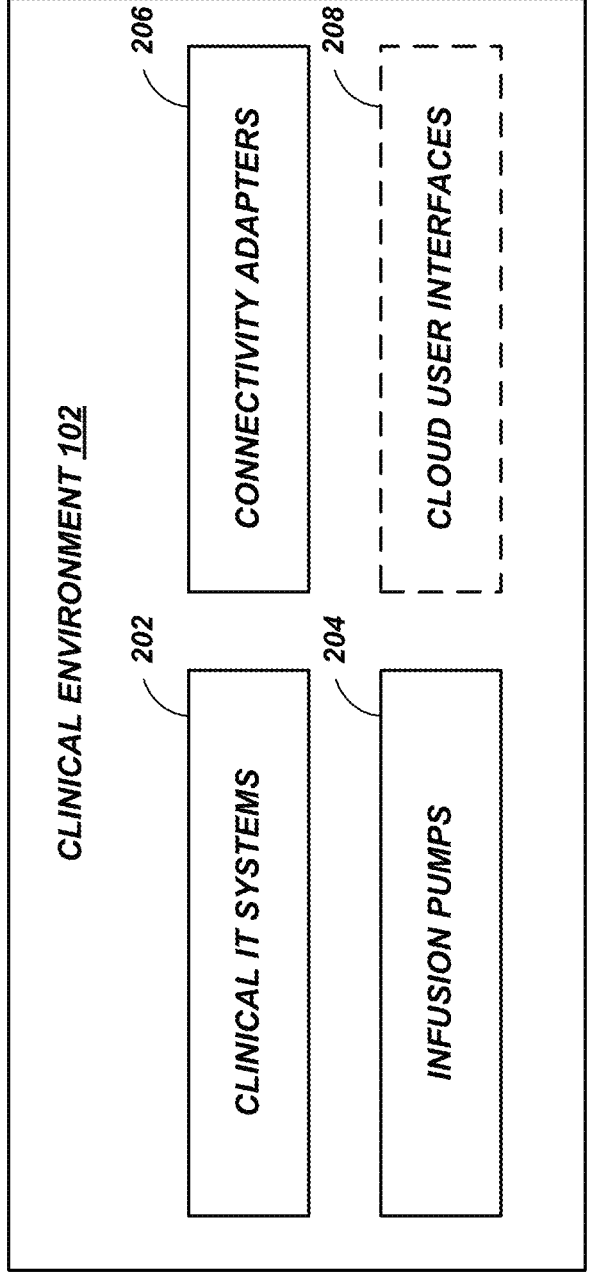
FIG. 2 is a block diagram illustrating components of a clinical environment according to some embodiments.

FIG. 2 illustrates the clinical environment 102, which includes one or more clinical IT systems 202, one or more infusion pumps 204, and one or more connectivity adapters 206. Further, the clinical environment 102 may be configured to provide cloud user interfaces 208 (e.g., generated and provided by the cloud environment 106). The clinical IT system 202 may include a hospital information system (HIS) designed to manage the facilities' operation, such as medical, administrative, financial, and legal issues and the corresponding processing of services. The HIS can include one or more electronic medical record (EMR) or electronic health record (EHR) systems, as well. The infusion pump 204 is a medical device configured to deliver medication to a patient. The connectivity adapter 206 is a network component configured to communicate with other components of the clinical environment 102 and also communicate with the cloud environment 106 on behalf of the other components of the clinical environment 102. In one embodiment, all messages communicated between the clinical environment 102 and the cloud environment 106 pass through the connectivity adapter 206. In some cases, the connectivity adapter 206 is a network appliance with limited storage space (e.g., memory and/or persistent storage). The cloud user interfaces 208 may be provided to a user in the clinical environment 102 via a browser application, desktop application, mobile application, and the like. The user may access status reports and other data stored in the cloud environment 106 via the cloud user interfaces 208.

The components 202-208 illustrated in FIG. 2 may communicate with one or more of the other components in the clinical environment 102. For example, each of the clinical IT system 202 and the infusion pump 204 may communicate with the connectivity adapter 206 via physical local area network (LAN) and/or virtual LAN (VLAN). Although not shown in FIG. 2, the clinical environment 102 may include other medical devices and non-medical devices that facilitate the operation of the clinical environment 102.

Overview of Messaging in the Clinical Environment

Figure 3:
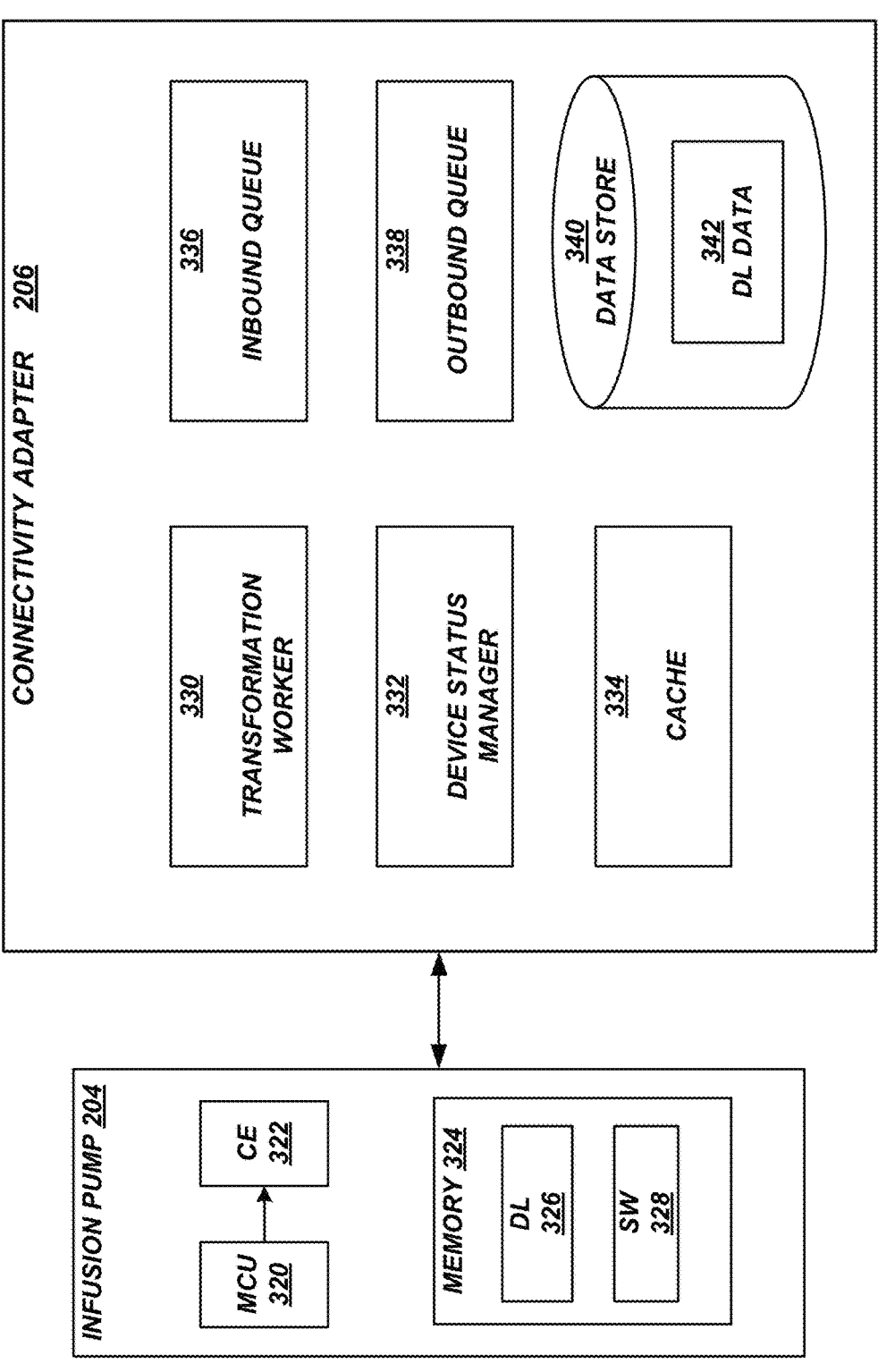
FIG. 3 is a schematic diagram illustrating components of an infusion pump and a connectivity adapter of a clinical environment according to some embodiments.

FIG. 3 illustrates the messages and data received, stored, and transmitted by the connectivity adapter 206 in the clinical environment 102. As shown in FIG. 3, the infusion pump 204 may include motor controller unit (MCU) 320 and communications engine (CE) 322, and memory 324 storing drug library data 326 and operational software 328. The drug library data 326 includes boundaries for drug delivery for various medications that can be delivered to patients by infusion pumps. The operational software 328 can include the operating system of the infusion pump 204, as well as other software for performing various functions. Each type of infusion pump and even different versions of the same type of infusion pump may operate with a different operating system. In some embodiments, the MCU 320 uses a less powerful processor (e.g., 12 MHz) and the CE 322 uses a more powerful processor (e.g., 400 MHz).

The MCU 320 may generate and send pump messages to the CE 322 for storage and transmission to the connectivity adapter 206. The pump messages may include clinical information. The CE 322 may send such pump messages to the connectivity adapter 206. Pump messages sent to the connectivity adapter 206 via the CE 322 and generated by the MCU 320 may be transformed by the transformation worker 330 into a standardized dataset message (e.g., message format used by the connectivity adapter 206 to communicate with the cloud environment 106, sometimes referred herein as simply a message). For example, the transformation worker 330 may use drug library data 342, described below, to transform a pump message into a standardized dataset message.

The CE 322 may also receive messages from the connectivity adapter 206 indicating that updates, such as updates to the drug library or updates to the operational software are available and may send messages to the connectivity adapter 206 requesting the updates (e.g., update data). The CE 322 may also receive the update data from the connectivity adapter 206 for storage in the memory 324. The update data may be drug library update data or may be operational software update data. The update data may be provided over a different communication channel than the communication channel(s) used to send or receive messages.

As also shown in FIG. 3, the connectivity adapter 206 may include transformation worker 330, device status manager 332, cache 334, an inbound queue 336, an outbound queue 338, and a data store 340. The transformation worker 330 may transform the messages sent to the connectivity adapter 206 from the infusion pump 204 into the standardized dataset message. The transformation worker 330 may also transform messages sent from the connectivity adapter 206 to the infusion pump 204 into a message format usable by the infusion pump 204.

The inbound queue 336 receives and stores messages from the cloud environment 106 for processing by the connectivity adapter 206. For example, the inbound queue 336 may receive a drug library update message from the cloud environment 106. The drug library update message may be notification that a drug library update is available for at least a portion of the infusion pumps 204 associated with the connectivity adapter 206. In an embodiment, the connectivity adapter 206 may comprise more than one inbound queue such that, for example, there is at least an inbound queue 336 for messages received from the cloud environment 106 over the network 104 and at least another inbound queue for messages received from one or more infusion pumps 204 over the local network. The messages stored in the inbound queue 336 may be associated with one or more sequence identifiers (IDs). The messages received from the cloud environment 106 may be sent over a message channel associated with the network 104.

The outbound queue 338 receives and stores messages to be sent from the connectivity adapter 206. For example, the outbound queue 338 may receive a drug library update message to be sent to one or more infusion pumps over the local network. The drug library update message may be a notification to one or more infusion pumps 204 that a drug library update is available. In an embodiment, the connectivity adapter 206 may comprise more than one outbound queue such that, for example, there is at least an outbound queue 338 for messages to be sent to the cloud environment 106 over the network 104 and at least another outbound queue for messages to be sent to one or more infusion pumps 204 over the local network. The messages stored in the outbound queue 338 may be associated with one or more sequence identifiers (IDs). The messages sent from the connectivity adapter 206 to the infusion pumps 204 may be sent over a message channel associated with the local network.

The device status manager 332 receives the drug library and operational software updates from the cloud environment 106 and caches blocks of the update data in the cache 302. The device status manager 332 processes the received messages from the inbound queue 336 and sends messages to the outbound queue 338 for transmission to the cloud environment 106 or to the infusion pumps 204. The data received from the cloud environment 106 may be sent over a data channel associated with the network 104 and separate from the message channel of the network 104. Because the data channel in the cloud environment is separate from the message channel in the cloud environment, the data transfer does not interfere with the clinical messaging from the connectivity adapter to the cloud environment. The data sent from the cache 302 to the infusion pumps 204 may be sent over a data channel associated with the local network and separate from the message channel associated with the local network. Because the data channel in the local network is separate from the message channel in the local network, the data transfer does not interfere with the clinical messaging from infusion pumps to the connectivity adapter. Thus, congestion on both the message channel of the cloud environment and the message channel of the local network is reduced.

The device status manager 332 also processes transformed messages provided by the transformation worker 330 and merges the data included in the transformed messages into the cache 334 to update the current state of the infusion pump 204 stored in the cache 334.

The data store 340 may store, among other things, drug library data 342. The drug library data 342 may be a generalized version of pump-specific drug library data that is stored on a pump 204. The drug library data 342 may be used to process messages received from a pump 204. For example, the pump 204 may send a message to the connectivity adapter 206 regarding a drug infusion process that has been initiated on the pump 204. The message may include a subset of information about the medication being infused or the infusion process, and the connectivity adapter 206 may derive information from the message. For example, the message may include an identifier of the medication that is being infused, but the message may not include the name of the medication. The connectivity adapter 206 can access the drug library data 342 and obtain the name of the medication that corresponds to the identifier received from the pump. As another example, the message may include an identifier for a clinical care area, but the message may not include the name of the clinical care area. The connectivity adapter 206 can access the drug library data 342 and obtain the name of the medication that corresponds to the identifier of the clinical care area. As a further example, the message may include a channel identifier for a particular channel of the infusion pump, a line identifier for a particular line of the infusion pump, an auto-program reference ID for a particular order number, other identifier information, some combination thereof, etc. The connectivity adapter 206 may determine a corresponding name, description, or other human-readable form from the message data using the drug library data 342. The use of the drug library data 342 to process messages received from an infusion pump 204 is described in greater detail below.

Components of Cloud Environment

Figure 4:
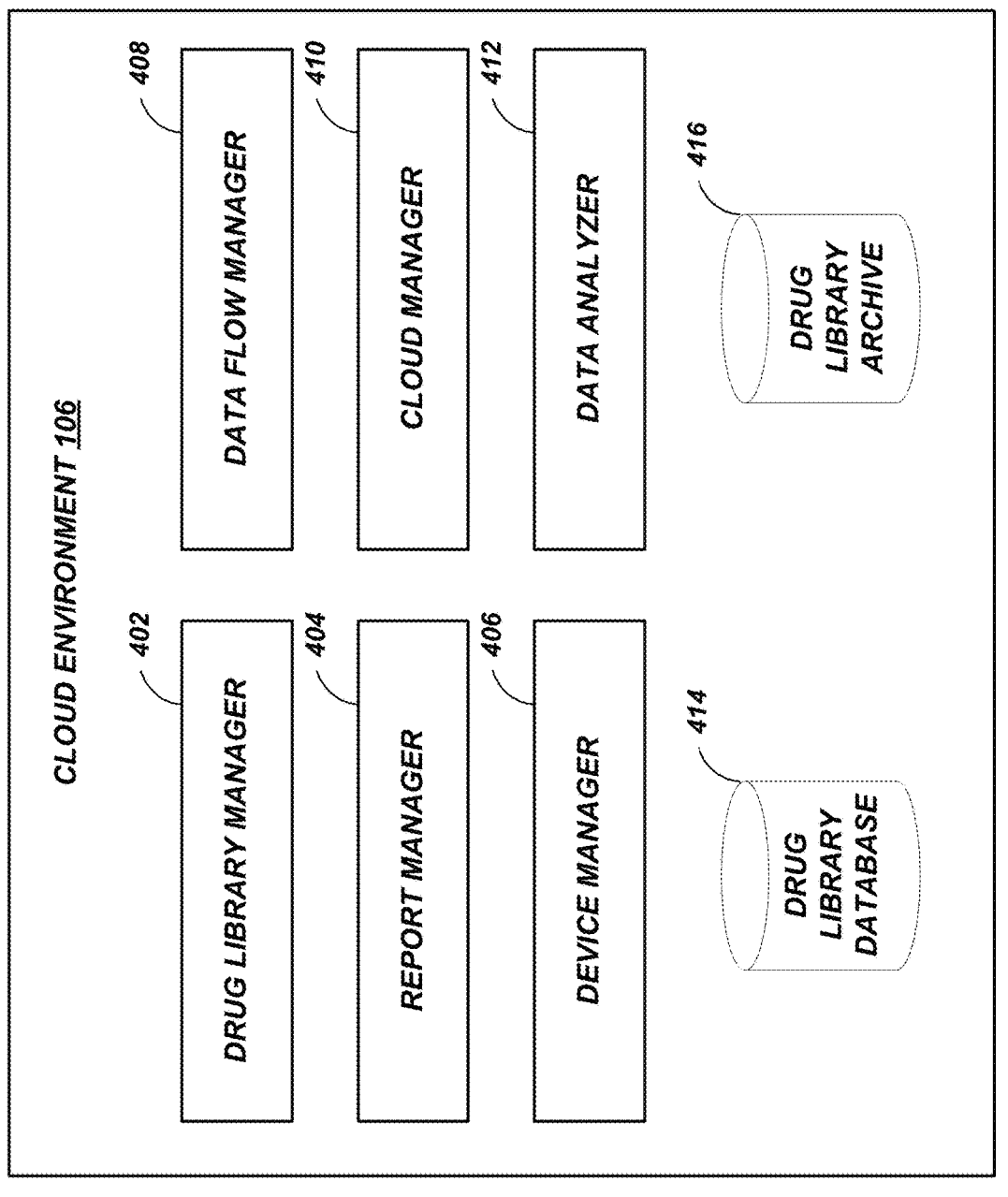
FIG. 4 is a block diagram illustrating components of a cloud environment according to some embodiments.

FIG. 4 illustrates the cloud environment 106, which includes drug library manager (DLM) 402, report manager 404, device manager 406, data flow manager (DFM) 408, cloud manager (CM) 410, data analyzer (DA) 412, a drug library database (DLDB) 414, and a drug library archive 416.

The DLM 402 may provide a set of features and functions involved in the creation and management of drug libraries for use with infusion pumps, as described in greater detail below. The drug libraries may provide user-defined settings for pump configuration and drug infusion error reduction. For example, the drug libraries may be used as part of a dose error reduction system (DERS). The report manager 404 may provide various reporting capabilities for clinically relevant infusion data which users can choose to use for further analysis, such as tracking and trending of clinical practices.

The report manager 404 may provide various reporting capabilities for clinically relevant infusion data which users can choose to use for further analysis, such as tracking and trending of clinical practices.

The device manager 406 may oversee and manage the maintenance of infusion pumps, providing users the capability to view and manage asset and operational data. For example, the device manager 406 may schedule drug library and software updates for infusion pumps.

The DFM 408 may facilitate storing, caching, and routing of data between compatible infusion pumps, compatible external systems, and the like. For example, the DFM 408 may store infusion and operational data received from infusion pumps, store and cache infusion pump drug libraries and software images, convert and route network messaging between the cloud environment 106 and the clinical environment 102, convert and route medication order information from a hospital information system to an infusion pump (e.g., auto-programming or smart-pump programming), and/or convert and route alert information and infusion events from infusion pumps to hospital information systems (e.g., alarm/alert forwarding, and auto-documentation, or infusion documentation).

The CM 410 may serve as a general-purpose computing platform for the other modules illustrated in FIG. 4. Functionally, the CM 410 may be similar to Microsoft Windows or Linux operating systems as it provides the following services: networking, computation, user administration and security, storage, and monitoring.

The DA 412 may provide data analytics tools for generating user interfaces and reports based on the data generated and/or received by the other modules illustrated in FIG. 4.

The DLDB 414 may store data regarding medications, medication administration rules, clinical care areas, and other data maintained and used by the drug library manager 402 to generate drug library data for infusion pumps and other systems or components.

The drug library archive 416 may store generalized drug library data that has been generated by the drug library manager 402. The drug library archive 416 may store a copy of every generalized drug library data set generated by the drug library management, or some subset thereof, for use in record keeping, reporting, etc. Use of archived generalized drug library data is described in greater detail below.

Although not illustrated in FIG. 4, the cloud environment 106 may provide other resources such as processors, memory, disk space, network, etc. The modules 402-412 may be hardware components configured to perform one or more of the techniques described herein. Alternatively, the modules 402-412 may be implemented using software instructions stored in physical storage and executed by one or more processors. Although illustrated as separate components, the modules 402-412 may be implemented as one or more hardware components (e.g., a single component, individual components, or any number of components), one or more software components (e.g., a single component, individual components, or any number of components), or any combination thereof.

In some embodiments, the cloud environment 106 can be implemented using a commercial cloud services provider (e.g., Amazon Web Services®, Microsoft Azure®, Google Cloud®, and the like). In other embodiments, the cloud environment 106 can be implemented using network infrastructure managed by the provider and/or developer of the modules 402-412 shown in FIG. 4. In some embodiments, the features and services provided by one or more or the modules 402-412 may be implemented on one or more hardware computing devices as web services consumable via one or more communication networks. In further embodiments, one or more of the modules 402-412 are provided by one or more virtual machines implemented in a hosted computing environment. The hosted computing environment may include one or more rapidly provisioned and released computing resources, such as computing devices, networking devices, and/or storage devices.

Overview of Drug Library Management System

Figure 5:
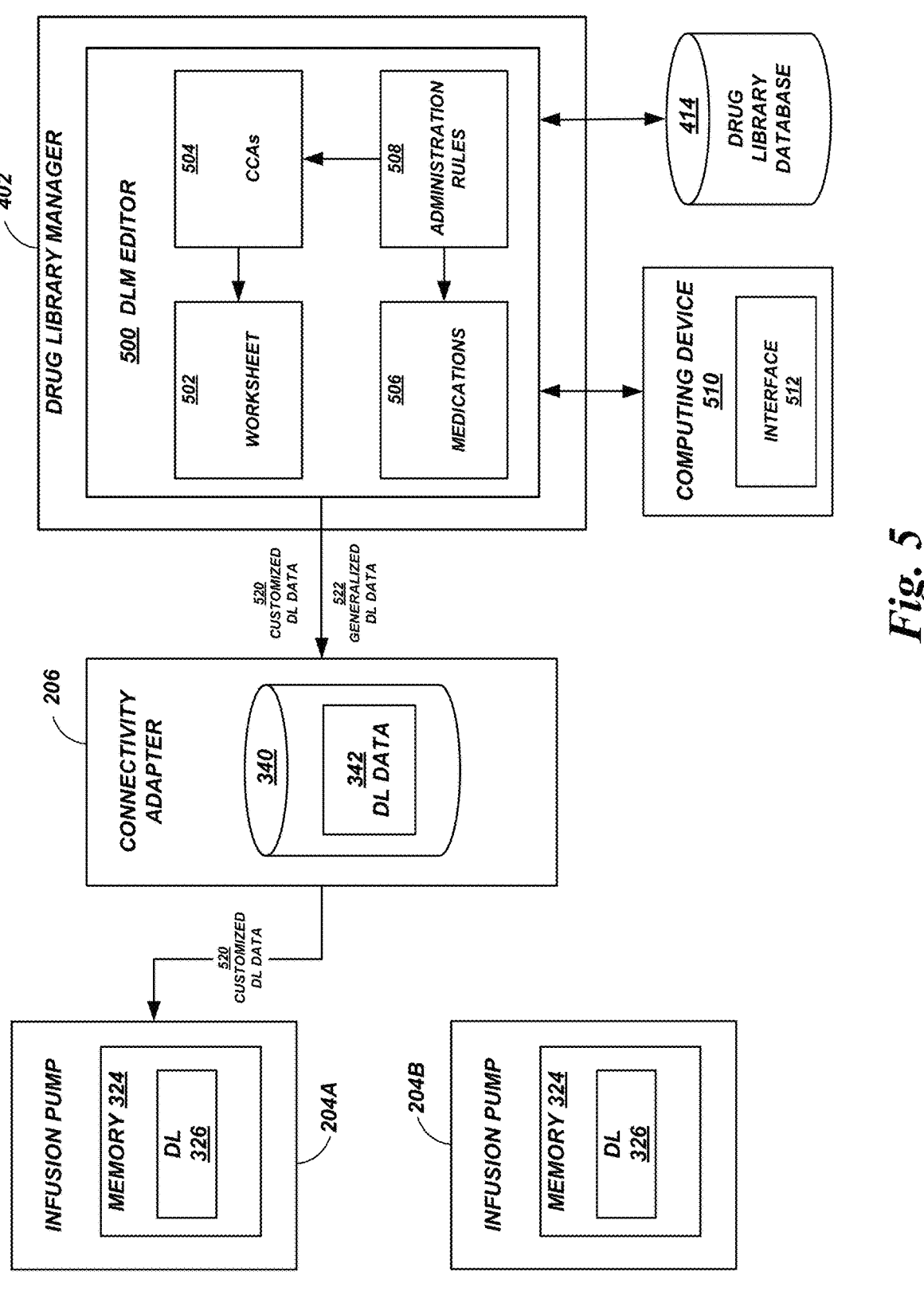
FIG. 5 is a block diagram of various data flows and interactions between a drug library manager, an end user device, an infusion pump, and various other system components during the creation and distribution of drug libraries according to some embodiments.

With reference to an illustrative embodiment, FIG. 5 shows a network environment in which aspects of drug library management may be implemented. As shown, a DLM 402 may include a DLM editor 500 component. The DLM editor 500 may include executable instructions that generate a user interface 512 for display on an end-user computing device 510. For example, the DLM may include, or be associated with, a web server that generates web pages, sends the web pages to the end-user computing device 510, and processes user inputs and interactions with the web pages.

The DLM editor 500 may be used to manage data stored in the DLDB 414, and to generate drug library data for use by various devices and systems, such as infusion pumps 204A, 204B, and the connectivity adapter 206. The data to be stored in the DLDB 414 may include data regarding medications 506, administration rules 508 regarding use of the medications 506, clinical care areas (CCAs) 504 in which medications are used, and other data related to the management of drug libraries.

In some embodiments, the DLDB 414 may include data related to the management of all drug libraries associated with the cloud environment 106. In other embodiments, the DLDB 414 may include data related to a subset of drug libraries associated with the cloud environment 106 (e.g., drug libraries for a particular clinical environment 102 or group of clinical environments, drug libraries for a particular customer or other entity, etc.). For example, there may be multiple DLDBs that are physically or logically separate from each other.

Medications 506 are data entities that represent medications that can be administered via an infusion pump. In some embodiments, a medication 506 data entity may include data regarding a name of a medication, an identifier of the medication (e.g., a unique identifier used by an HIS), an indication of whether the medication is a high-risk medication, and/or other information.

Administration rules 508 are data entities that represent the parameters by which a medication may be administered. For example, an administration rule 508 for a particular medication may include data representing various medication administration parameters such as a dosing unit, a clinical use, and/or other information. In some embodiments, an administration rule 508 for a particular medication 506 may include medication administration parameter data regarding an absolute or "hard" minimum and/or maximum limit to the administration of the medication (e.g., minimum or maximum amount that may be administered overall or in a period of time, minimum or maximum rate at which the medication may be administered, etc.). Such hard limits typically cannot be overridden. In some embodiments, the administration rule 508 may also or alternatively include data regarding a recommended or "soft" minimum and/or maximum limit to administration of the medication. Such soft limits may be overridden (e.g., by users with the proper level of authority, after generation of an alert such as an audible and/or visual notification, etc.). There may be any number of administration rules 508 for a single medication 506. For example, different administration rules 508 may be separately maintained for different clinical uses of the same medication 506, different infusion pumps 204 through which the medication is to be administered, and/or different CCAs 504 in which the medication is to be administered. In some embodiments, a medication 506 may be associated with zero or more administration rules 508. In some embodiments, an administration rule may only be associated with a single medication 506.

CCAs 504 are data entities that represent organizational units of health care enterprises. For example, CCAs may represent hospitals, individual hospital facilities, departments, or lines of care. In some embodiments, a CCA corresponds to a unit of similar clinical uses, patient types, other characteristics, some combination thereof, etc. CCAs 504 may be associated with various medications 506 and administrative rules 508.

Figure 6:
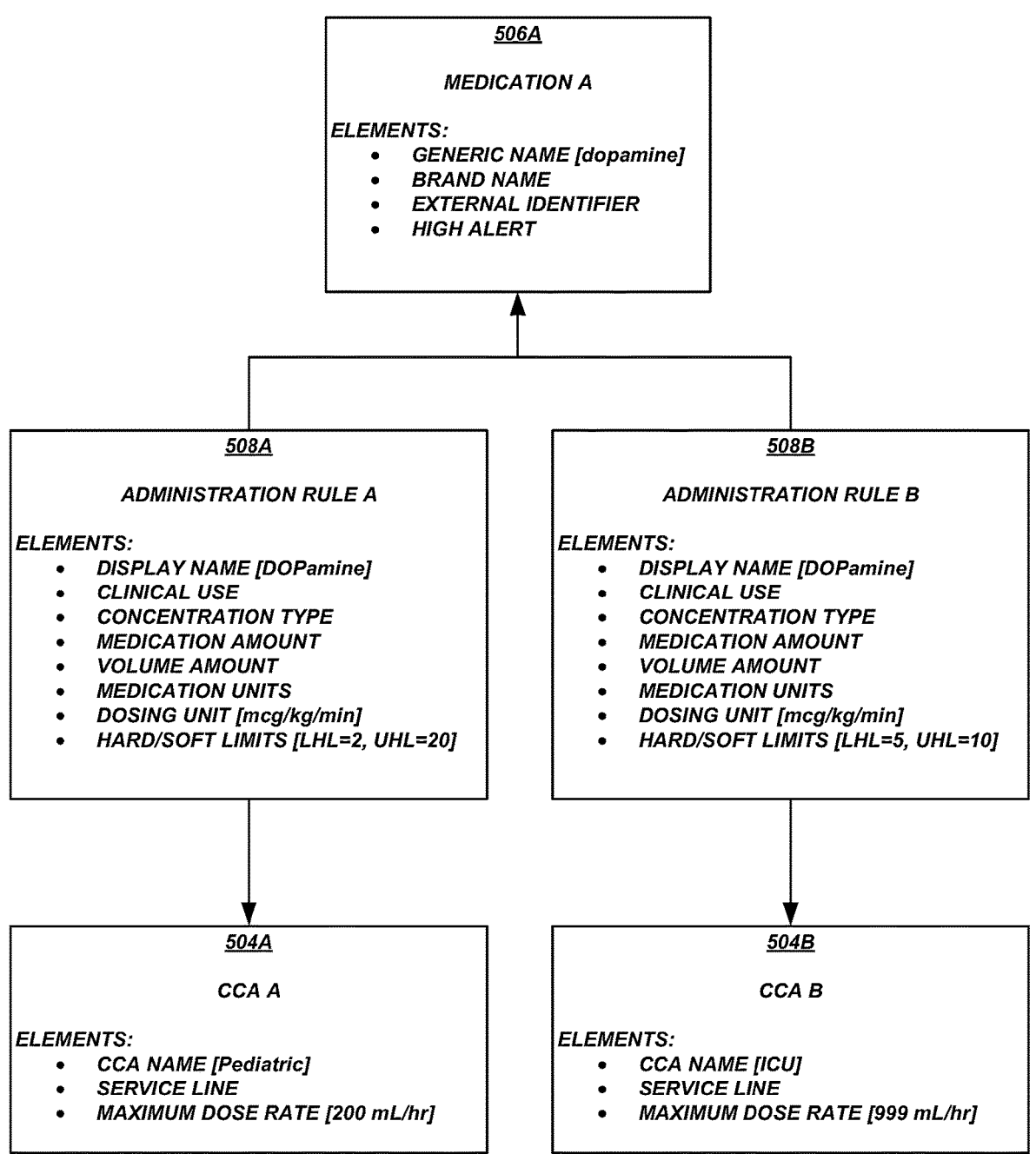
FIG. 6 is a block diagram of illustrative components of a drug library according to some embodiments.

FIG. 6 shows an example of a medication 506A associated with multiple administration rules 508A and 508B. The administration rules 508A and 508B are associated with different CCAs 504A and 504B respectively. CCA 504A may correspond to a pediatric unit of a hospital, and CCA 504B may correspond to an ICU of the hospital. The pediatric CCA 504A and ICU 504B may each have various data elements, any or all of which may correspond to medication administration settings. For example, as shown, pediatric CCA 504A may include a data element specifying a maximum dose rate of 200 mL/hr. ICU CCA 504B may include a data element specifying a maximum dose rate of 999 mL/hr. Pediatric CCA 504A may be associated with an administration rule 508A for medication 506A, and that administration rule 508A is more restrictive (e.g., smaller maximum doses) than the administration rule 508B—for the same medication 506A—that is associated with ICU CCA 504B, which is for an adult population. In some embodiments, settings for the pediatric CCA 504A may prevent or override a less restrictive administration rule 508A when the medication 506A is used within the pediatric CCA 504A. However, if the administration rule 508A for the medication 506A is more restrictive than a setting of the pediatric CCA 504A, the setting of the CCA 504A will not override the administration rule 508A.

Returning to FIG. 5, a user may use the DLM editor 500 to organize medications, administration rules, and CCAs into drug libraries that are distributed to infusion pumps and other system components. In some embodiments, the organizational mechanism may be referred to as a worksheet 502. A worksheet 502 is a dataset that includes references to the individual medications and administration rules to be made available to infusion pumps. In addition, the worksheet 502 can be directed to a particular infusion pump 204 or group of infusion pumps 204 that share the same customized drug library data format. Rather than providing data to the infusion pump 204 regarding every medication 506 and administration rule 508 available in the DLDB 414, a worksheet 502 may be used to specify a subset of medications 506 and administration rules 508. For example, a CCA 504 may be added to a worksheet 502, and all of the medications 506 and administration rules 508 associated with the CCA 504 and the target infusion pump 204 are automatically added. In some embodiments, individual medications may optionally be added to a worksheet separately from any CCA that may be added.

The worksheet 502 dataset may be stored in the DLDB 414. The worksheet 502 dataset may include data representing various properties of the worksheet, such as a name, infusion pump type and/or version targeted by the worksheet, creator of the worksheet, creation and/or edit date, approval status, version, and the like. In addition, the worksheet 502 dataset may include a collection of pointers or other references to the data entities representing the various CCAs, medications, and administration rules that are associated with the worksheet 502. Creation of worksheets 502 and other associated operations are discussed in greater detail below.

The DLM editor 500 or some other component of the DLM 402 can generate drug library data using a worksheet 502. For example, once a worksheet 502 has been created or edited, the worksheet 502 may be in a "pending" status, awaiting approval. After the appropriate approval has been granted, the DLM 402 can generate customized drug library data 520 that represents the CCAs, medications, administration rules, and other data in the format that is required for operation of the target pump 204. In addition, the DLM 402 can generate generalized drug library data 522 for use by a middleware component such as the connectivity adapter 206, for reporting and archival purposes, etc.

As shown in FIG. 5, the DLM 402 can send the customized drug library data 520 and generalized drug library data 522 to a connectivity adapter 206 that is in communication with multiple infusion pumps 204A, 204B. The connectivity adapter 206 can store the generalized drug library data 522 in the data store 340. The generalized drug library data 522 may be incorporated into the drug library data 342 as the generalized drug library data that corresponds to the customized drug library data 520 that has also been or soon will be received.

The CA 206 can provide the customized drug library data 520 to the appropriate infusion pump 204A, or instruct the appropriate infusion pump 204A to obtain the customized drug library data 520. The infusion pump 204A can store the customized drug library data 520 in memory 324 for use in future operation. For example, the infusion pump 204A may replace customized drug library data 326 currently in memory with the newly-received customized drug library data 520.

Other infusion pumps, such as those that do not operate using the same format of customized drug library data, are not provided with or instructed to obtain the customized drug library data 520. For example, infusion pump 204B may be a different type of infusion pump than infusion pump 204A, or may be a different version of infusion pump 204A that is not compatible with the customized drug library data 520. In this example, infusion pump 204B is not provided with the customized drug library data 520. As another example, infusion pump 204B may be located in a location that is associated with a different CCA than infusion pump 204A. The customized drug library data 520 may be targeted at the CCA with which infusion pump 204A is associated, but not the CCA with which infusion pump 204B is associated. In this example, infusion pump 204B is not provided with the customized drug library data 520. Details and examples of the drug library update process are described in greater detail in a co-pending international patent application no. PCT/US2019/041705, titled "UPDATING INFUSION PUMP DRUG LIBRARIES AND OPERATIONAL SOFTWARE IN A NETWORKED ENVIRONMENT" and filed Jul. 12, 2019, which is incorporated by reference herein.

The worksheet structure allows for comparison among different versions of drug library data selected for a particular subset of CCAs and infusion pumps. For example, a worksheet that is being edited can be compared to a current version of the worksheet and/or one or more historical versions of the worksheet. The various versions of the worksheet—and therefore the various versions of the corresponding drug library data—may be stored as generalized drug library data (e.g., JavaScript Object Notation or JSON files) and may be compared to each other (e.g., using text-based comparison methods) to determine any differences between the files. Differences between the files may be presented to a user so that the user can see what is different between the versions of the drug library data. These storage and comparison methods are generally more efficient than storing multiple versions of each individual record of drug library data in the DLDB along with corresponding effective dates, indicators of active/inactive status, and the like.

The worksheet structure also allows users to build specific drug libraries for specific purposes from a shared dataset. For example, a first worksheet designed for a cancer center utilizes a first subset of the overall DLDB, while a second worksheet designed for a pediatric center utilizes a second subset of the overall DLDB that is different than the first subset. The individual records for the CCAs, medications, and administration rules may be maintained in the DLDB without being changed for the different worksheets. The worksheet datasets for the different worksheets may be modified in the DLDB, and may reference data for the CCAs, medications, and administration rules.

The worksheet structure facilitates maintaining and viewing lifecycle of a particular set of drug library data. For example, a particular set of drug library data, corresponding to a particular worksheet, may progress through various stages, including: editable, in review, active, and archived. Data regarding each of the states may be included in the worksheet dataset. Accordingly, the worksheet structure provides revision control for each set of drug library data independently from other sets of drug library data (as managed using other worksheets).

The worksheet structure also facilitates identification and implementation of global changes that are to be cascaded to all worksheets. For example, when two worksheets contain a particular CCA and that CCA is updated (e.g., a new administration rule is added, a limit is changed, etc.), then both worksheets may automatically incorporate the changes made to CCA by virtue of the worksheets referencing the CCA data that has been changed rather than including a copy of CCA as it previously existed. As another example, when a worksheet's dataset has been updated, the system can notify health care professionals that new drug library data may need to be finalized to incorporate the changes for use on infusion pumps.

Example Drug Library Management Process

Figure 7:
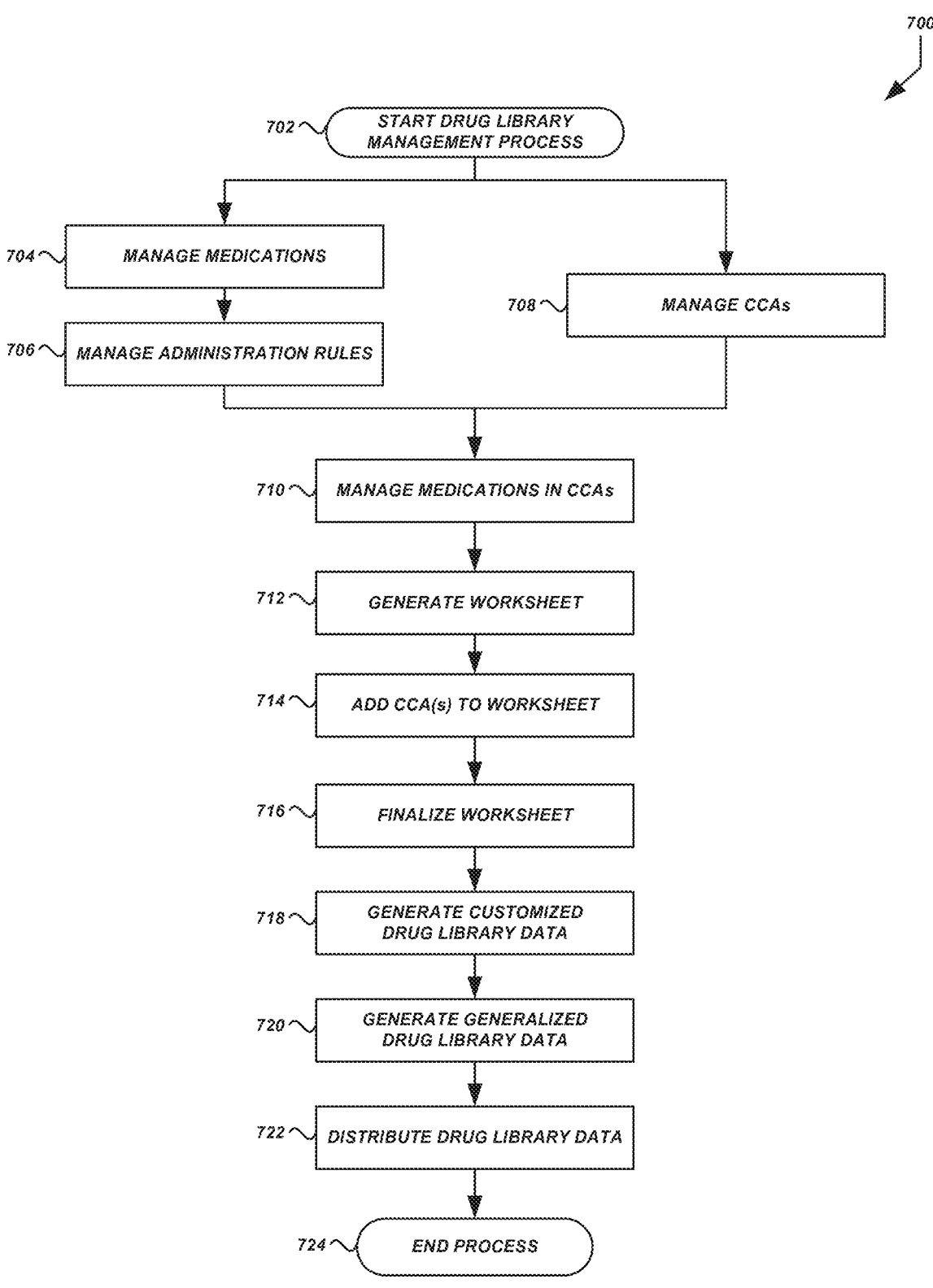
FIG. 7 is a flow diagram of an illustrative process for managing the creation, maintenance, and distribution of drug libraries according to some embodiments.

FIG. 7 is a flow diagram of an illustrative process 700 that may be executed by a DLM Editor 500 or some other component of the DLM 402 to manage the creation and maintenance of data in the DLDB 414, and the creation and maintenance of drug libraries for use by infusion pumps 204, connectivity adaptors 206, reporting systems, archival systems, and the like. Advantageously, the process 700 facilitates the maintenance of DLDB data in a streamlined manner, such that data regarding, medications, administration rules, CCAs, and the like needs to be created or edited only once, and the changes will be reflected across all associated drug libraries. Moreover, the process 700 provides the creation of generalized drug library data that may be archived in addition to being used by other systems or components. Thus, a repository of archived generalized drug library data files can provide snapshots of the state of drug libraries at various points in time, without requiring the maintenance of out-of-date data in the DLDB. Portions of the process 700 will be described with reference to the diagram of illustrative data flows and interactions shown in FIG. 5, and the diagrams of illustrative user interfaces shown in FIGS. 8 and 9.

The process 700 shown in FIG. 7 begins at block 702. The process 700 may begin in response to an event, such as when the DLM editor 500 begins execution. When the process 700 is initiated, a set of executable program instructions stored on one or more non-transitory computer-readable media (e.g., hard drive, flash memory, removable media, etc.) may be loaded into memory (e.g., random access memory or "RAM") of a computing device of the cloud environment 106. The executable instructions may then be executed by a hardware-based computer processor (e.g., a central processing unit or "CPU") of the computing device. In some embodiments, the process 700 or portions thereof may be implemented on multiple processors, serially or in parallel.

At block 704, the DLM editor 500 or some other component of the DLM 402 can manage medications in the DLDB 414. Management of medications may include creating, viewing, updating, and/or deleting medication 506 data entities.

In some embodiments, a user may use an end-user computing device 510 to access the DLM editor 500, as shown in FIG. 5. The end-user computing device 510 may present an interface for management of medications in the DLDB 414. For example, the DLM editor 500 may provide interface 800, shown in FIG. 8, to manage a particular medication 506. Interface 800 includes an infusion pump selection area 802, a medication information entry area 804, a dosing limitations entry area 806, and a clinical care area selection control 808.

The user may use the infusion pump selection area 802 to select the infusion pump(s) and/or pump version(s) which may be used to administer the medication. The user may use the medication information entry area 804 to manage properties of the medication. For example, identification-related properties such as a generic drug name 840 and display name 841 may be entered. A clinical use 842 may also be entered. Medication amount 843, volume amount 844, medication unit 845, and concentration type may also be entered.

In some embodiments, a single medication may be associated with different display names. For example, an infusion pump may only support a limited number of characters for display of medication names. Because the length of some medication names may exceed the character limit, a shortened name, such as a brand name, abbreviation, or the like may be used. Additionally, or alternatively, emphasis may be applied to portions of medication names for display to help avoid errors in the administration of the medications. Illustratively, the display name may be entered using "tall man" lettering in which part of a medication's name is displayed in upper case letters to help distinguish it from other medication names that may look and/or sound similar (e.g., "prednisone" and "prednisolone" may be displayed as "predniSONE" and "predniSOLONE").

A subset of the information in the various entry areas may corresponds to an administration rule for the medication, indicated by administration rule data entry group 810. In some embodiments, additional and/or alternative information in the various entry areas may be part of a particular administration rule. For example, an administration rule may be assigned to a single infusion pump and/or pump type, and therefore the infusion pump selection area 802 may be included in the administration rule data entry group 810. As another example, an administration rule may not include a specific display name for the medication, and therefore administration rule data entry group 810 may not include display name 841, or display name 841 may be optional.

In some embodiments, a single medication may also or alternatively be associated with different clinical uses, amounts, volumes, units, and/or concentration types. Additional medication entries—corresponding to different database records, different presentations of the interface 800, etc.—may be used to capture these different combinations of properties. However, each of the medication entries can be linked to the top-level medication (e.g., as identified by a generic medication name and a unique identifier). In this way, the medication and all of its different available combinations of properties can be treated as a single unit when desired, or as separate medication entities when desired.

Returning to FIG. 7, at block 706 the DLM editor 500 or some other component of the DLM 402 can manage administration rules in the DLDB 414. Management of administration rules may include viewing and/or updating deleting medication 506 data entities.

Figure 8:
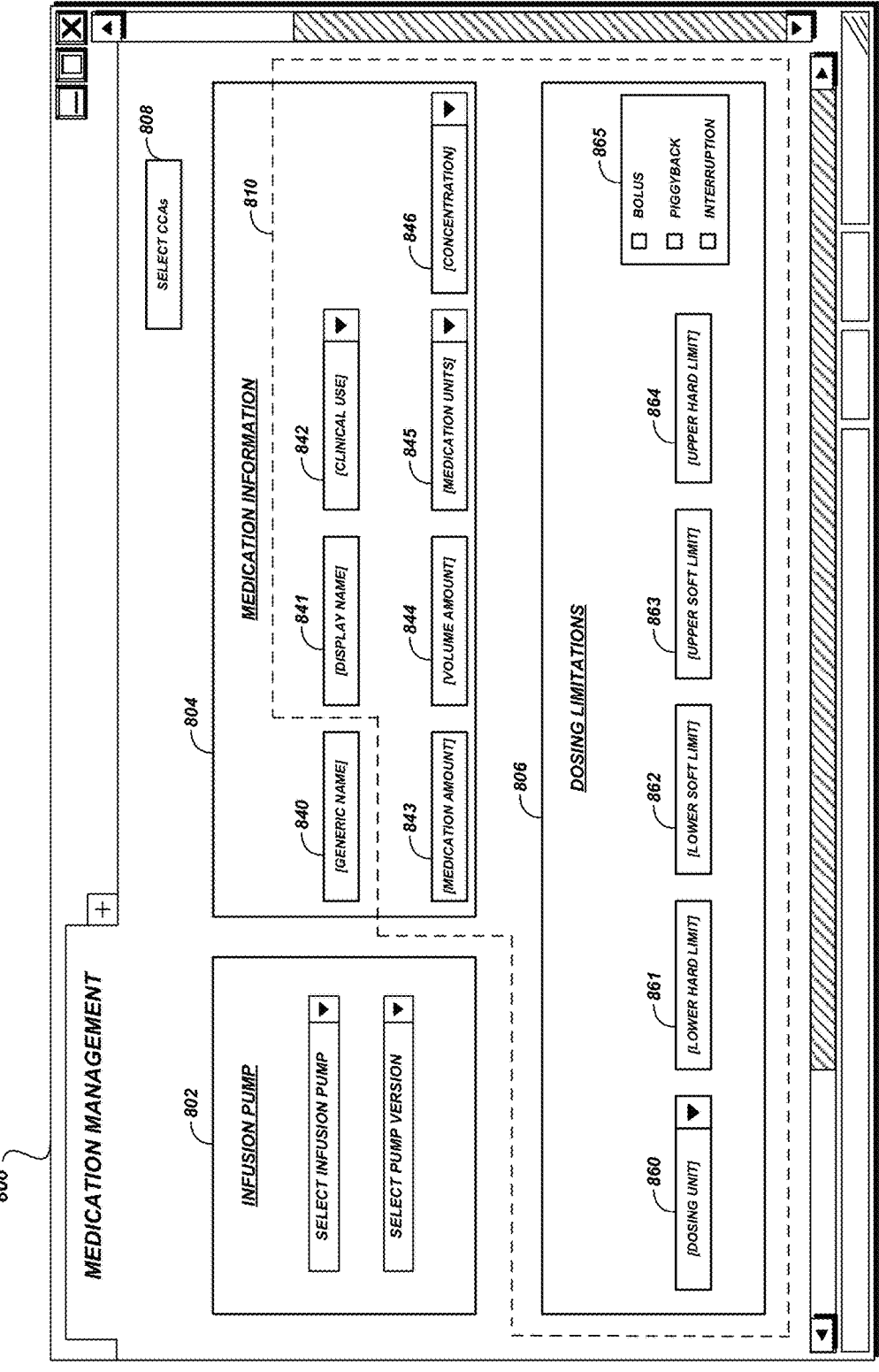
FIG. 8 is a user interface diagram of an illustrative interface for creating and maintaining medication and administration data according to some embodiments.
Figure 9:
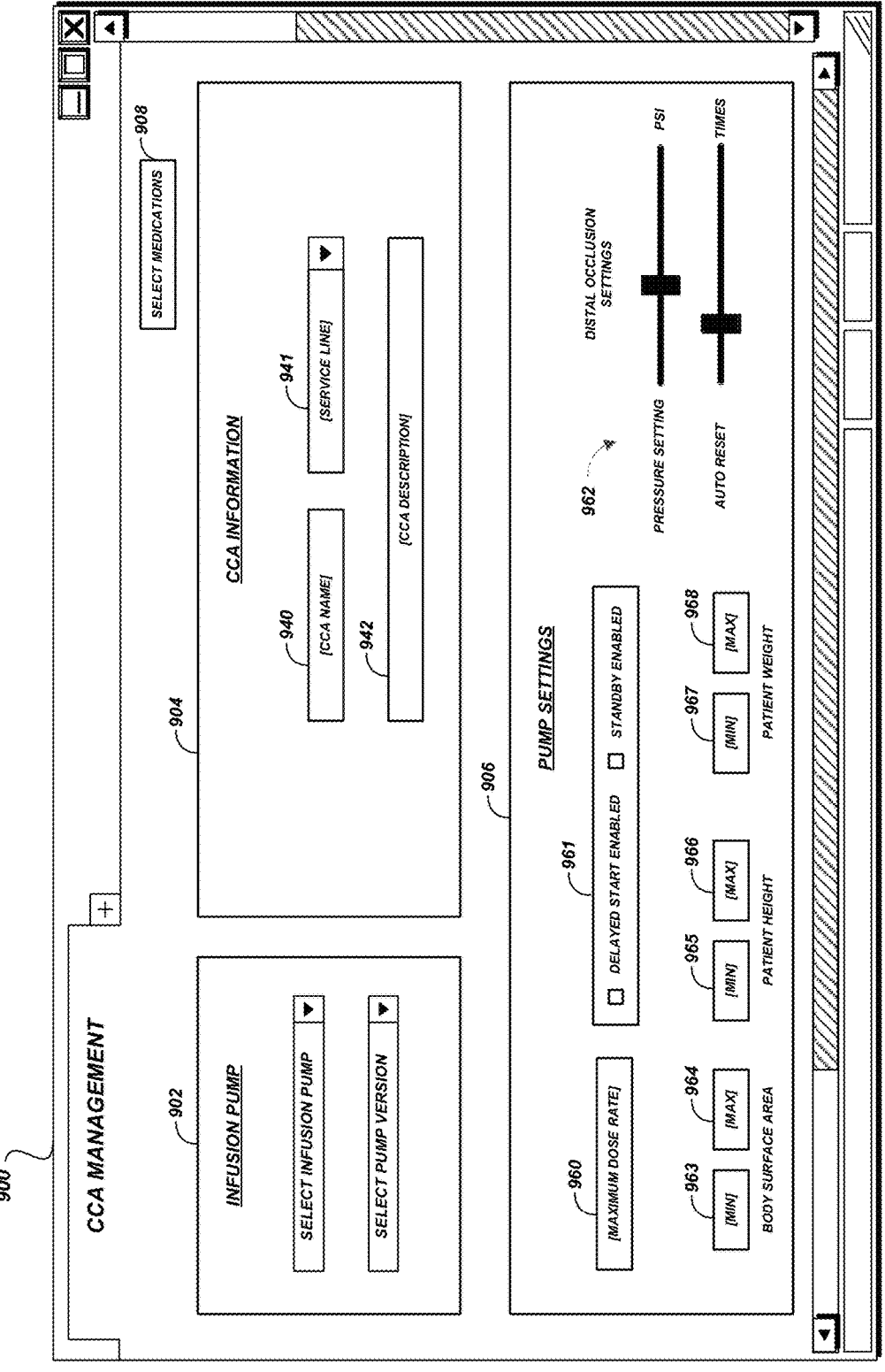
FIG. 9 is a user interface diagram of an illustrative interface for creating and maintaining organizational information according to some embodiments.

In some embodiments, a user may use interface 800, shown in FIG. 8, to manage administration rules for a particular medication 506. In addition to identification and other properties of a medication 506 as described above, the interface 800 includes a dosing limitations entry area 806. The dosing limitations entry area 806 may be used to specify various administration limits, permissions, and the like. The data provided in these fields is then incorporated into the drug library for the selected infusion pump, and serves to constrain the manner in which the medication is permitted to be administered by the infusion pump. For example, after specifying a dosing unit 860, a user may enter a lower hard limit 861, lower soft limit 862, upper soft limit 863, and/or upper hard limit 864, all in terms of the selected dosing unit. An infusion pump that is administering the medication subject to this administration rule will not be permitted to administer an amount outside the hard lower and upper limits. The infusion pump may be permitted to administer an amount outside the soft lower and upper limits, but before doing so the infusion pump may be required to perform various procedures, such as initiating alerts, prompting for authorization, or the like.

Additional administration techniques 865, such as bolus administration, piggyback delivery, piggyback interruption, and the like may be permitted or blocked. Some administration techniques may be associated with their own properties, and permission of such techniques may cause display of additional data entry areas or interfaces. For example, if bolus administration is permitted in the additional administration techniques 865 section, then additional fields for dosing unit, upper and lower hard/soft limits, and the like may be shown.

In some embodiments, multiple administration rules 508 may be associated with a single medication 506. For example, different administration rules may be used for different infusion pumps. As another example, different administration rules may be associated with different clinical uses or concentrations of the medication. In these cases, additional medication entries may be added for the medications, and the different administration rules may be created accordingly. However, each of the separate medication entries and corresponding administration rules may be associated with a single top-level medication 506 data entity.

Returning to FIG. 7, at block 708 the DLM editor 500 or some other component of the DLM 402 can manage CCAs in the DLDB 414. Management of CCAs may include creating, viewing, updating, and/or deleting CCA 504 data entities. In some embodiments, a user may use a remote computing device 510 that presents an interface for management of CCAs in the DLDB 414. For example, the DLM editor 500 may provide interface 900, shown in FIG. 9, to manage a particular CCA 504.

Interface 900 includes an infusion pump selection area 902, a CCA information entry area 904, a pump settings entry area 906, and a medication selection control 908. A user may use the infusion pump selection area 902 to select the infusion pump(s) and/or pump version(s) which may be used to administer medication in the CCA. The user may use the CCA information entry area 904 to manage properties of the CCA. For example, identification-related properties such as a CCA name 940, service line 941, and CCA description 942 may be entered. The user may use the pump settings entry area 906 to manage CCA-specific settings for the selected pump(s), such as pump limits and other operational settings of the pump(s) in the CCA. For example, the user may provide a maximum dose rate 960, permit or prohibit additional administration functions 961 such as delayed start or standby, and set occlusion alarm settings 962. In some embodiments, the user may enter CCA-specific patient limits used to constrain which patients are permitted to be treated using the infusion pump on the CCA. For example, patient limits may include minimum body surface area (BSA) 963, maximum BSA 964, minimum height 965, maximum height 966, minimum weight 967, maximum weight 968, and the like.

Although FIG. 7 illustrates blocks 704 and 706 occurring in a sequential manner on one execution path, and block 608 occurring in a parallel execution path, this example is illustrative only. In some embodiments, the operations that correspond to blocks 704, 706, and 708 may be performed sequentially, asynchronously, in parallel, or individual blocks may be repeated as needed.

At block 710, the DLM editor 500 or some other component of the DLM 402 can manage the medications available to the CCAs in the DLDB 414. For example, interface 800 for a particular medication 506 includes a clinical care area selection control 808. A user can activate this control 808 to access an interface that facilitates selection of CCAs in which the medication 506 is permitted to be administered. As another example, interface 900 for a particular CCA 504 includes a medication selection control 908. A user can activate this control 908 to access an interface that facilitates selection of medications that are permitted to be administered in the CCA 504.

At block 712, the DLM editor 500 or some other component of the DLM 402 can generate a worksheet 502 for management of a drug library. The worksheet 502 provides the mechanism by which a drug library is generated for use by an infusion pump. Separate drug libraries may be generated and maintained for different infusion pumps and/or infusion pumps in different facilities, CCAs, and the like. In some embodiments, a user may use a remote computing device 510 that presents an interface for management of worksheets in the DLDB 414. The user may enter worksheet-specific information, such as a name for the worksheet, an infusion pump type and/or version targeted by the worksheet, and the like. Data representing the worksheet-specific information may be stored in the DLDB 414.

At block 714, the DLM editor 500 or some other component of the DLM 402 can add one or more CCAs 504 to the worksheet 502. Addition of CCAs 504 also has the effect of adding the various medications 506 and administration rules 508, associated with the CCAs 504, to the worksheet 502. In this example, the CCAs provide the organizational means by which groups of medications may be added to a particular worksheet and therefore to a particular drug library.

In some embodiments, the DLM editor 500 or some other component of the DLM 402 can add one or more medications 506 to the worksheet 502. Addition of medications 506 to the worksheet 502 may also have the effect of adding various administration rules 508, associated with the medications 506, to the worksheet 502. In some embodiments, medications may be added in addition to CCAs, or medications may be added individually without the addition of CCAs to the worksheet. At block 716, the DLM editor 500 or some other component of the DLM 402 can finalize the worksheet 502. The worksheet 502 may be finalized on-demand (e.g., immediately upon request by a user of the DLM editor 500), or it may be subject to an authorization workflow. For example, the user may request finalization of a worksheet after various changes have been made. Other users may then access the worksheet, view the changes if desired, and approve or reject the worksheet. Once the changes to the worksheet are approved, the worksheet may be finalized.

At block 718, the DLM editor 500 or some other component of the DLM 402 can generate customized drug library data using the worksheet 502. As described above, the worksheet may specify a particular pump type or version to which the worksheet applies. The DLM 402 can use drug library specification data for the particular infusion pump type or version to generate customized drug library data of the pump.

Drug library specification data may include rules for generating customized drug library data required by the infusion pump, such as the data structure and format in which the drug library data is expected to be delivered, functions or other transformations to be applied to data from DLDB 414 to produce data that is able to be used by the infusion pump, etc. For example, a first type of infusion pump may expect data fields a, b, c, d, and e to be present, in that sequence, for each medication record. A second type of infusion pump may also expect fields a, b, and c, to be present, together with data that corresponds to field d with a mathematical transformation applied, and also a different field f instead of field e. In addition, the second type of infusion pump may expect the fields to be in a different sequence than the first type of infusion pump. The drug library specification data for the two different types of infusion pumps can provide data regarding these expected data fields, formats, transformations, sequences, and the like.

The DLM 402 can determine which infusion pump type and/or version is specified in the worksheet 502 data set. The DLM 402 can then generate customized drug library data 520 for the infusion pump using the worksheet 502 data in the DLDB 414 and the drug library specification data for the infusion pump.

At block 720, the DLM editor 500 or some other component of the DLM 402 can generate generalized drug library data using the worksheet 502. As described above, the generalized drug library data is data used by middleware components (e.g., connectivity adapters 206), reporting systems, archival systems, and the like. Each of these different devices and components may be configured to operate using the same generalized drug library data. Illustratively, the generalized drug library data may be created in a standardized data format, such as JavaScript Object Notation (JSON), eXtensible Markup Language (XML), or the like. In some embodiments, generalized drug library specification data may be used to generate the generalized drug library data. Generalized drug library specification data may include rules for generating the generalized drug library data, such as the data structure and format in which the generalized drug library data is to be delivered, the functions or other transformations to be applied to data from the DLDB 414 to produce the generalized drug library data, etc. The DLM 402 can generate the generalized drug library data using the worksheet 502 data in the DLDB 414 and the generalized drug library specification data.

Although FIG. 7 illustrates blocks 718 and 720 occurring in a sequential manner on one execution path, this example is illustrative only. In some embodiments, the operations that correspond to blocks 718 and 720 may be performed in a different sequence, asynchronously, or in parallel.

At block 722, the DLM editor 500 or some other component of the DLM 402 can distribute the drug library data generated above. For example, as shown in FIG. 5, the DLM 402 can provide the generalized drug library data 522 and customized drug library data 520 to a connectivity adapter 206. In some embodiments, the DLM may also or alternatively store the generalized drug library data in a drug library archive 416. Storage of generalized drug library data 522 in the drug library archive 416 can provide certain benefits, such as the ability to access the drug library, as it existed when generated, at some future time even after other intervening versions of the drug library have been generated. In addition, by maintaining prior versions of drug libraries in the separate archive 416, the size and complexity of the DLDB 414 may be controlled because it is not necessary to store records for every prior version of data in the DLDB 414.

Figure 10:
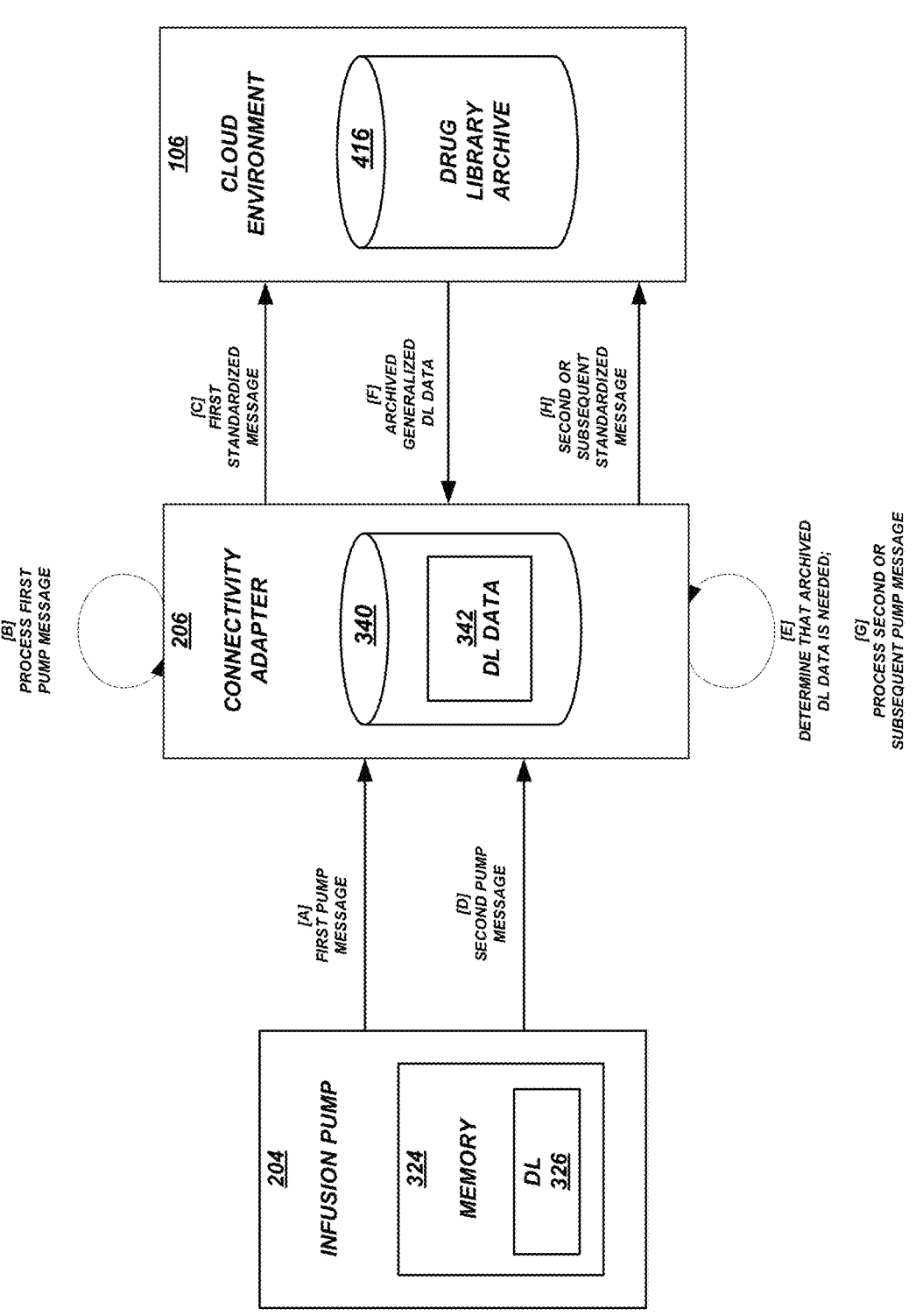
FIG. 10 is a block diagram of various data flows and interactions between drug library manager, an infusion pump, and various other system components during the use of drug libraries according to some embodiments.

At block 724, the process 700 may terminate. In some embodiments, the process 700 may return to prior blocks. For example, a user may return to block 712 to generate additional worksheets for other CCAs, infusion pumps, etc. Example Drug Library Use FIG. 10 is a diagram of data flows and interactions between components of the networked clinical environment 102 and cloud environment 106 during use of drug library data. As shown, an infusion pump 204 may send a message at [A] to a connectivity adapter 206. For example, the message may indicate the start of a medication infusion process for a particular medication. The customized drug library data used by the infusion pump 204 may use an identifier of "13BSF68X" for the medication. Therefore, the message may include the identifier "13BSF68X" instead of the name of the medication, in order to reduce the size of the message. The message may include other information about the infusion, such as a timestamp for the start of the infusion, a dosage amount, etc. Alternatively or in addition, to reduce the overall size of the message, the message may include identifiers for other data regarding the infusion, or other information from which human-readable forms can be derived. For example, the message may include a patient identifier, an infusion type identifier, a CCA identifier, a channel identifier, a line identifier, an auto-program reference identifier, other identifiers, some combination thereof, etc.

The connectivity adapter 206 may receive the message from the infusion pump, and process the message at [B]. For example, the connectivity adapter 206 may process the message into a standardized dataset message using generalized drug library data in the data store 340. The generalized drug library data may include the name of the drug that corresponds to the identifier "13BSF68X," the name of the CCA that corresponds to a CCA identifier, etc. The connectivity adapter 206 may therefore include the drug name, CCA name, etc. in the standardized dataset message without receiving the drug name, CCA name, and the like from the infusion pump 204. The connectivity adapter 206 may send the standardized dataset message to the cloud environment 106 at [C].

The infusion pump 204 may send a second message to the connectivity adapter 206 at [D]. The second message may relate to a past event at the infusion pump 204, such as an infusion occurring days earlier when a different version of customized drug library data was being used by the infusion pump 204. For example, when the cloud environment 106 received the standardized dataset message at [C], it may have determined that a prior message had not been received (e.g., by inspecting a sequential message identifier in the message). The cloud environment 106 may then have initiated a process to obtain the missing message, and as a result the infusion pump 204 re-sent (or sent for the first time) the message to the connectivity adapter 206 at [D].

The connectivity adapter 206 can begin processing the second message at [E]. However, the infusion that is the subject of the message occurred when the infusion pump 204 was using an older version of the customized drug library data. Therefore, the message may include information (e.g., an identifier) that the connectivity adapter 206 is unable to resolve by referencing the generalized drug library data currently present in the data store 340, because generalized drug library data currently present in the data store 340 corresponds to the current customized drug library data used by the infusion pump 204. In this instance, the connectivity adapter 206 may retrieve, from the cloud environment 106 at [F], an archived version of the generalized drug library data that corresponds to the customized drug library data used by the infusion pump 204 when the second message was originally generated.

The connectivity adapter 206 may proceed with processing the second message at [G] into a standardized dataset message using the archived version of generalized drug library data. For example, the connectivity adapter 206 may determine the drug name using the identifier and the archived version of the generalized drug library data and proceed with processing the second message at [G] into a standardized dataset message that includes the drug name. The connectivity adapter 206 may then send a second standardized dataset message to the cloud environment 106 at [H].

Embodiments of the present disclosure can be defined by the following non-limiting clauses:

Clause 1: A system configured to manage a drug library within a clinical environment, the system comprising:

a plurality of infusion pumps configured to deliver medication to one or more patients, each respective infusion pump of the plurality of infusion pumps comprising a memory configured to store drug library data;

a drug library manager comprising one or more computer processors and memory, the drug library manager configured to:

receive, from a user device, first input data representing one or more medications;

receive, from the user device, second input data representing one or more administration rules, wherein the second input data comprises:

data representing a medication of the one or more medications;

data representing an infusion pump type of a plurality of infusion pump types; and data representing one or more medication administration parameters;

receive, from the user device, third input data representing one or more clinical care areas, wherein the third input data comprises:

data representing one or more clinical care area settings; and data representing an association of a clinical care area with zero or more administration rules;

receive, from the user device, fourth input data representing selection of a first clinical care area of the one or more clinical care areas; store, in a drug library database, worksheet data representing a drug library, wherein the worksheet data comprises:

a first reference to infusion pump data in the drug library database, the infusion pump data representing the first infusion pump type; and a second reference to clinical care area data in the drug library database, the clinical care area data representing the first clinical care area;

generate customized drug library data using the worksheet data, wherein the customized drug library data is formatted according to a pump-specific format associated with the first infusion pump type, wherein the customized drug library data represents a subset of medications in the drug library database and a subset of administration rules in the drug library database, and wherein individual administration rules of the subset of administration rules are associated with individual medications of the subset of medications;

generate generalized drug library data using the worksheet data, wherein the generalized drug library data represents the subset of medications and the subset of administration rules;

provide, to a first infusion pump of the plurality of infusion pumps, the customized drug library data, wherein the first infusion pump is associated with the first infusion pump type, and wherein a second infusion pump of the plurality of infusion pumps is not provided with the customized drug library data, the second infusion pump associated with a second infusion pump type; and provide, to a connectivity adapter in communication with the first infusion pump and the second infusion pump, the generalized drug library data.

Clause 2: The system of Clause 1, wherein the first infusion pump is configured to replace, in memory of the first infusion pump, a prior version of customized drug library data with the customized drug library data.

Clause 3: The system of Clause 1, wherein the first infusion pump is configured to:

display infusion data comprising a medication name; and transmit an infusion message to the connectivity adapter, wherein the infusion message comprises a medication identifier and does not comprise the medication name.

Clause 4: The system of Clause 3, wherein the connectivity adapter is configured to at least:

receive, from the first infusion pump, the infusion message; and determine the medication name using the medication identifier and the generalized drug library data.

Clause 5: The system of Clause 4, wherein the connectivity adapter is further configured to at least:

receive, from the second infusion pump, a second infusion message comprising a second medication identifier; and determine a second medication name using the second medication identifier and second generalized drug library data associated with the second infusion pump.

Clause 6: The system of Clause 1, wherein:

an administration rule of the subset of administration rules is associated with a medication of the subset of medications;

the administration rule is associated with a first upper dosing limit;

the first clinical care area is associated with a second upper dosing limit that is lower than the first upper dosing limit; and the second upper dosing limit overrides the first upper dosing limit during administration of the medication by the first infusion pump.

Clause 7: The system of Clause 1, wherein:

an administration rule of the subset of administration rules is associated with a medication of the subset of medications;

the administration rule is associated with a first upper dosing limit;

the first clinical care area is associated with a second upper dosing limit that is higher than the first upper dosing limit; and the first upper dosing limit is implemented during administration of the medication by the first infusion pump.

Clause 8: The system of Clause 1, wherein the drug library manager is further configured to at least:

receive, from the user device, input associated with a medication and representing selection of at least one of: a lower hard dosing limit, a lower soft dosing limit, an upper soft dosing limit, or an upper hard dosing limit; and store, in the drug library database, administration rule data representing the selection, wherein the administration rule data references medication data representing the medication.

Clause 9: The system of Clause 1, wherein the connectivity adapter is configured to at least:

receive, from the first infusion pump, an infusion message associated with a prior version of customized drug library data;

obtain a prior version of generalized drug library data that corresponds to the prior version of customized drug library data; and process the infusion message using the prior version of generalized drug library data.

Clause 10: The system of Clause 1, wherein the drug library manager is further configured to at least:

store status data in connection with the worksheet data, wherein the status data indicates a status of the worksheet data; and receive, from the user device, input indicating a change in status of the worksheet data, wherein the customized drug library data and generalized drug library data are generated in response to receiving the input indicating the change in status of the worksheet data.

Clause 11: The system of Clause 1, further comprising a drug library archive, wherein the drug library manager is further configured to provide the generalized drug library data to the drug library archive, and wherein the drug library archive is configured to store a plurality of versions of generalized drug library data for each of a plurality of different drug libraries.

Clause 12: The system of Clause 11, wherein the drug library manager is further configured to:

compare the generalized drug library data to one of: second generalized drug library data or second worksheet data; and generate user interface data for displaying a difference based on comparing the generalized drug library data.

Clause 13: A computer-implemented method comprising:

under control of one or more computing devices configured with specific computer-executable instructions, storing, in a drug library database, worksheet data representing a drug library, wherein the worksheet data comprises:

a first reference to infusion pump data in the drug library database, the infusion pump data representing a first infusion pump type of a plurality of infusion pump types; and a second reference to clinical care area data in the drug library database, the clinical care area data representing a first clinical care area of a plurality of clinical care areas;

generating customized drug library data using the worksheet data, wherein the customized drug library data is formatted according to a pump-specific format associated with the first infusion pump type, wherein the customized drug library data represents a subset of medications in the drug library database and a subset of administration rules in the drug library database, and wherein individual administration rules of the subset of administration rules are associated with individual medications of the subset of medications;

generating generalized drug library data using the worksheet data, wherein the generalized drug library data represents the subset of medications and the subset of administration rules;

providing the customized drug library data to an infusion pump associated with the first infusion pump type; and providing the generalized drug library data to a computing system in communication with the infusion pump.

Clause 14: The computer-implemented method of Clause 13, further comprising:

accessing archived generalized drug library data corresponding to a prior version of the worksheet data;

comparing the generalized drug library data to the archived generalized drug library data; and presenting a user interface displaying a difference between the generalized drug library data and the archived generalized drug library data.

Clause 15: The computer-implemented method of Clause 13, further comprising:

receiving input associated with a medication and representing selection of at least one of: a lower hard dosing limit, a lower soft dosing limit, an upper soft dosing limit, or an upper hard dosing limit; and storing, in the drug library database, administration rule data representing the selection, wherein the administration rule data references medication data representing the medication.

Clause 16: The computer-implemented method of Clause 13, further comprising:

storing status data in connection with the worksheet data, wherein the status data indicates a status of the worksheet data; and receiving input indicating a change in status of the worksheet data, wherein the customized drug library data and generalized drug library data are generated in response to receiving the input indicating the change in status of the worksheet data.

Clause 17: The computer-implemented method of Clause 13, further comprising providing the generalized drug library data to a drug library archive configured to store a plurality of versions of generalized drug library data for each of a plurality of different drug libraries.

Clause 18: The computer-implemented method of Clause 13, wherein generating the generalized drug library data comprises formatting the generalized drug library data using JavaScript Object Notation.

Clause 19: A system comprising:

a computer-readable memory storing executable instructions; and one or more processors in communication with the computer-readable memory, wherein the one or more processors are programmed by the executable instructions to at least:

store, in a drug library database, worksheet data representing a drug library, wherein the worksheet data comprises:

a first reference to infusion pump data in the drug library database, the infusion pump data representing a first infusion pump type of a plurality of infusion pump types; and a second reference to clinical care area data in the drug library database, the clinical care area data representing a first clinical care area of a plurality of clinical care areas;

generate customized drug library data using the worksheet data, wherein the customized drug library data is formatted according to a pump-specific format associated with the first infusion pump type, wherein the customized drug library data represents a subset of medications in the drug library database and a subset of administration rules in the drug library database, and wherein individual administration rules of the subset of administration rules are associated with individual medications of the subset of medications;

generate generalized drug library data using the worksheet data, wherein the generalized drug library data represents the subset of medications and the subset of administration rules;

provide the customized drug library data to an infusion pump associated with the first infusion pump type; and provide the generalized drug library data to a connectivity adapter in communication with the infusion pump.

Clause 20: The system of Clause 19, further comprising the connectivity adapter, wherein the connectivity adapter is configured to at least:

receive, from the infusion pump, a first infusion message comprising a medication identifier that corresponds to a medication infused by the infusion pump;

determine a medication name using the medication identifier and the generalized drug library data;

receive, from the infusion pump, a second infusion message associated with a prior version of customized drug library data;

obtain a prior version of generalized drug library data that corresponds to the prior version of customized drug library data; and process the second infusion message using the prior version of generalized drug library data.

Clause 21: A system comprising:

computer-readable storage; and one or more computer processors configured to at least:

receive customized drug library data formatted according to a pump-specific format associated with a first infusion pump type, wherein the customized drug library data represents a plurality of medications and a plurality of administration rules, and wherein individual administration rules of the plurality of administration rules are associated with individual medications of the plurality of medications;

receive generalized drug library data, wherein the generalized drug library data represents the plurality of medications and the plurality of administration rules;

send the customized drug library data to an infusion pump associated with the first infusion pump type;

store the generalized drug library data in the computer-readable storage, wherein a prior version of the generalized drug library data is stored in the computer-readable storage;

receive, from the infusion pump, a first infusion message comprising a first medication identifier that corresponds to a first medication infused by the infusion pump;

determine a first medication name using the first medication identifier and the generalized drug library data;

receive, from the infusion pump, a second infusion message associated with a prior version of customized drug library data, the second infusion message comprising a second medication identifier that corresponds to a second medication infused by the infusion pump; and determine a second medication name using the second medication identifier and the prior version of generalized drug library data.

Clause 22: The system of Clause 21, further comprising the infusion pump, wherein the infusion pump is configured to replace, in memory of the infusion pump, a prior version of customized drug library data with the customized drug library data.

Clause 23: The system of Clause 22, wherein the infusion pump is configured to:

display infusion data comprising the first medication name; and transmit the first infusion message to a connectivity adapter comprising the one or more processors, wherein the first infusion message comprises the first medication identifier and does not comprise the first medication name.

Clause 24: The system of Clause 22, wherein the infusion pump is configured to:

display infusion data comprising a clinical care area name; and transmit the first infusion message to a connectivity adapter comprising the one or more processors, wherein the first infusion message comprises a clinical care area identifier and does not comprise the clinical care area name.

Clause 25: The system of Clause 21, wherein the one or more processors are further configured to at least:

receive, from a second infusion pump, a third infusion message comprising a third medication identifier, wherein the second infusion pump is associated with a second infusion pump type; and determine a third medication name using the third medication identifier and second generalized drug library data.

Clause 26: The system of Clause 21, wherein:

an administration rule of the plurality of administration rules is associated with the first medication and a clinical care area of a plurality of clinical care areas;

the administration rule comprises a first upper dosing limit;

the clinical care area is associated with a second upper dosing limit that is lower than the first upper dosing limit; and the second upper dosing limit overrides the first upper dosing limit during administration of the first medication by the infusion pump.

Clause 27: The system of Clause 21, wherein:

an administration rule of the plurality of administration rules is associated with the first medication and a clinical care area of a plurality of clinical care areas;

the administration rule comprises a first upper dosing limit;

the clinical care area is associated with a second upper dosing limit that is higher than the first upper dosing limit; and the first upper dosing limit is implemented during administration of the first medication by the infusion pump.

Clause 28: A computer-implemented method comprising:

under control of one or more computing devices configured with specific computer-executable instructions, receiving customized drug library data formatted according to a pump-specific format associated with a first infusion pump type, wherein the customized drug library data represents a plurality of medications and a plurality of administration rules, and wherein individual administration rules of the plurality of administration rules are associated with individual medications of the plurality of medications;

receiving generalized drug library data, wherein the generalized drug library data represents the plurality of medications and the plurality of administration rules;

sending the customized drug library data to an infusion pump associated with the first infusion pump type;

storing the generalized drug library data in a computer-readable storage, wherein a prior version of the generalized drug library data is stored in the computer-readable storage;

receiving, from the infusion pump, a first infusion message comprising a first medication identifier that corresponds to a first medication infused by the infusion pump;

processing the first infusion message using the first medication identifier and the generalized drug library data;

receiving, from the infusion pump, a second infusion message associated with a prior version of customized drug library data, the second infusion message comprising a second medication identifier that corresponds to a second medication infused by the infusion pump; and processing the second infusion message using the second medication identifier and the prior version of generalized drug library data.

Clause 29: The computer-implemented method of Clause 28, wherein processing the first infusion message comprises determining a first medication name using the first medication identifier and the generalized drug library data.

Clause 30: The computer-implemented method of Clause 28, wherein processing the second infusion message comprises determining a second medication name using the second medication identifier and the generalized drug library data.

Clause 31: The computer-implemented method of Clause 28, wherein sending the customized drug library data to the infusion pump cases causes the infusion pump to replace, in memory of the infusion pump, a prior version of customized drug library data with the customized drug library data.

Clause 32: The computer-implemented method of Clause 31, further comprising:

displaying, by the infusion pump, infusion data comprising the first medication name; and generating, by the infusion pump, the first infusion message, wherein the first infusion message comprises the first medication identifier and does not comprise the first medication name.

Clause 33: The computer-implemented method of Clause 28, further comprising:

receiving, from a second infusion pump, a third infusion message comprising a third medication identifier, wherein the second infusion pump is associated with a second infusion pump type; and processing the third medication identifier and second generalized drug library data.

Clause 34: The computer-implemented method of Clause 28, wherein:

an administration rule of the plurality of administration rules is associated with the first medication and a clinical care area of a plurality of clinical care areas;

the administration rule comprises a first upper dosing limit;

the clinical care area is associated with a second upper dosing limit that is lower than the first upper dosing limit; and the second upper dosing limit overrides the first upper dosing limit during administration of the first medication by the infusion pump.

Clause 35: The computer-implemented method of Clause 28, wherein:

an administration rule of the plurality of administration rules is associated with the first medication and a clinical care area of a plurality of clinical care areas;

the administration rule comprises a first upper dosing limit;

the clinical care area is associated with a second upper dosing limit that is higher than the first upper dosing limit; and the first upper dosing limit is implemented during administration of the first medication by the infusion pump.

Clause 36: A non-transitory computer storage medium that stores an executable component that directs a computing system to perform a process comprising:

receiving customized drug library data formatted according to a pump-specific format associated with a first infusion pump type, wherein the customized drug library data represents a plurality of medications and a plurality of administration rules, and wherein individual administration rules of the plurality of administration rules are associated with individual medications of the plurality of medications;

receiving generalized drug library data, wherein the generalized drug library data represents the plurality of medications and the plurality of administration rules;

sending the customized drug library data to an infusion pump associated with the first infusion pump type;

storing the generalized drug library data in a computer-readable storage, wherein a prior version of the generalized drug library data is stored in the computer-readable storage;

receiving, from the infusion pump, a first infusion message comprising a first medication identifier that corresponds to a first medication infused by the infusion pump;

processing the first infusion message using the first medication identifier and the generalized drug library data;

receiving, from the infusion pump, a second infusion message associated with a prior version of customized drug library data, the second infusion message comprising a second medication identifier that corresponds to a second medication infused by the infusion pump; and processing the second infusion message using the second medication identifier and the prior version of generalized drug library data.

Clause 37: The non-transitory computer storage medium of Clause 36, wherein processing the first infusion message comprises determining a first medication name using the first medication identifier and the generalized drug library data, and wherein processing the second infusion message comprises determining a second medication name using the second medication identifier and the generalized drug library data.

Clause 38: The non-transitory computer storage medium of Clause 36, the process further comprising:

receiving, from a second infusion pump, a third infusion message comprising a third medication identifier, wherein the second infusion pump is associated with a second infusion pump type; and processing the third medication identifier and second generalized drug library data.

Clause 39: The non-transitory computer storage medium of Clause 36, wherein:

an administration rule of the plurality of administration rules is associated with the first medication and a clinical care area of a plurality of clinical care areas;

the administration rule comprises a first upper dosing limit;

the clinical care area is associated with a second upper dosing limit that is lower than the first upper dosing limit; and the second upper dosing limit overrides the first upper dosing limit during administration of the first medication by the infusion pump.

Clause 40: The non-transitory computer storage medium of Clause 36, wherein:

an administration rule of the plurality of administration rules is associated with the first medication and a clinical care area of a plurality of clinical care areas;

the administration rule comprises a first upper dosing limit;

the clinical care area is associated with a second upper dosing limit that is higher than the first upper dosing limit; and the first upper dosing limit is implemented during administration of the first medication by the infusion pump.

OTHER CONSIDERATIONS

It is to be understood that not necessarily all objects or advantages may be achieved in accordance with any particular embodiment described herein. Thus, for example, those skilled in the art will recognize that certain embodiments may be configured to operate in a manner that achieves or optimizes one advantage or group of advantages as taught herein without necessarily achieving other objects or advantages as may be taught or suggested herein.

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and algorithm elements described in connection with the embodiments disclosed herein can be implemented as electronic hardware, computer software, or combinations of both. To clearly illustrate this interchangeability of hardware and software, various illustrative components, blocks, modules, and elements have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC. The ASIC can reside in a user terminal. In the alternative, the processor and the storage medium can reside as discrete components in a user terminal.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements, and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Unless otherwise explicitly stated, articles such as "a", "an", or "the" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B, and C" can include a first processor configured to carry out recitation A working in conjunction with a second processor configured to carry out recitations B and C.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments described herein can be implemented within a form that does not provide all of the features and benefits set forth herein, as some features can be used or practiced separately from others. All such modifications and variations are intended to be included herein within the scope of this disclosure. Further, additional embodiments created by combining any two or more features or techniques of one or more embodiments described herein are also intended to be included herein within the scope of this disclosure.

What is claimed is:

1. A computer-implemented method comprising:
as performed by a connectivity adapter comprising computing hardware configured to operate as an intermediary between a plurality of infusion pumps and a server,
receiving customized drug library data formatted according to a pump-specific format associated with a first infusion pump type of a plurality of infusion pump types, wherein the customized drug library data represents a plurality of medications and a plurality of administration rules;
receiving generalized drug library data, wherein the generalized drug library data represents the plurality of medications and the plurality of administration rules, and wherein the generalized drug library data includes data not included in the customized drug library data;
sending the customized drug library data to an infusion pump associated with the first infusion pump type;
storing the generalized drug library data in a computer-readable storage, wherein a prior version of the generalized drug library data is stored in the computer-readable storage;
receiving, from the infusion pump, an infusion message regarding an infusion event at the infusion pump, the infusion message comprising a message sequence identifier that corresponds to a sequential identifier of the infusion message among a plurality of infusion messages regarding infusion events at the infusion pump, and a medication identifier that corresponds to a medication infused by the infusion pump;
determining that the infusion message is associated with a prior version of the customized drug library data based at least partly on the message sequence identifier, wherein the infusion message is unable to be transformed into a standardized message using the generalized drug library data;
automatically generating a standardized message by transforming the infusion message using the prior version of generalized drug library data; and
sending the standardized message to the server.

2. The computer-implemented method of claim 1, wherein transforming the infusion message comprises determining a medication name using the medication identifier and the prior version of generalized drug library data.

3. The computer-implemented method of claim 1, wherein transforming the infusion message comprises determining a name of a channel, over which the medication was infused by the infusion pump, using a channel identifier included in the infusion message and the prior version of generalized drug library data.

4. The computer-implemented method of claim 1, wherein transforming the infusion message comprises determining a name of a clinical care area within which the medication was infused by the infusion pump, using a clinical care area identifier included in the infusion message and the prior version of generalized drug library data.

5. The computer-implemented method of claim 1, wherein transforming the infusion message comprises determining a name of an auto program according to which the medication was infused by the infusion pump, using an auto program identifier included in the infusion message and the prior version of generalized drug library data.

6. The computer-implemented method of claim 1, wherein determining that the infusion message is associated with the prior version of the customized drug library data comprises determining that the message sequence identifier precedes a second message sequence identifier associated with a second infusion message received prior to the infusion message.

7. The computer-implemented method of claim 1, further comprising:
   accessing archived generalized drug library data;
   comparing the generalized drug library data to the archived generalized drug library data; and
   presenting a user interface displaying a difference between the generalized drug library data and the archived generalized drug library data.

8. The computer-implemented method of claim 1, further comprising:
   receiving input associated with a medication and representing selection of at least one of: a lower hard dosing limit, a lower soft dosing limit, an upper soft dosing limit, or an upper hard dosing limit; and
   storing administration rule data representing the selection in a drug library database, wherein the administration rule data references medication data representing the medication.

9. The computer-implemented method of claim 1, further comprising:
   storing status data in connection with a set of worksheet data, wherein the status data indicates a status of the set of worksheet data; and
   receiving input indicating a change in status of the set of worksheet data, wherein the customized drug library data and generalized drug library data are generated in response to receiving the input indicating the change in status of the set of worksheet data.

10. The computer-implemented method of claim 1, further comprising providing the generalized drug library data to a drug library archive configured to store a plurality of versions generalized drug library data for each of a plurality of different drug libraries.

11. The computer-implemented method of claim 1, wherein sending the customized drug library data to the infusion pump causes the infusion pump to replace, in memory of the infusion pump, the prior version of customized drug library data with the customized drug library data.

12. The computer-implemented method of claim 1, further comprising:
   receiving, from a second infusion pump, a second infusion message comprising a second medication identifier, wherein the second infusion pump is associated with a second infusion pump type; and
   determining a second medication name using the second medication identifier and the generalized drug library data.

13. A system comprising:
   a connectivity adapter configured to operate as an intermediary between a server and a plurality of infusion pumps, wherein the connectivity adapter comprises one or more processors in communication with computer-readable memory and programmed by executable instructions to:
   receive customized drug library data formatted according to a pump-specific format associated with a first infusion pump type of a plurality of infusion pump types, wherein the customized drug library data represents a plurality of medications and a plurality of administration rules;
   receive generalized drug library data, wherein the generalized drug library data represents the plurality of medications and the plurality of administration rules, and wherein the generalized drug library data includes data not included in the customized drug library data;
   send the customized drug library data to an infusion pump associated with the first infusion pump type;
   store the generalized drug library data in a computer-readable storage, wherein a prior version of the generalized drug library data is stored in the computer-readable storage;
   receive, from the infusion pump, an infusion message regarding an infusion event at the infusion pump, the infusion message comprising a message sequence identifier that corresponds to a sequential identifier of the infusion message among a plurality of infusion messages regarding infusion events at the infusion pump, and a medication identifier that corresponds to a medication infused by the infusion pump;
   determine that the infusion message is associated with a prior version of the customized drug library data based at least partly on the message sequence identifier, wherein the infusion message is unable to be transformed into a standardized message using the generalized drug library data;
   automatically generate a standardized message by transforming the infusion message using the prior version of generalized drug library data; and
   send the standardized message to the server.

14. The system of claim 13, wherein to transform the infusion message, the one or more processors are further programmed by the executable instructions to determine a medication name using the medication identifier and the prior version of generalized drug library data.

15. The system of claim 13, wherein to transform the infusion message, the one or more processors are further programmed by the executable instructions to determine a name of a channel, over which the medication was infused by the infusion pump, using a channel identifier included in the infusion message and the prior version of generalized drug library data.

16. The system of claim 13, wherein to transform the infusion message, the one or more processors are further programmed by the executable instructions to determine a name of an auto program according to which the medication was infused by the infusion pump, using an auto program identifier included in the infusion message and the prior version of generalized drug library data.

17. The system of claim 13, wherein to determine that the infusion message is associated with the prior version of the customized drug library data, the one or more processors are further programmed by the executable instructions to determine that the message sequence identifier precedes a second message sequence identifier associated with a second infusion message received prior to the infusion message.

18. The system of claim 13, further comprising the infusion pump, wherein the infusion pump is configured to replace, in memory of the infusion pump, the prior version of customized drug library data with the customized drug library data.

19. The system of claim 13, wherein the one or more processors are further programmed by the executable instructions to:

receive, from a second infusion pump, a second infusion message comprising a second medication identifier, wherein the second infusion pump is associated with a second infusion pump type; and determine a second medication name using the second medication identifier and the generalized drug library data.

20. The system of claim 13, wherein the one or more processors are further configured to:

receive a second infusion message prior to receiving the infusion message, wherein the second infusion message comprises a second message sequence identifier that corresponds to a second sequential identifier of the second infusion message;

determine, based on the second message sequence identifier, that a missing message was not received from the infusion pump; and initiate obtaining the missing message, wherein the infusion message is the missing message.

* * * * *